United States Patent
Bogusky

(10) Patent No.: US 10,583,271 B2
(45) Date of Patent: Mar. 10, 2020

(54) METHOD OF ANCHORING PULLWIRE DIRECTLY ARTICULATABLE REGION IN CATHETER

(71) Applicant: Auris Health, Inc., Redwood City, CA (US)

(72) Inventor: Joseph Bogusky, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 632 days.

(21) Appl. No.: 14/844,099

(22) Filed: Sep. 3, 2015

(65) Prior Publication Data
US 2015/0374956 A1 Dec. 31, 2015

Related U.S. Application Data

(63) Continuation of application No. 13/687,294, filed on Nov. 28, 2012, now abandoned.

(51) Int. Cl.
*A61B 5/04* (2006.01)
*A61B 18/18* (2006.01)
(Continued)

(52) U.S. Cl.
CPC ......... *A61M 25/0147* (2013.01); *A61B 34/30* (2016.02); *A61M 25/0012* (2013.01);
(Continued)

(58) Field of Classification Search
CPC ......... A61B 34/30; A61B 34/20; A61B 34/71; A61B 34/37; A61B 34/77;
(Continued)

(56) References Cited

U.S. PATENT DOCUMENTS 3,572,325 A 3/1971 Bazell et al.
4,644,237 A 2/1987 Frushour et al.
(Continued)

FOREIGN PATENT DOCUMENTS

CA 2285342 A1 10/1998
DE 102013100605 7/2014
(Continued)

OTHER PUBLICATIONS

Extended European Search Report for European Patent Application No. 16167501.2, dated May 30, 2016 (9 pages).
(Continued)

*Primary Examiner* — Joseph A Stoklosa
*Assistant Examiner* — Brian M Antiskay
(74) *Attorney, Agent, or Firm* — Knobbe, Martens, Olson & Bear LLP

(57) ABSTRACT

A catheter comprises a flexible polymer catheter body including a proximal shaft section and a distal working section, a wire support structure embedded within the distal working section of the catheter body, a proximal adapter mounted to the proximal shaft section of the catheter body, and a wire disposed within the catheter body. The wire has a proximal end and a distal end. The proximal end of the wire being operably connected to the proximal adapter, and the distal end of the wire is anchored to the wire support structure.

16 Claims, 29 Drawing Sheets

(51) Int. Cl.
*A61M 25/01* (2006.01)
*A61M 25/00* (2006.01)
*A61B 34/30* (2016.01)
*A61B 18/14* (2006.01)

(52) U.S. Cl.
CPC ..... *A61M 25/0052* (2013.01); *A61B 18/1492* (2013.01); *A61B 2034/301* (2016.02); *A61M 2025/015* (2013.01); *A61M 2025/0161* (2013.01); *A61M 2205/50* (2013.01); *A61M 2209/01* (2013.01); *Y10T 29/49117* (2015.01); *Y10T 29/49879* (2015.01)

(58) Field of Classification Search
CPC .......... A61B 2034/301; A61B 18/1492; A61B 2034/715; A61B 2017/00243
USPC ........ 600/372–375, 380–381, 393, 434–435, 600/508–509; 604/95.04; 606/20–50
See application file for complete search history.

(56) References Cited

U.S. PATENT DOCUMENTS

| | | |
|---|---|---|
| 4,748,969 A | 6/1988 | Wardle |
| 4,925,445 A | 5/1990 | Sakamoto et al. |
| 4,945,305 A | 7/1990 | Blood |
| 4,976,812 A | 12/1990 | McConnell et al. |
| 5,003,982 A | 4/1991 | Halperin |
| 5,060,632 A | 10/1991 | Hibino et al. |
| 5,067,346 A | 11/1991 | Field |
| 5,078,714 A | 1/1992 | Katims |
| 5,146,835 A | 9/1992 | McConnell et al. |
| 5,168,864 A | 12/1992 | Shockey |
| 5,280,781 A | 1/1994 | Oku |
| 5,320,696 A | 6/1994 | McConnell et al. |
| 5,339,799 A | 8/1994 | Kami et al. |
| 5,341,807 A | 8/1994 | Nardella |
| 5,368,015 A | 11/1994 | Wilk |
| 5,394,875 A | 3/1995 | Lewis et al. |
| 5,397,443 A | 3/1995 | Michaels |
| 5,398,691 A | 3/1995 | Martin et al. |
| 5,408,263 A | 4/1995 | Kikuchi |
| 5,408,409 A | 4/1995 | Glassman et al. |
| 5,433,215 A | 7/1995 | Athanasiou et al. |
| 5,447,529 A | 9/1995 | Marchlinski et al. |
| 5,469,857 A | 11/1995 | Laurent et al. |
| 5,477,856 A | 12/1995 | Lundquist |
| 5,492,131 A | 2/1996 | Galel |
| 5,524,635 A | 6/1996 | Uflacker et al. |
| 5,549,542 A | 8/1996 | Kovalcheck |
| 5,569,220 A | 10/1996 | Webster, Jr. |
| 5,600,330 A | 2/1997 | Blood |
| 5,631,973 A | 5/1997 | Green |
| 5,662,108 A | 9/1997 | Budd et al. |
| 5,672,877 A | 9/1997 | Liebig et al. |
| 5,673,704 A | 10/1997 | Marchlinski et al. |
| 5,676,653 A | 10/1997 | Taylor et al. |
| 5,697,377 A | 12/1997 | Wittkampf |
| 5,713,946 A | 2/1998 | Ben-Haim |
| 5,722,959 A | 3/1998 | Bierman |
| 5,738,096 A | 4/1998 | Ben-Haim |
| 5,749,362 A | 5/1998 | Funda et al. |
| 5,754,741 A | 5/1998 | Wang et al. |
| 5,762,458 A | 6/1998 | Wang et al. |
| 5,784,542 A | 7/1998 | Ohm et al. |
| 5,799,055 A | 8/1998 | Peshkin et al. |
| 5,810,716 A | 9/1998 | Mukherjee et al. |
| 5,815,640 A | 9/1998 | Wang et al. |
| 5,825,982 A | 10/1998 | Wright et al. |
| 5,833,608 A | 11/1998 | Acker |
| 5,836,869 A | 11/1998 | Kudo et al. |
| 5,836,874 A | 11/1998 | Swanson et al. |
| 5,836,990 A | 11/1998 | Li |
| 5,843,076 A | 12/1998 | Webster, Jr. et al. |
| 5,845,646 A | 12/1998 | Lemelson |
| 5,876,325 A | 3/1999 | Mizuno et al. |
| 5,878,193 A | 3/1999 | Wang et al. |
| 5,891,095 A | 4/1999 | Eggers et al. |
| 5,899,851 A | 5/1999 | Koninckx |
| 5,911,694 A | 6/1999 | Ikeda et al. |
| 5,925,078 A | 7/1999 | Anderson |
| 5,935,079 A | 8/1999 | Swanson et al. |
| 5,950,629 A | 9/1999 | Taylor et al. |
| 5,953,683 A | 9/1999 | Hansen et al. |
| 5,983,126 A | 11/1999 | Wittkampf |
| 6,004,016 A | 12/1999 | Spector |
| 6,004,271 A | 12/1999 | Moore |
| 6,061,587 A | 5/2000 | Kucharczyk et al. |
| 6,063,022 A | 5/2000 | Ben-Haim |
| 6,063,095 A | 5/2000 | Wang et al. |
| 6,068,604 A | 5/2000 | Krause et al. |
| 6,080,181 A | 6/2000 | Jensen et al. |
| 6,083,170 A | 7/2000 | Ben-Haim |
| 6,096,004 A | 8/2000 | Meglan et al. |
| 6,102,850 A | 8/2000 | Wang et al. |
| 6,106,511 A | 8/2000 | Jensen |
| 6,126,651 A | 10/2000 | Mayer |
| 6,129,668 A | 10/2000 | Haynor et al. |
| 6,132,368 A | 10/2000 | Cooper |
| 6,161,032 A | 12/2000 | Acker |
| 6,172,499 B1 | 1/2001 | Ashe |
| 6,198,974 B1 * | 3/2001 | Webster, Jr. ...... A61M 25/0136 600/146 |
| 6,203,493 B1 | 3/2001 | Ben-Haim |
| 6,226,543 B1 | 5/2001 | Gilboa et al. |
| 6,228,028 B1 | 5/2001 | Klein et al. |
| 6,233,476 B1 | 5/2001 | Strommer et al. |
| 6,233,504 B1 | 5/2001 | Das et al. |
| 6,246,200 B1 | 6/2001 | Blumenkranz et al. |
| 6,266,551 B1 | 7/2001 | Osadchy et al. |
| 6,272,371 B1 | 8/2001 | Shlomo |
| 6,301,496 B1 | 10/2001 | Reisfeld |
| 6,309,397 B1 | 10/2001 | Julian et al. |
| 6,310,828 B1 | 10/2001 | Mumm et al. |
| 6,312,435 B1 | 11/2001 | Wallace et al. |
| 6,314,856 B1 | 11/2001 | Keith et al. |
| 6,331,181 B1 | 12/2001 | Tierney et al. |
| 6,363,279 B1 | 3/2002 | Ben-Haim et al. |
| 6,370,411 B1 | 4/2002 | Osadchy et al. |
| 6,371,952 B1 | 4/2002 | Madhani et al. |
| 6,375,471 B1 | 4/2002 | Wendlandt et al. |
| 6,380,732 B1 | 4/2002 | Gilboa |
| 6,384,483 B1 | 5/2002 | Igarashi et al. |
| 6,393,340 B2 | 5/2002 | Funda et al. |
| 6,398,731 B1 | 6/2002 | Mumm et al. |
| 6,400,979 B1 | 6/2002 | Stoianovici et al. |
| 6,415,171 B1 | 7/2002 | Gueziec et al. |
| 6,424,885 B1 | 7/2002 | Niemeyer et al. |
| 6,459,926 B1 | 10/2002 | Nowlin |
| 6,468,260 B1 | 10/2002 | Bumbalough et al. |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,517,477 B1 | 2/2003 | Wendlandt |
| 6,526,859 B1 | 3/2003 | Ozawa et al. |
| 6,530,913 B1 | 3/2003 | Giba et al. |
| 6,544,230 B1 | 4/2003 | Flaherty et al. |
| 6,551,273 B1 | 4/2003 | Olson et al. |
| 6,565,554 B1 | 5/2003 | Niemeyer |
| 6,574,355 B2 | 6/2003 | Green |
| 6,580,938 B1 | 6/2003 | Acker |
| 6,587,750 B2 | 7/2003 | Gerbi et al. |
| 6,594,552 B1 | 7/2003 | Nowlin |
| 6,610,007 B2 | 8/2003 | Belson et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,629,534 B1 | 10/2003 | St. Goar et al. |
| 6,659,939 B2 | 12/2003 | Moll et al. |
| 6,669,709 B1 | 12/2003 | Cohn et al. |
| 6,679,152 B1 | 1/2004 | Head et al. |
| 6,685,698 B2 | 2/2004 | Morley et al. |
| 6,699,235 B2 | 3/2004 | Wallace et al. |

(56) References Cited

U.S. PATENT DOCUMENTS

| | | | |
|---|---|---|---|
| 6,716,166 B2 | 4/2004 | Govari | |
| 6,726,675 B1 | 4/2004 | Beyar | |
| 6,741,883 B2 | 5/2004 | Gildenberg | |
| 6,774,624 B2 | 8/2004 | Anderson et al. | |
| 6,783,524 B2 | 8/2004 | Anderson et al. | |
| 6,786,896 B1 | 9/2004 | Madhani et al. | |
| 6,799,065 B1 | 9/2004 | Niemeyer | |
| 6,817,973 B2 | 11/2004 | Merril et al. | |
| 6,817,974 B2 | 11/2004 | Cooper et al. | |
| 6,837,846 B2 | 1/2005 | Jaffe | |
| 6,852,107 B2 | 2/2005 | Wang et al. | |
| 6,858,003 B2 | 2/2005 | Evans et al. | |
| 6,905,460 B2 | 6/2005 | Wang et al. | |
| 6,963,792 B1 | 11/2005 | Green | |
| 7,008,401 B2 | 3/2006 | Thompson et al. | |
| 7,021,173 B2 | 4/2006 | Stoianovici et al. | |
| 7,074,179 B2 | 7/2006 | Wang et al. | |
| 7,087,049 B2 | 8/2006 | Nowlin et al. | |
| 7,169,141 B2 | 1/2007 | Brock et al. | |
| 7,192,438 B2 | 3/2007 | Margolis | |
| 7,197,354 B2 | 3/2007 | Sobe | |
| 7,225,012 B1 | 5/2007 | Susil et al. | |
| 7,280,863 B2 | 10/2007 | Shachar | |
| 7,297,142 B2 | 11/2007 | Brock | |
| 7,320,700 B2 | 1/2008 | Cooper et al. | |
| 7,331,967 B2 | 2/2008 | Lee et al. | |
| 7,343,195 B2 | 3/2008 | Strommer et al. | |
| 7,371,210 B2 | 5/2008 | Brock et al. | |
| 7,404,824 B1 | 7/2008 | Webler et al. | |
| 7,494,494 B2 | 2/2009 | Stoianovici et al. | |
| 7,540,866 B2 | 6/2009 | Viswanathan et al. | |
| 7,569,052 B2 | 8/2009 | Phan et al. | |
| 7,607,440 B2 | 10/2009 | Coste-Maniere et al. | |
| 7,772,541 B2 | 8/2010 | Froggatt et al. | |
| 7,850,642 B2 | 12/2010 | Moll et al. | |
| 7,963,288 B2 | 6/2011 | Rosenberg et al. | |
| 7,972,298 B2 | 7/2011 | Wallace et al. | |
| 8,052,636 B2 | 11/2011 | Moll et al. | |
| 8,083,691 B2 | 11/2011 | Goldenberg et al. | |
| 8,092,397 B2 | 1/2012 | Wallace et al. | |
| 8,122,809 B2 | 2/2012 | Simpson | |
| 8,190,238 B2 | 5/2012 | Moll et al. | |
| 8,210,085 B2 | 7/2012 | Lindh et al. | |
| 8,219,178 B2 | 7/2012 | Smith et al. | |
| 8,261,648 B1 | 9/2012 | Marchand et al. | |
| 8,335,557 B2 | 12/2012 | Maschke | |
| 8,376,934 B2 | 2/2013 | Takahashi | |
| 8,396,595 B2 | 3/2013 | Dariush | |
| 8,442,618 B2 | 5/2013 | Strommer et al. | |
| 8,498,691 B2 | 7/2013 | Moll et al. | |
| 8,506,555 B2 | 8/2013 | Ruiz Morales | |
| 8,554,368 B2 | 10/2013 | Fielding et al. | |
| 8,671,817 B1 | 3/2014 | Bogusky | |
| 8,720,448 B2 | 5/2014 | Reis et al. | |
| 8,738,181 B2 | 5/2014 | Greer et al. | |
| 8,827,948 B2 | 9/2014 | Romo et al. | |
| 8,894,610 B2 | 11/2014 | Macnamara et al. | |
| 8,929,631 B2 | 1/2015 | Pfister et al. | |
| 8,945,095 B2 | 2/2015 | Blumenkranz | |
| 9,014,851 B2 | 4/2015 | Wong et al. | |
| 9,129,417 B2 | 9/2015 | Zheng et al. | |
| 9,173,713 B2 | 11/2015 | Hart et al. | |
| 9,199,372 B2 | 12/2015 | Henderson et al. | |
| 9,226,796 B2 | 1/2016 | Bowling | |
| 9,256,940 B2 | 2/2016 | Carelsen et al. | |
| 9,289,578 B2 | 3/2016 | Walker et al. | |
| 9,314,306 B2 | 4/2016 | Yu | |
| 9,345,456 B2 | 5/2016 | Tsonton et al. | |
| 9,358,682 B2 | 6/2016 | Ruiz Morales | |
| 9,504,604 B2 | 11/2016 | Alvarez | |
| 9,522,034 B2 | 12/2016 | Johnson | |
| 9,561,083 B2 | 2/2017 | Yu et al. | |
| 9,622,827 B2 | 4/2017 | Yu et al. | |
| 9,629,595 B2 | 4/2017 | Walker et al. | |
| 9,636,184 B2 | 5/2017 | Lee et al. | |
| 9,675,422 B2 | 6/2017 | Hourtash et al. | |
| 9,713,509 B2 | 7/2017 | Schuh et al. | |
| 9,726,476 B2 | 8/2017 | Ramamurthy et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,789,608 B2 | 10/2017 | Itkowitz et al. | |
| 9,818,681 B2 | 11/2017 | Machida | |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 10,016,900 B1 | 7/2018 | Meyer et al. | |
| 10,022,192 B1 | 7/2018 | Ummalaneni | |
| 10,145,747 B1 | 12/2018 | Lin et al. | |
| 10,159,532 B1 | 12/2018 | Ummalaneni et al. | |
| 2001/0000040 A1 | 3/2001 | Adams et al. | |
| 2001/0009976 A1 | 7/2001 | Panescu et al. | |
| 2001/0029366 A1 | 10/2001 | Swanson et al. | |
| 2002/0087169 A1 | 7/2002 | Brock et al. | |
| 2002/0133174 A1 | 9/2002 | Charles et al. | |
| 2002/0138009 A1 | 9/2002 | Brockway et al. | |
| 2002/0156369 A1 | 10/2002 | Chakeres | |
| 2002/0161280 A1 | 10/2002 | Chatenever et al. | |
| 2002/0177789 A1 | 11/2002 | Ferry et al. | |
| 2003/0045778 A1 | 3/2003 | Ohline | |
| 2003/0050649 A1 | 3/2003 | Brock et al. | |
| 2003/0055360 A1 | 3/2003 | Zeleznik et al. | |
| 2003/0060927 A1 | 3/2003 | Gerbi et al. | |
| 2003/0073908 A1 | 4/2003 | Desai | |
| 2003/0074011 A1 | 4/2003 | Gilboa et al. | |
| 2003/0109780 A1 | 6/2003 | Goste-Maniere et al. | |
| 2003/0135204 A1 | 7/2003 | Lee et al. | |
| 2003/0182091 A1 | 9/2003 | Kukuk | |
| 2004/0034282 A1 | 2/2004 | Quaid, III | |
| 2004/0034365 A1 | 2/2004 | Lentz et al. | |
| 2004/0152972 A1 | 8/2004 | Hunter | |
| 2004/0171929 A1 | 9/2004 | Leitner et al. | |
| 2004/0176751 A1 | 9/2004 | Weitzner et al. | |
| 2004/0193146 A1 | 9/2004 | Lee et al. | |
| 2004/0220588 A1 | 11/2004 | Kermode et al. | |
| 2004/0257021 A1 | 12/2004 | Chang et al. | |
| 2005/0027397 A1 | 2/2005 | Niemeyer | |
| 2005/0043718 A1 | 2/2005 | Madhani | |
| 2005/0059960 A1 | 3/2005 | Simaan et al. | |
| 2005/0065400 A1 | 3/2005 | Banik | |
| 2005/0070844 A1 | 3/2005 | Chow et al. | |
| 2005/0085728 A1 | 4/2005 | Fukuda | |
| 2005/0131460 A1 | 6/2005 | Gifford, III et al. | |
| 2005/0159789 A1 | 7/2005 | Brockway et al. | |
| 2005/0165276 A1 | 7/2005 | Belson et al. | |
| 2005/0182295 A1 | 8/2005 | Soper et al. | |
| 2005/0182330 A1 | 8/2005 | Brockway et al. | |
| 2005/0200324 A1 | 9/2005 | Guthart et al. | |
| 2005/0203382 A1 | 9/2005 | Govari et al. | |
| 2005/0222554 A1 | 10/2005 | Wallace et al. | |
| 2005/0256398 A1 | 11/2005 | Hastings | |
| 2005/0261551 A1 | 11/2005 | Couvillon | |
| 2006/0013523 A1 | 1/2006 | Childers et al. | |
| 2006/0015096 A1 | 1/2006 | Hauck et al. | |
| 2006/0025679 A1 | 2/2006 | Viswanathan et al. | |
| 2006/0041293 A1* | 2/2006 | Mehdizadeh | A61N 1/056 607/116 |
| 2006/0058647 A1 | 3/2006 | Strommer et al. | |
| 2006/0161045 A1 | 7/2006 | Merril et al. | |
| 2006/0178556 A1 | 8/2006 | Hasser et al. | |
| 2006/0200049 A1 | 9/2006 | Leo et al. | |
| 2006/0271036 A1 | 11/2006 | Garabedian et al. | |
| 2006/0276775 A1 | 12/2006 | Rosenberg et al. | |
| 2006/0293864 A1 | 12/2006 | Soss | |
| 2007/0013336 A1 | 1/2007 | Nowlin et al. | |
| 2007/0016130 A1 | 1/2007 | Leeflang et al. | |
| 2007/0038181 A1 | 2/2007 | Melamud et al. | |
| 2007/0043338 A1 | 2/2007 | Moll et al. | |
| 2007/0043455 A1 | 2/2007 | Viswanathan | |

(56) References Cited

U.S. PATENT DOCUMENTS

| | | |
|---|---|---|
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0123851 A1 | 5/2007 | Alejandro et al. |
| 2007/0135886 A1 | 6/2007 | Maschke |
| 2007/0150155 A1 | 6/2007 | Kawai |
| 2007/0156123 A1 | 7/2007 | Moll et al. |
| 2007/0197896 A1 | 8/2007 | Moll et al. |
| 2007/0197939 A1 | 8/2007 | Wallace et al. |
| 2007/0249901 A1 | 10/2007 | Ohline et al. |
| 2007/0249911 A1 | 10/2007 | Simon |
| 2007/0253599 A1 | 11/2007 | White et al. |
| 2007/0270679 A1 | 11/2007 | Nguyen et al. |
| 2007/0282167 A1 | 12/2007 | Barenboym et al. |
| 2007/0287992 A1 | 12/2007 | Diolaiti |
| 2007/0287999 A1 | 12/2007 | Malecki et al. |
| 2007/0293724 A1 | 12/2007 | Saadat et al. |
| 2007/0299353 A1 | 12/2007 | Harlev et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0033284 A1 | 2/2008 | Hauck |
| 2008/0046122 A1 | 2/2008 | Manzo et al. |
| 2008/0108870 A1 | 5/2008 | Wiita et al. |
| 2008/0123921 A1 | 5/2008 | Gielen et al. |
| 2008/0140087 A1 | 6/2008 | Barbagli et al. |
| 2008/0159653 A1 | 7/2008 | Dunki-Jacobs et al. |
| 2008/0183071 A1 | 7/2008 | Strommer et al. |
| 2008/0188890 A1 | 8/2008 | Weitzner et al. |
| 2008/0231221 A1 | 9/2008 | Ogawa |
| 2008/0249640 A1 | 10/2008 | Vittor et al. |
| 2008/0255505 A1 | 10/2008 | Carlson et al. |
| 2008/0262480 A1 | 10/2008 | Stahler et al. |
| 2008/0275367 A1 | 11/2008 | Barbagli et al. |
| 2008/0281293 A1 | 11/2008 | Peh et al. |
| 2008/0300592 A1 | 12/2008 | Weitzner et al. |
| 2008/0312771 A1 | 12/2008 | Sugiura |
| 2008/0319311 A1 | 12/2008 | Hamadeh |
| 2009/0005768 A1* | 1/2009 | Sharareh ............ A61B 18/1492 606/17 |
| 2009/0012533 A1 | 1/2009 | Barbagli et al. |
| 2009/0024141 A1 | 1/2009 | Stahler et al. |
| 2009/0054884 A1 | 2/2009 | Farley et al. |
| 2009/0076534 A1 | 3/2009 | Shelton |
| 2009/0099554 A1 | 4/2009 | Forster et al. |
| 2009/0137952 A1 | 5/2009 | Ramamurthy et al. |
| 2009/0184825 A1 | 7/2009 | Anderson |
| 2009/0198298 A1 | 8/2009 | Kaiser et al. |
| 2009/0221908 A1 | 9/2009 | Glossop |
| 2009/0245600 A1 | 10/2009 | Hoffman |
| 2009/0287354 A1 | 11/2009 | Choi |
| 2009/0318797 A1 | 12/2009 | Hadani |
| 2009/0324161 A1 | 12/2009 | Prisco |
| 2010/0030115 A1 | 2/2010 | Fujimoto |
| 2010/0076263 A1 | 3/2010 | Tanaka |
| 2010/0081920 A1 | 4/2010 | Whitmore, III et al. |
| 2010/0121138 A1 | 5/2010 | Goldenberg |
| 2010/0168737 A1 | 7/2010 | Grunewald |
| 2010/0234856 A1 | 9/2010 | Stoianovici et al. |
| 2010/0256812 A1 | 10/2010 | Tsusaka et al. |
| 2010/0280320 A1 | 11/2010 | Alvarez et al. |
| 2010/0280449 A1 | 11/2010 | Alvarez et al. |
| 2010/0280525 A1 | 11/2010 | Alvarez et al. |
| 2011/0152880 A1 | 1/2011 | Alvarez et al. |
| 2011/0048216 A1 | 3/2011 | Lindh et al. |
| 2011/0082366 A1 | 4/2011 | Scully et al. |
| 2011/0082462 A1 | 4/2011 | Suarez |
| 2011/0137122 A1 | 6/2011 | Kawai |
| 2011/0153252 A1 | 6/2011 | Govari |
| 2011/0160570 A1 | 6/2011 | Kariv |
| 2011/0162195 A1 | 7/2011 | Webster et al. |
| 2011/0196199 A1 | 8/2011 | Donhowe et al. |
| 2011/0257480 A1 | 10/2011 | Takahashi |
| 2011/0258842 A1 | 10/2011 | Dukesherer et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0071752 A1 | 3/2012 | Sewell |
| 2012/0071822 A1* | 3/2012 | Romo ...................... A61B 6/12 604/95.04 |
| 2012/0123441 A1 | 5/2012 | Au |
| 2012/0130217 A1* | 5/2012 | Kauphusman ....... A61B 5/0422 600/373 |
| 2012/0137491 A1 | 6/2012 | Macnamara |
| 2012/0209293 A1 | 8/2012 | Carlson |
| 2012/0215094 A1 | 8/2012 | Rahimian et al. |
| 2012/0221038 A1 | 8/2012 | Simpson |
| 2012/0253276 A1 | 10/2012 | Govari et al. |
| 2012/0328077 A1 | 12/2012 | Bouvier |
| 2013/0085330 A1 | 4/2013 | Ramamurthy et al. |
| 2013/0090530 A1 | 4/2013 | Ramamurthy |
| 2013/0102846 A1 | 4/2013 | Sjostrom |
| 2013/0131503 A1 | 5/2013 | Schneider et al. |
| 2013/0165854 A1 | 6/2013 | Sandhu et al. |
| 2013/0165945 A9* | 6/2013 | Roelle .................... A61B 34/71 606/130 |
| 2013/0218005 A1 | 8/2013 | Desai |
| 2013/0325030 A1 | 12/2013 | Hourtash et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0148673 A1 | 5/2014 | Bogusky |
| 2014/0163664 A1 | 6/2014 | Goldsmith |
| 2014/0222207 A1 | 8/2014 | Bowling et al. |
| 2014/0296870 A1 | 10/2014 | Stern et al. |
| 2014/0309649 A1 | 10/2014 | Alvarez et al. |
| 2014/0316420 A1 | 10/2014 | Ballard et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0088161 A1 | 3/2015 | Hata |
| 2015/0101442 A1 | 4/2015 | Romo |
| 2015/0104284 A1 | 4/2015 | Riedel |
| 2015/0119628 A1 | 4/2015 | Bharat et al. |
| 2015/0119638 A1 | 4/2015 | Yu et al. |
| 2015/0164594 A1 | 6/2015 | Romo et al. |
| 2015/0164596 A1 | 6/2015 | Romo |
| 2015/0202015 A1 | 7/2015 | Elhawary |
| 2015/0223902 A1 | 8/2015 | Walker et al. |
| 2015/0265359 A1 | 9/2015 | Camarillo |
| 2015/0265807 A1 | 9/2015 | Park et al. |
| 2015/0297864 A1 | 10/2015 | Kokish |
| 2015/0335480 A1 | 11/2015 | Alvarez et al. |
| 2015/0342695 A1 | 12/2015 | He |
| 2015/0359597 A1 | 12/2015 | Gombert et al. |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0081568 A1* | 3/2016 | Kolberg ................... A61N 1/05 600/373 |
| 2016/0100772 A1 | 4/2016 | Ikuma |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0296294 A1 | 10/2016 | Moll et al. |
| 2016/0331469 A1 | 11/2016 | Hall et al. |
| 2016/0338787 A1 | 11/2016 | Popovic |
| 2016/0346924 A1 | 12/2016 | Hasegawa |
| 2016/0354057 A1 | 12/2016 | Hansen et al. |
| 2016/0360947 A1 | 12/2016 | Iida |
| 2016/0360949 A1 | 12/2016 | Hyodo |
| 2016/0374541 A1 | 12/2016 | Agrawal et al. |
| 2017/0007337 A1 | 1/2017 | Dan |

(56) References Cited

U.S. PATENT DOCUMENTS

| | | |
|---|---|---|
| 2017/0056215 A1 | 3/2017 | Nagesh et al. |
| 2017/0065364 A1 | 3/2017 | Schuh et al. |
| 2017/0065365 A1 | 3/2017 | Schuh |
| 2017/0068796 A1 | 3/2017 | Passerini et al. |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0151027 A1 | 6/2017 | Walker et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055583 A1 | 3/2018 | Schuh et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |

FOREIGN PATENT DOCUMENTS

| | | |
|---|---|---|
| EP | 1285634 A1 | 2/2003 |
| EP | 0904796 B1 | 11/2004 |
| EP | 1566150 A2 | 8/2005 |
| EP | 1 800 593 | 6/2007 |
| EP | 2 158 834 | 3/2010 |
| EP | 2204208 A2 | 7/2010 |
| EP | 2 392 435 | 12/2011 |
| EP | 2737922 A1 | 6/2014 |
| EP | 3 025 630 | 6/2016 |
| GB | 2102590 A | 2/1983 |
| WO | 9744089 A1 | 11/1997 |
| WO | 0011495 A1 | 3/2000 |
| WO | 0045193 A1 | 8/2000 |
| WO | 0156457 A1 | 8/2001 |
| WO | 03077769 A1 | 9/2003 |
| WO | 03091839 A2 | 11/2003 |
| WO | 2004039273 A2 | 5/2004 |
| WO | 20040104714 A1 | 12/2004 |
| WO | 2005032637 A2 | 4/2005 |
| WO | 2005081202 A1 | 9/2005 |
| WO | 2005087128 A1 | 9/2005 |
| WO | 2006122061 A1 | 11/2006 |
| WO | 2007149841 A2 | 12/2007 |
| WO | 2008033589 A1 | 3/2008 |
| WO | 2009120940 A2 | 10/2009 |
| WO | 2010127162 A1 | 11/2010 |
| WO | 2011132409 A1 | 10/2011 |
| WO | WO 15/142957 | 9/2015 |
| WO | WO 17/048194 | 3/2017 |

OTHER PUBLICATIONS

Extended European Search Report for EP Application No. 13193922.5, dated Apr. 14, 2014, Applicant Hansen Medical, Inc. (9 pages).

Amendment and Response to Non-Final Office Action for related U.S. Appl. No. 11/678,016, dated Dec. 27, 2010 (21 pages).

Non-Final Office Action for related U.S. Appl. No. 11/678,016, dated Aug. 31, 2010 (30 pages).

European Office Action issued for related European Patent Application No.07757358.2, dated Dec. 9, 2008 (3 pages).

Chinese Office Action issued for related Chinese Patent Application No.200780006359.8, dated Aug. 9, 2010 (6 pages).

PCT International Preliminary Report on Patentability for International Patent Application No. PCT/US2007/062617, dated Aug. 26, 2008 (7 pages).

PCT International Search Report for International Patent Application No. PCT/US2006/026218, dated Dec. 12, 2006 (2 pages).

PCT International Search Report for International Patent Application No. PCT/US2005/007108, dated Jun. 27, 2005 (4 pages).

PCT International Search Report for International Patent Application No. PCT/US2007/062617, dated Jul. 12, 2007 (3 pages).

PCT Written Opinion for International Patent Application No. PCT/US2006/026218, dated Dec. 12, 2006 (7 pages).

PCT Written Opinion for International Patent Application No. PCT/US2005/007108, dated Jun. 27, 2005 (6 pages).

PCT Written Opinion for International Patent Application No. PCT/US2007/062617, dated Jul. 12, 2007 (6 pages).

Camarillo et al., "Mechanics Modeling of Tendon-Driven Continuum Manipulators," IEEE Transaction on Robotics, Dec. 2008, pp. 1262-1273, vol. 24 No. 6.

Jung et al., "A Modeling Approach for Continuum Robotic Manipulators: Effects of Nonlinear Internal Device Friction," IEEE/RSJ International Conference on Intelligent Robots and Systems, Sep. 25-30, 2011, pp. 5139-5146, California.

Kukuk, Oct. 5, 2001, TBNA-protocols: Guiding TransBronchial Needle Aspirations Without a Computer in the Operating Room, MICCAI 2001, 2208:997-1006.

Verdaasdonk et al., Jan. 23, 2013, Effect of microsecond pulse length and tip shape on explosive bubble formation of 2.78 µm Er,Cr;YSGG and 2.94 µm Er:YAG laser, Proceedings of SPIE, vol. 8221, 12.

Blankenstein, Jun. 2008, Dynamic Registration and High Speed Visual Servoing in Robot-Assisted Surgery, Katholieke Universiteit Leuven, Leuven, Belgium.

\* cited by examiner

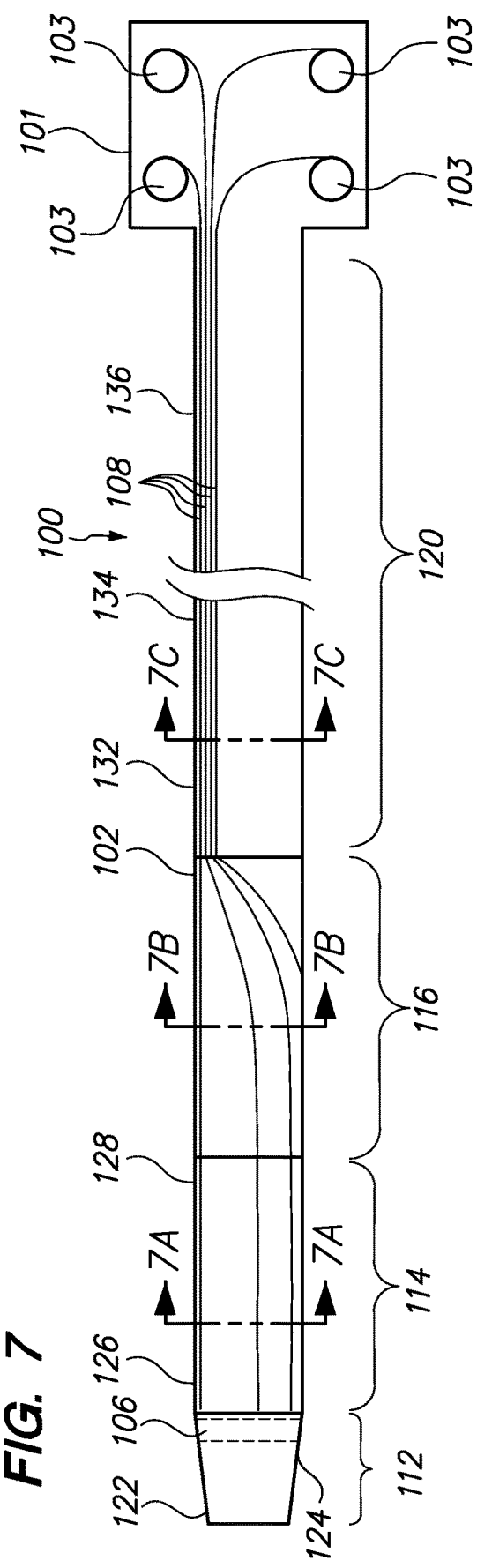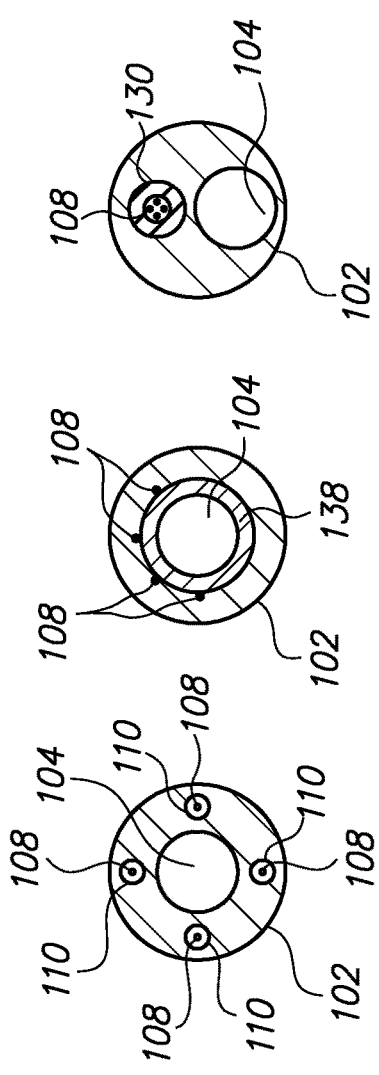

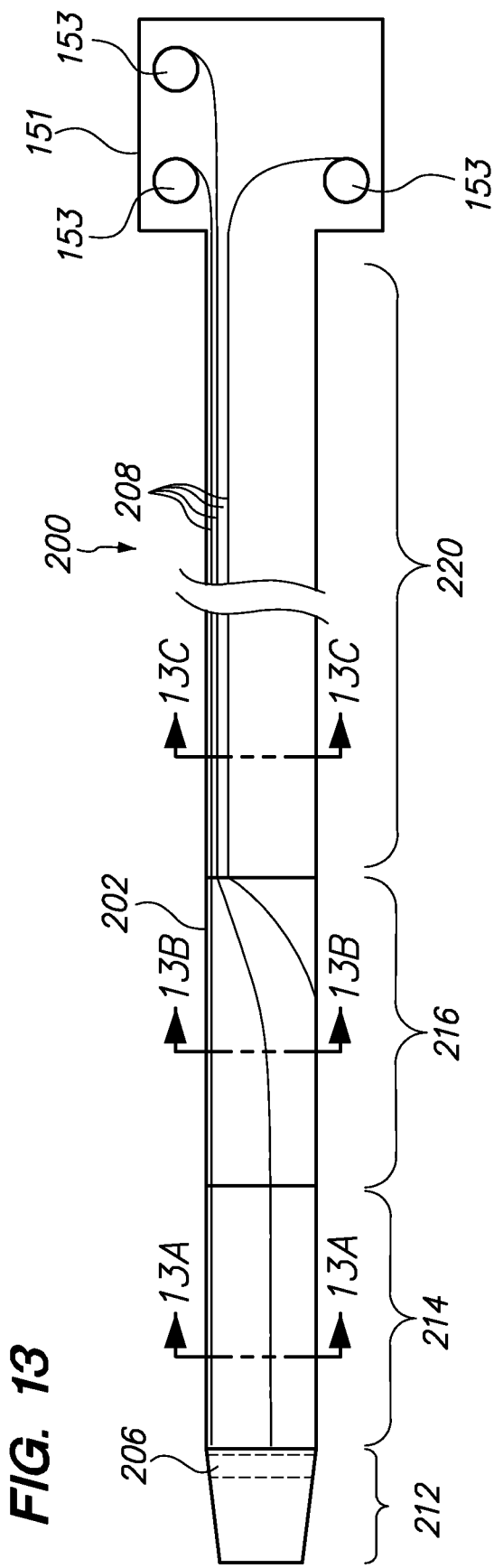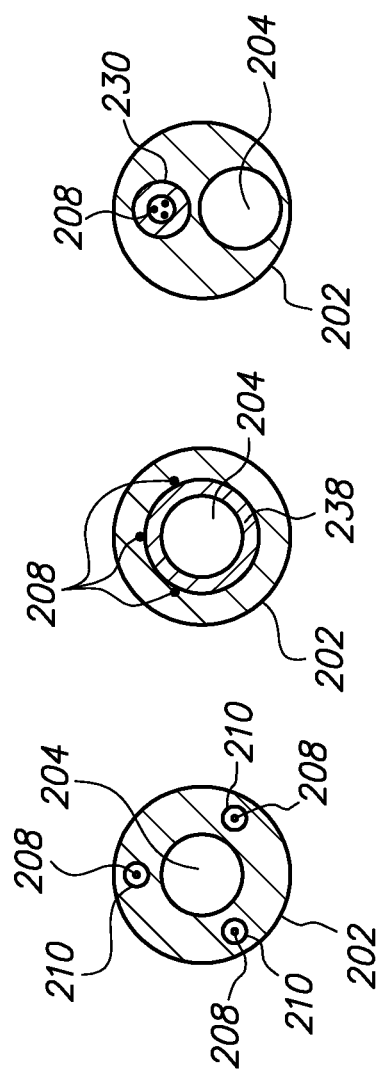

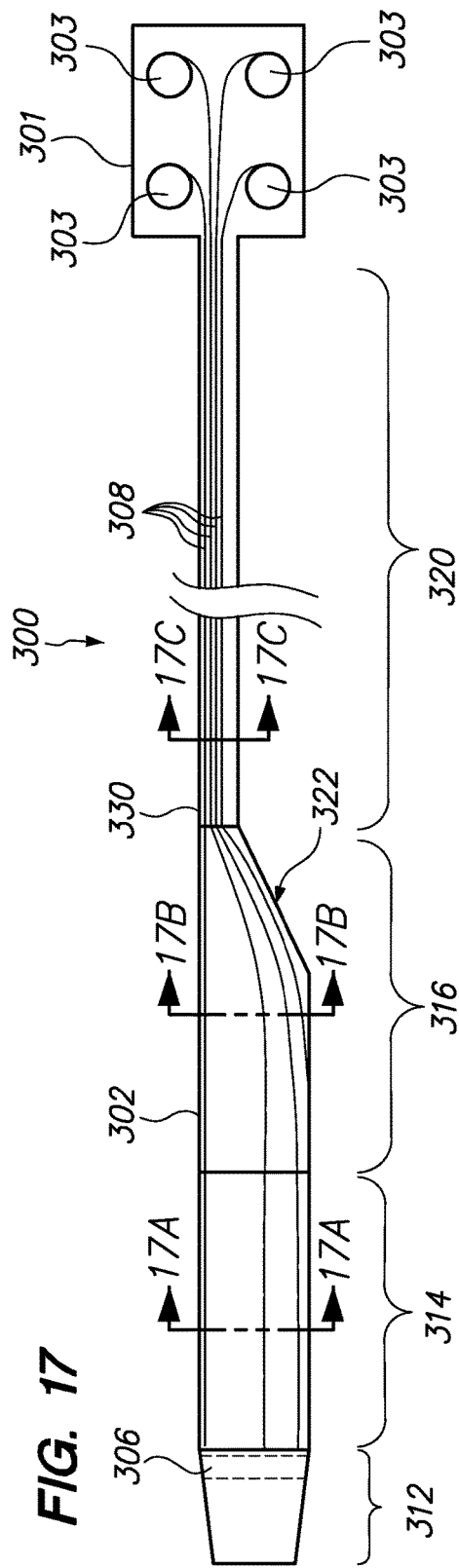
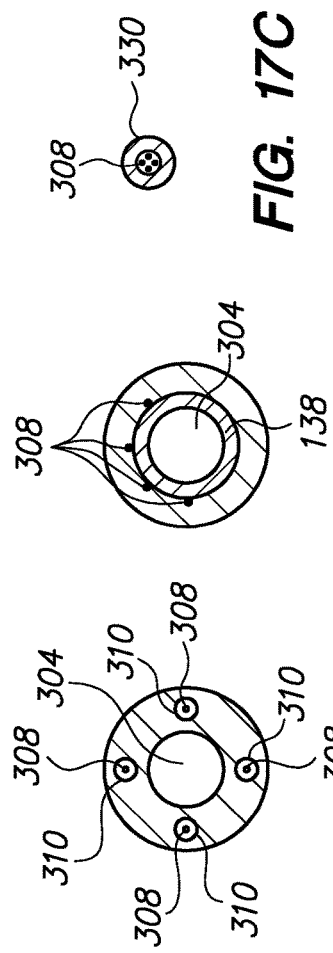
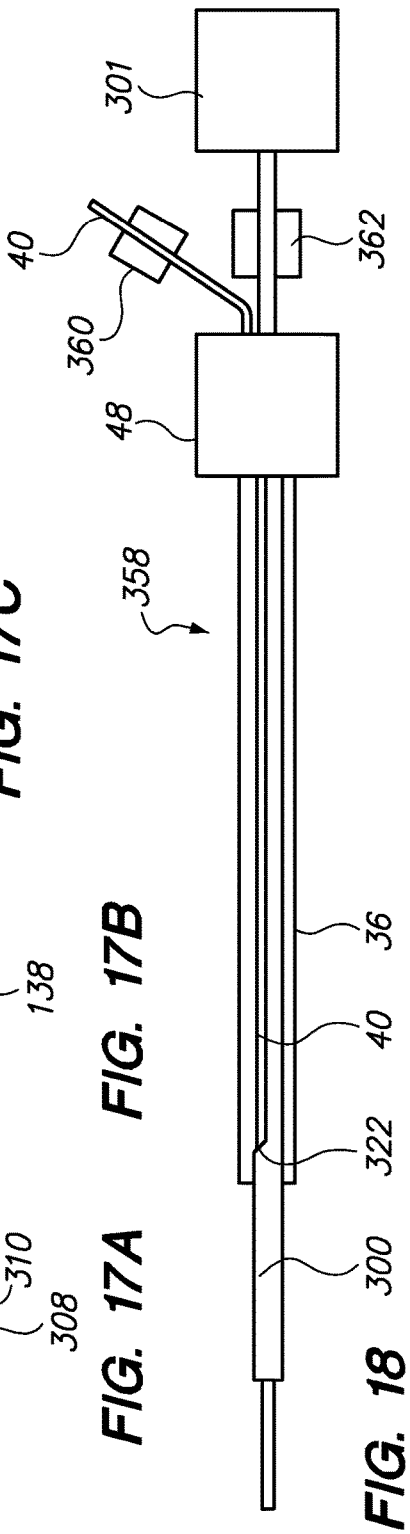

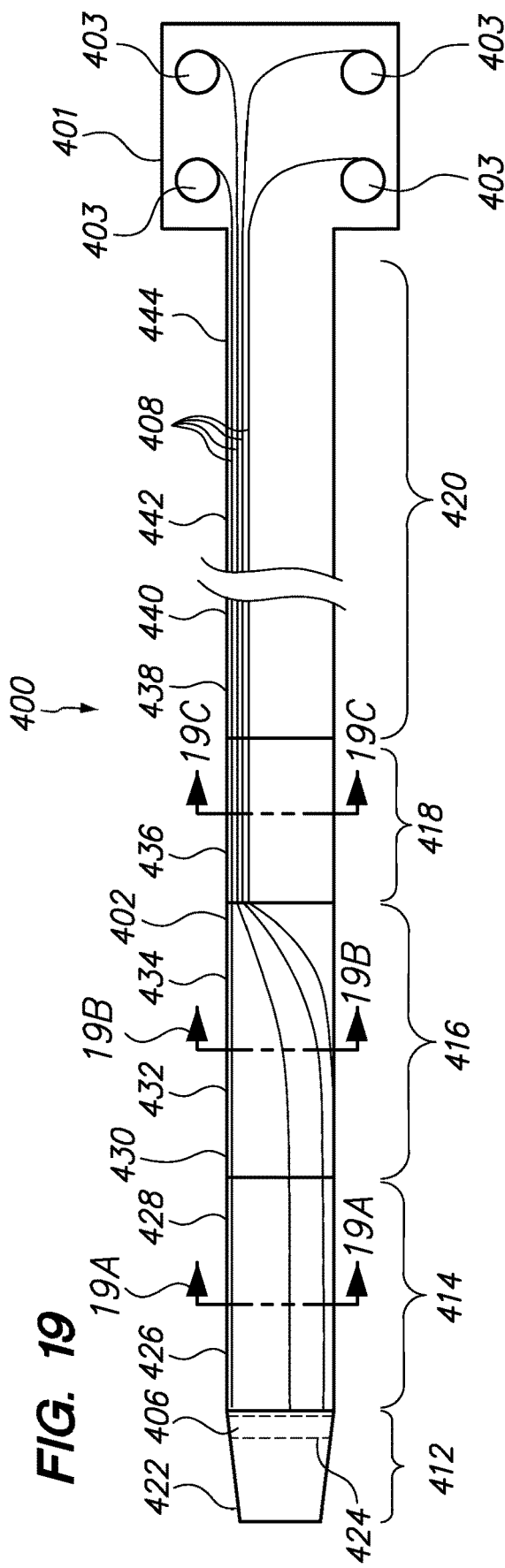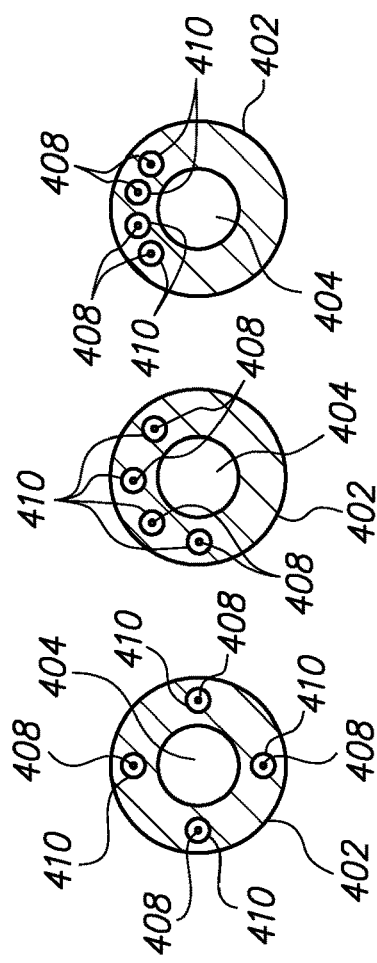
FIG. 19  FIG. 19A  FIG. 19B  FIG. 19C

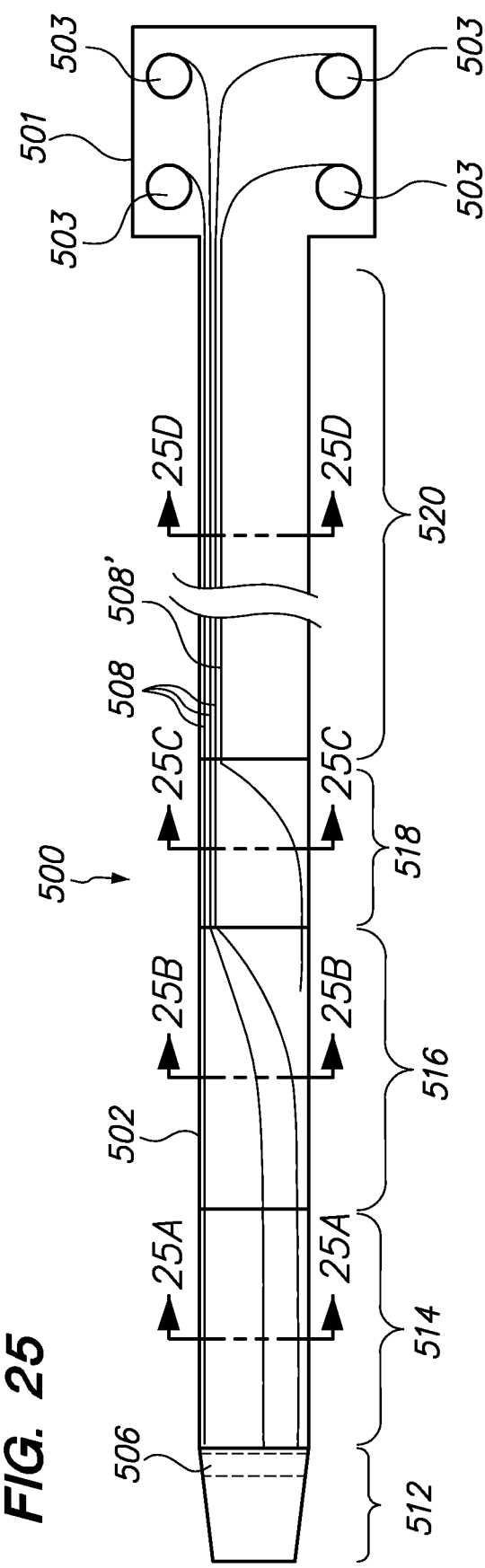
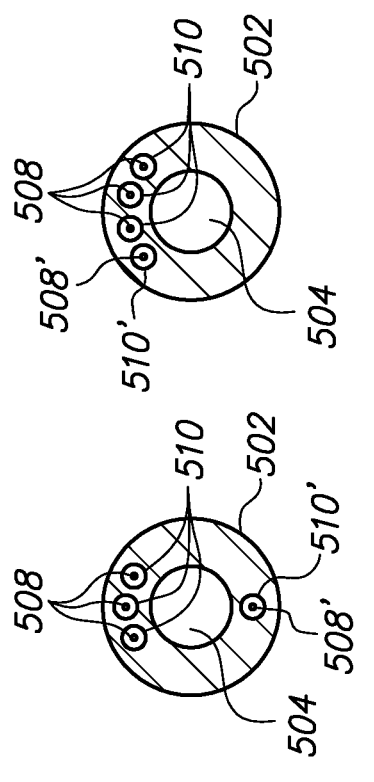
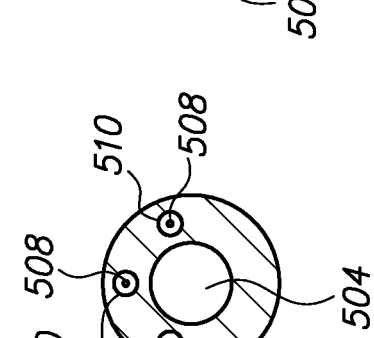
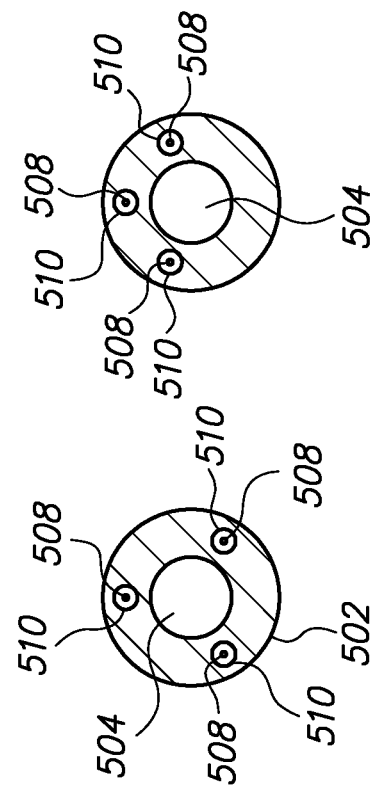

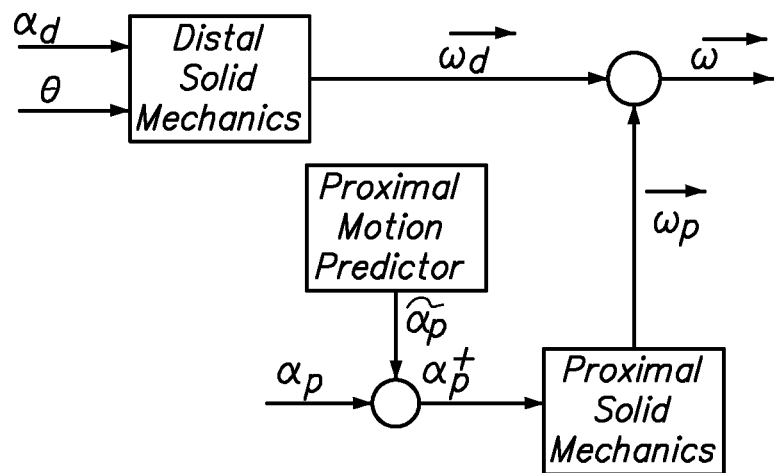
FIG. 28
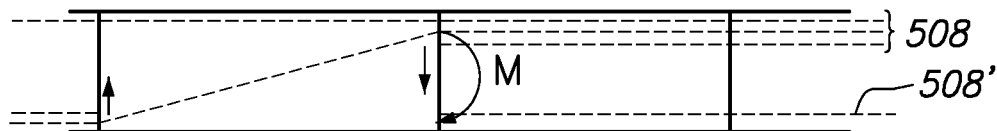
FIG. 29
FIG. 30A
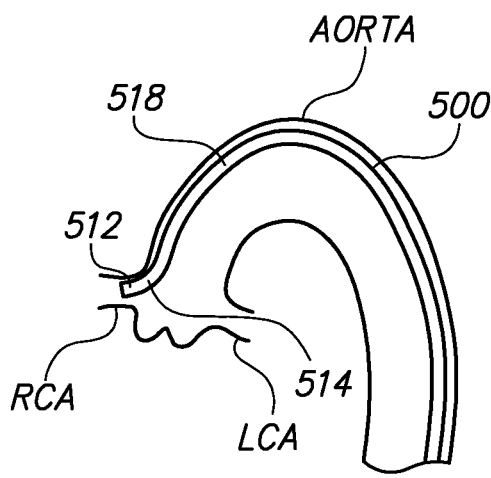
FIG. 30B
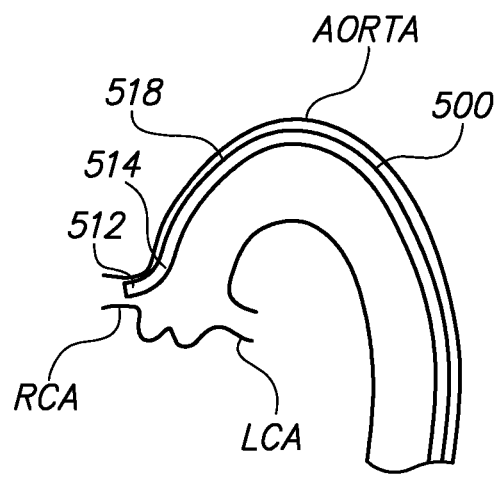

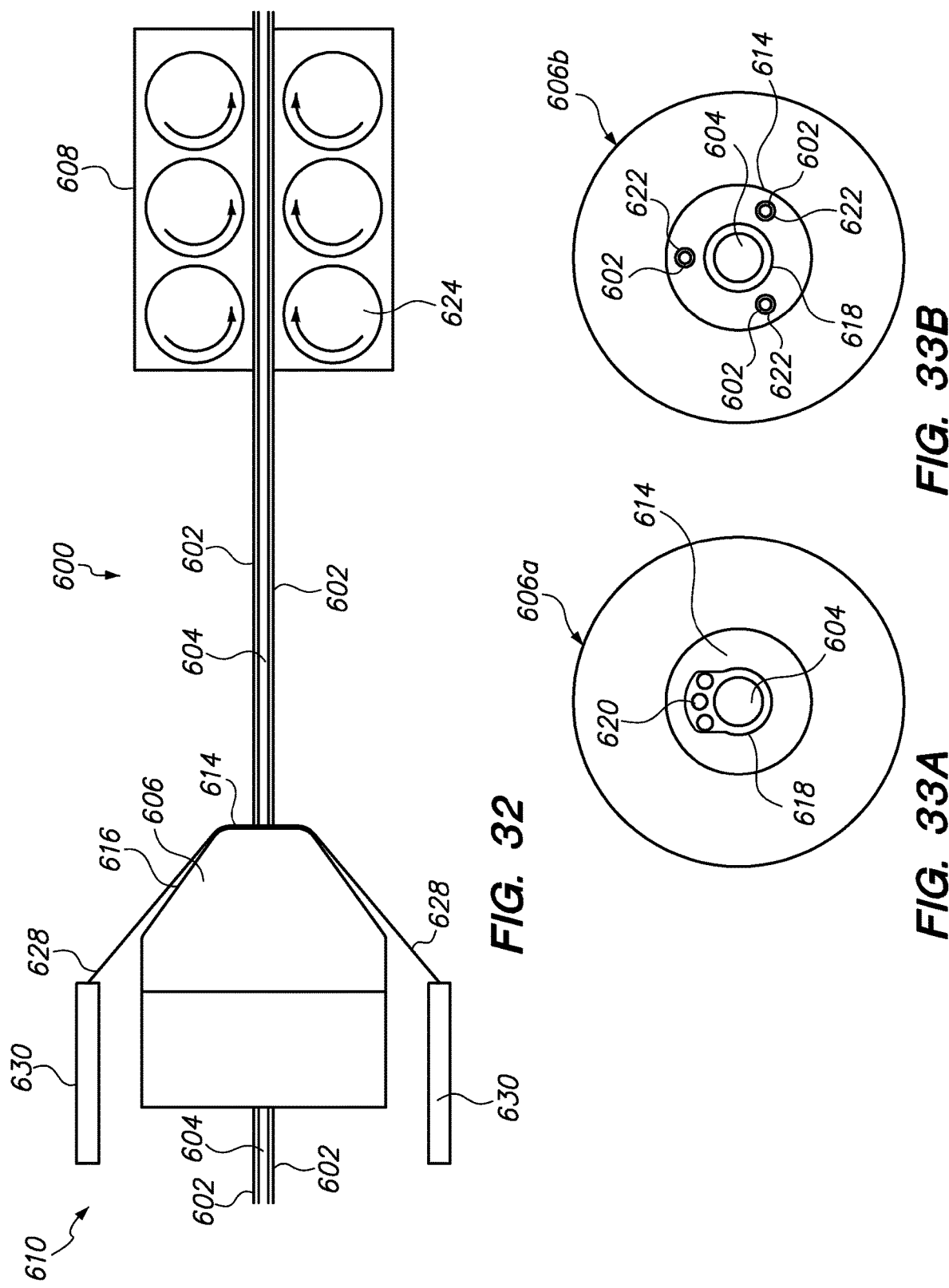

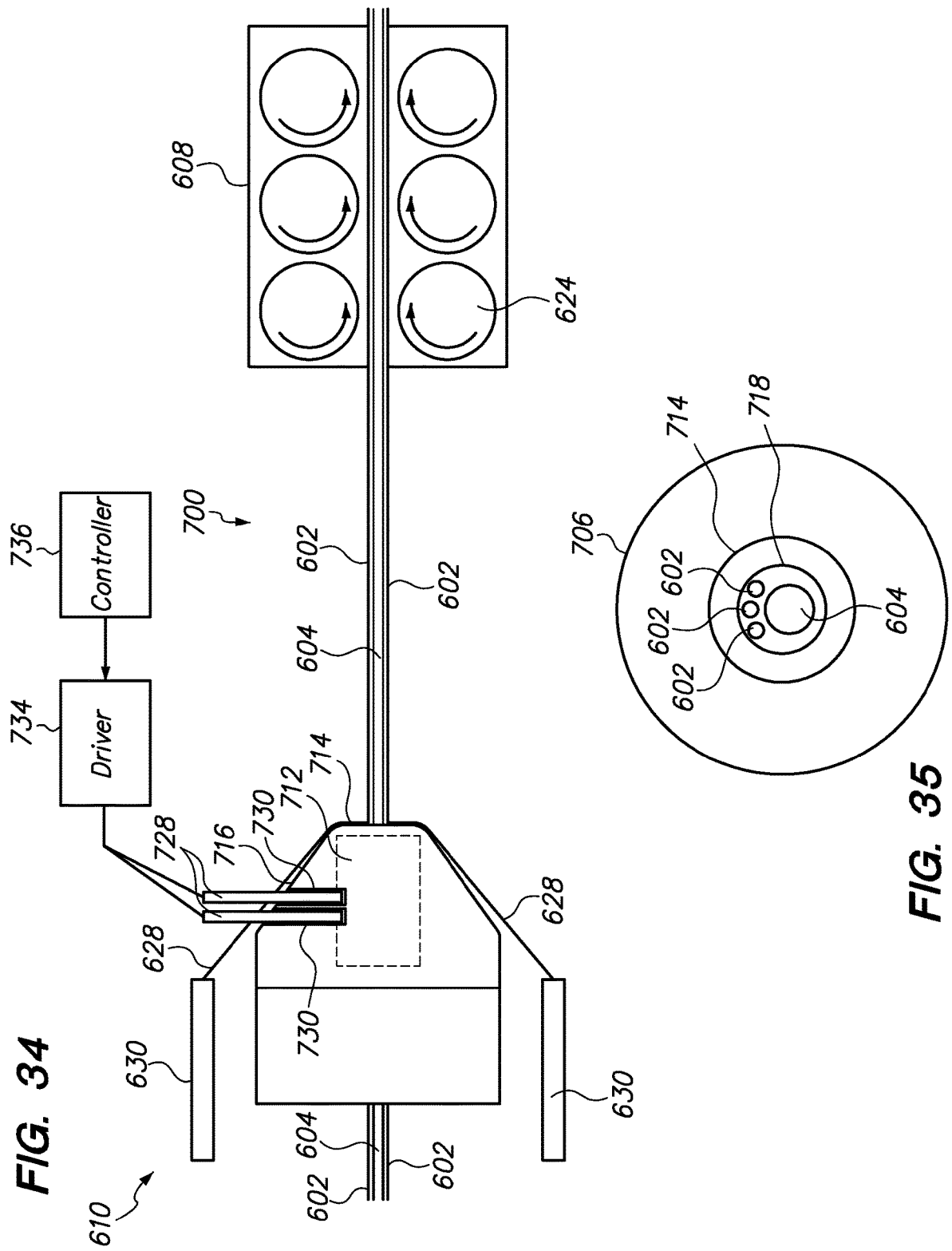

METHOD OF ANCHORING PULLWIRE DIRECTLY ARTICULATABLE REGION IN CATHETER

CROSS-REFERENCE TO RELATED APPLICATIONS

The present application is a continuation of U.S. patent application Ser. No. 13/687,294, filed on Nov. 28, 2012, entitled "METHOD OF ANCHORING PULLWIRE DIRECTLY ARTICULATABLE REGION IN CATHETER", the contents of which are incorporated herein by reference as though set forth in full.

FIELD OF INVENTION

The invention relates generally to minimally-invasive instruments and systems, such as manually or robotically steerable catheter systems, and more particularly to steerable catheter systems for performing minimally invasive diagnostic and therapeutic procedures.

BACKGROUND

Minimally invasive procedures are preferred over conventional techniques wherein the patient's body cavity is open to permit the surgeon's hands access to internal organs. Thus, there is a need for a highly controllable yet minimally sized system to facilitate imaging, diagnosis, and treatment of tissues which may lie deep within a patient, and which may be accessed via naturally-occurring pathways, such as blood vessels, other lumens, via surgically-created wounds of minimized size, or combinations thereof.

Currently known minimally invasive procedures for the treatment of cardiac, vascular, and other disease conditions use manually or robotically actuated instruments, which may be inserted transcutaneously into body spaces such as the thorax or peritoneum, transcutaneously or percutaneously into lumens such as the blood vessels, through natural orifices and/or lumens such as the mouth and/or upper gastrointestinal tract, etc. Manually and robotically-navigated interventional systems and devices, such as steerable catheters, are well suited for performing a variety of minimally invasive procedures. Manually-navigated catheters generally have one or more handles extending from their proximal end with which the operator may steer the pertinent instrument. Robotically-navigated catheters may have a proximal interface configured to interface with a catheter driver comprising, for example, one or more motors configured to induce navigation of the catheter in response to computer-based automation commands input by the operator at a master input device in the form of a work station.

In the field of electrophysiology, robotic catheter navigation systems, such as the Sensei® Robotic Catheter System (manufactured by Hansen Medical, Inc.), have helped clinicians gain more catheter control that accurately translates the clinician's hand motions at the workstation to the catheter inside the patient's heart, reduce overall procedures (which can last up to four hours), and reduce radiation exposure due to fluoroscopic imaging necessary to observe the catheter relative to the patient anatomy, and in the case of electrophysiology, within the relevant chamber in the heart. The Sensei® Robotic Catheter System employs a steerable outer catheter and a steerable inner electrophysiology (EP) catheter, which can be manually introduced into the patient's heart in a conventional manner. The outer and inner catheters are arranged in an "over the wire" telescoping arrangement that work together to advance through the tortuous anatomy of the patient. The outer catheter, often referred to as a guiding sheath, provides a steerable pathway for the inner catheter. Proximal adapters on the outer guide sheath and inner EP catheter can then be connected to the catheter driver, after which the distal ends of the outer sheath and inner EP catheter can be robotically manipulated in the heart chamber within six degrees of freedom (axial, roll, and pitch for each) via operation of the Sensei® Robotic Catheter System.

While the Sensei® Robotic Catheter System is quite useful in performing robotic manipulations at the operational site of the patient, it is desirable to employ robotic catheter systems capable of allowing a physician to access various target sites within the human vascular system. In contrast to the Sensei® Robotic Catheter System, which is designed to perform robotic manipulations within open space (i.e., within a chamber of the heart) after the outer guide sheath and inner catheter are manually delivered into the heart via a relatively non-tortuous anatomical route (e.g., via the vena cava), and therefore may be used in conjunction with sheaths and catheters that are both axially and laterally rigid, robotic catheter systems designed to facilitate access to the desired target sites in the human vascular system require simultaneous articulation of the distal tip with continued insertion or refraction of an outer guide sheath and an inner catheter. As such, the outer guide sheath and inner catheter should be laterally flexible, but axially rigid to resist the high axial loads being applied to articulate the outer guide sheath or inner catheter, in order to track through the tortuous anatomy of the patient. In this scenario, the inner catheter, sometimes called the leader catheter extends beyond the outer sheath and is used to control and bend a guide wire that runs all the way through the leader catheter in an over-the-wire configuration. The inner catheter also works in conjunction with the outer guide sheath and guide wire in a telescoping motion to inchworm the catheter system through the tortuous anatomy. Once the guide wire has been positioned beyond the target anatomical location, the leader catheter is usually removed so that a therapeutic device can be passed through the steerable sheath and manually operated.

Increasing the lateral flexibility of the sheath and catheter, however, introduces catheter navigation problems that may not otherwise occur when the sheath and catheter are laterally stiff. For example, many steerable catheters available today rely on the capability of the user to articulate the distal end of the catheter to a desired anatomical target. The predominant method for articulating the distal end of a catheter is to circumferentially space a multitude of free floating pullwires (e.g., four pullwires) into the wall of the catheter and attach them to a control ring embedded in the distal end of the catheter. The anchoring of each pullwire to the control ring is usually performed by soldering, welding, brazing, or gluing the pullwire to the control ring. If four pullwires are provided, the pullwires may be orthogonally spaced from each other. Each of these pullwires are offset from the center line of the catheter, and so when the wires are tensioned to steer the catheter tip, the resulting compressive forces cause the distal tip of the catheter to articulate in the direction of the pullwire that is tensioned. However, the compressive forces on the relatively flexible catheter shaft also cause undesired effects.

For example, the axial compression on the catheter shaft during a steering maneuver that bends the distal end of the catheter may cause undesired lateral deflection in the catheter shaft, thereby rendering the catheter mechanically unstable.

As another example, the curvature of the catheter shaft may make the articulation performance of the catheter unrepeatable and inconsistent. In particular, because the pullwires are offset from the neutral axis of the catheter shaft, bending the catheter shaft will tighten the pullwires on the outside of the curve, while slackening the pullwires on the inside of the curve. As a result, the amount of tension that should be applied to the pullwires in order to effect the desired articulation of the catheter distal end will vary in accordance with the amount of curvature that is already applied to the catheter.

As still another example, when bent, the articulate catheter distal end will tend to curve align with the catheter shaft. In particular, as shown in FIGS. 1A and 1B, operating or tensioning a pullwire on the outside edge of a bend may cause the catheter to rotate or twist as the pullwire may tend to rotate the distal articulating section of the catheter until the pullwire is at the inside edge of the bend. This rotation or twist phenomenon or occurrence is known as curve alignment.

That is, when the proximal shaft section of the catheter is curved (as it tracked through curved anatomy), and the distal section is required to be articulated in a direction that is not aligned with the curvature in the shaft, a wire on the outside of the bend is pulled, as shown in FIG. 1A. A torsional load (T) is applied to shaft as tension increases on the pull-wire on the outside of the bend. This torsional load rotates the shaft until the wire being pulled is on the inside of the bend, as shown in FIG. 1B. In effect, the tensioned wire on the outside of the bend will take the path of least resistance, which may often be to rotate the shaft to the inside of the bend rather than articulate the tip of the catheter adequately.

This un-intentional rotation of the shaft causes instability of the catheter tip and prevents the physician from being able to articulate the catheter tip in the direction shown in FIG. 1A. That is, no matter which direction the catheter tip is intended to be bent, it will ultimately bend in the direction of the proximal curve. The phenomenon is known as curve alignment because the wire that is under tension is putting a compressive force on both the proximal and distal sections and so both the proximal and distal curvature will attempt to align in order to achieve lowest energy state. The operator may attempt to roll the entire catheter from the proximal end in order to place the articulated distal tip in the desired direction. However, this will placed the tensioned inside pullwire to the outside of the proximal bend causing further tensioning of the pullwire, and possibly causing the distal end of the catheter to whip around.

All of these mechanical challenges contribute to the instability and poor control of the catheter tip, as well as increased catheter tracking forces. Some steerable catheters overcome these problems by increasing the axial stiffness of the entire catheter shaft (e.g., by varying wall thickness, material durometer, or changing braid configuration) or alternatively by incorporating axially stiff members within the catheter shaft to take the axial load. But these changes will also laterally stiffen the catheter shaft, thereby causing further difficulties in tracking the catheter through the vasculature of the patient. Therefore, the catheter designer is faced with having to make a compromise between articulation performance and shaft tracking performance. Other steerable catheters overcome this problem by using free floating coil pipes in the wall of the catheter to respectively housing the pullwires (as described in U.S. patent application Ser. No. 13/173,994, now issued as U.S. Pat. No. 8,827,948, entitled "Steerable Catheter", which is expressly incorporated herein by reference), thereby isolating the articulation loads from the catheter shaft. However, the use of coil pipes adds to the cost of the catheter and takes up more space in the result, resulting in a thicker catheter wall. Furthermore, because the relatively stiff coil pipes are spaced away from the neutral axis of the catheter, its lateral stiffness may be unduly increased.

There, thus remains a need to provide a different means for minimizing the above-described mechanical challenges in a laterally flexible, but axially rigid, catheter.

Furthermore, although a single region of articulation is typically sufficient to allow a user to track and steer the catheter though the vasculature, it is sometimes inadequate for tortuous anatomies, navigation of larger vessels, or for providing stability during therapy deployment.

For example, it may be desirable to access either the right coronary artery or the left coronary artery from the aorta of the patient in order to remove a stenosis in the artery by, e.g., atherectomy, angioplasty, or drug delivery. The proximal curve of a catheter may be pre-shaped in a manner that locates the distal end of the catheter in an optimal orientation to access the ostium of the right coronary artery via the aorta, as shown in FIG. 2A. However, in the case where it is desirable to access the ostium of the left coronary artery, the proximal curve of the catheter locates the distal end of the catheter too far from the left coronary artery, which therefore cannot be easily accessed via manipulation of the distal end of the catheter, as shown in FIG. 2B. Alternatively, the proximal curve of a catheter may be pre-shaped in a manner that locates the distal end of the catheter in an optimal orientation to access the ostium of the left coronary artery via the aorta, as shown in FIG. 2C. However, in the case where it is desirable to access the ostium of the left coronary artery, the proximal curve of the catheter locates the distal end of the catheter too close to the right coronary artery, such that the distal end would be seated too deeply within the ostium of the right coronary artery, as shown in FIG. 2D. Thus, it can be appreciated that multiple catheters may have to be used to treat both the left coronary artery and right coronary artery, thereby increasing the cost and time for the procedure.

To complicate matters even further, the articulating distal end of the catheter needs to be long enough to cross the aorta from the patient right side to the left coronary artery. However, there are varying anatomies in the population with respect to the positioning of the left coronary artery in the aorta. For example, FIG. 3A illustrates the proximal curve required for a catheter to place the distal end within the ostium of the left coronary artery in a "normal" anatomy; FIG. 3B illustrates the proximal curve required for a catheter to place the distal end within the ostium of the left coronary artery in a "wide" anatomy; and FIG. 3C illustrates the proximal curve required for a catheter to place the distal end within the ostium of the left coronary artery in an "unfolded" anatomy. It can be appreciated that, even if is desired to only treat the left coronary artery, the clinician may have to be supplied with multiple catheters, one of which can only be used for the particular anatomy of the patient.

One way to address this problem in conventional catheters is to have multiple unique or independent regions of articulation in the catheter shaft by, e.g., adding a control ring and a set of pullwires for each articulation region. Thus, both a proximal region and a distal region of the catheter can be articulated. When manufacturing a catheter within only a single region of articulation, this task is not overly complex, typically requiring a single lamination of a polymer extrusion to form an outer jacket over an inner polymer tube (or liner) and the installation of the control ring with associated pullwires onto the assembly. A braided material can be installed between the inner polymer tube and outer polymer jacket to provide select region of the catheter with increased rigidity.

However, when manufacturing a catheter that has two regions of articulation, this task can be difficult and usually requires the lamination of an outer polymer jacket extrusion up to the proximal articulation region, then the installation of the most proximal control ring with attached pullwires, and then the lamination of an outer polymer jacket for the remaining portion of the catheter. For catheters with more than two regions of articulation, this process would have to be repeated for each and every additional region of articulation. Another issue with respect to the use of control rings is that the laminated polymer extrusion or extrusions need to be carefully sized at the control ring, since the ring itself consumes volume in the wall that not only requires thinner extrusions so as to not have a bulge in the catheter at the control ring, but also creates a significantly stiffer region the length of the control ring, which causes a "knuckle" where there should be a gradual stiffness change required to achieve good catheter performance during tracking through the vasculature.

There, thus, remains a need to provide a more efficient means for anchoring the distal ends of the pullwires at the articulating region or regions of a catheter.

As briefly mentioned above, the inner catheter and guide wire may be arranged in an "over-the-wire" configuration. However, such a configuration requires the guide wire to be at least twice as long as the inner catheter in order to allow the user to continuously hold the guide wire in place as the inner catheter is removed from the outer guide sheath. For example, the inner catheter can have a length up to 160 cm, with 140 cm of the catheter being inside the patient. Therefore, to ensure that the position of the guide wire is maintained, the physician will typically require a guide wire to be over 300 cm long. However, guide wires longer than 300 cm are not readily available in sterile catheter laboratories. Additionally, long guide wires require an extra assistant at the bedside to manage the guide wire and ensure it remains in a fixed position and always remains sterile. Furthermore, such a configuration disadvantageously increases the length of the robot required to axially displace the guide wire within the inner catheter to the fullest extent. The increased size of the robot may be impractical and too big and heavy to be mounted on a table in a catheter lab environment. Additionally, because the inner catheter passes entirely "over-the-wire," the inner catheter cannot be robotically removed while holding the guide wire in place. Instead, the physician needs to remove the guide wire from the robot, and then slide the inner catheter proximally while holding the position of the guide wire fixed. The procedure time for removing the inner catheter from the outer guide sheath is increased for an over-the wire configuration (typically greater than one minute), thereby increasing fluoroscopic time and radiation exposure to the physician and staff.

A "rapid exchange" leader catheter would alleviate these concerns. Rapid exchange catheter designs have been described and documented in balloon angioplasty catheters, filters, and stent delivery system applications. These designs provide a rapid exchange port on the distal portion of the catheter shaft, which allows the guide wire to exit and run parallel to the proximal portion of the catheter shaft. However, no known designs exist for rapid exchange steerable catheters due to the challenge of navigating the pullwires proximal of the exit port. In addition, no known designs exist for the robotic interface for rapid exchange catheters.

There, thus, remains a need to provide the inner steerable catheter of a telescoping catheter assembly with a rapid exchange architecture.

SUMMARY OF THE INVENTION

In accordance with one aspect of the present inventions, a catheter comprises a flexible polymer catheter body including a proximal shaft section and a distal working section. The cross-sectional shape of the catheter body may be any suitable shape, such as circular or rectangular. The catheter may optionally comprise a lumen extending through the catheter body. The catheter further comprises a wire support structure (e.g., a braided tubular structure or a coiled structure) embedded within the distal working section of the catheter body, and a proximal adapter mounted to the proximal shaft section of the catheter body. The catheter further comprises a wire disposed within the catheter body. The wire has a proximal end operably connected to the proximal adapter, and a distal end anchored to the wire support structure. The wire support structure comprises a plurality of tubular layers, in which case, the distal end of the wire may be anchored between the tubular layers of the wire support structure.

In one embodiment, the catheter further comprises a lumen disposed within the catheter body, in which case, the wire is a pullwire extending through the lumen, the distal working section of the catheter body is a distal articulatable section, and the proximal adapter is a proximal steerable interface that is manipulatable to selectively tension the pullwire to bend the distal articulating section. In another embodiment, the catheter further comprises an electrode mounted to the distal working section of the catheter body, in which case, the wire is an electrical wire, the distal end of which is electrically coupled to the electrode.

In accordance with another aspect of the present inventions, a method of constructing a catheter comprises disposing a wire support structure over an inner polymer tube (e.g., one having a lumen extending therethrough). The wire support structure may be disposed on the inner polymer tube by braiding filament onto the inner polymer tube. The method further comprises disposing at least one outer polymer tube over the wire support structure and wire, applying heat to the melt the outer polymer tube(s), thereby flowing the melted outer polymer tube(s) into the wire support structure. The method further comprises allowing the melted outer polymer tube(s) to solidify, thereby integrating the wire support structure, inner polymer tube, and solidified outer polymer tube(s) together into a catheter body, disposing a wire through the catheter body, and anchoring (e.g., soldering, welding, brazing, or gluing) a distal end of the wire to the wire support structure at a distal end of the catheter body. In one method, the wire support structure comprises a plurality of tubular layers, in which case, the distal end of the wire may be anchored between the tubular layers of the wire support structure. The method may further comprise mounting a proximal adapter to a proximal end of the catheter body, and operatively coupling a proximal end of the wire to the proximal adapter.

An optional method may comprise disposing a barrier over the wire support structure prior to melting the outer tube(s), with the melting temperature of the barrier being greater than the temperature of the heat applied to the outer polymer tube(s). This method may further comprise removing the barrier from the catheter body subsequent to allowing the melted outer tube(s) to solidify, thereby exposing a portion of the wire support structure. In this case, the distal end of the wire is anchored to the exposed portion of the wire support structure. The barrier may be a tubular barrier, in which case, the exposed portion of the wire support structure may be cylindrical. The optional method may further comprise disposing another outer polymer tube over the exposed cylindrical portion of the wire support structure, melting the other polymer tube, thereby flowing the other outer polymer tube into the exposed cylindrical portion of the wire support structure, and allowing the other melted outer polymer tube to solidify.

Another method further comprises forming a lumen within the catheter body, the wire is a pullwire extending through the lumen, and the proximal adapter is a proximal steerable interface. In this case, forming the lumen in the catheter body may comprise disposing a process mandrel over the inner polymer tube prior to melting the at least one outer tube, and removing the process mandrel from the catheter body subsequent to allowing the melted outer tube(s) to solidify, and disposing the wire through the catheter body may comprise threading the wire through the lumen.

In still another method, the wire is an electrical wire, and the method further comprises forming an electrode to the catheter body in electrical communication with the wire. In this case, forming the electrode on the catheter body may comprise disposing a barrier over the wire support structure prior to melting the outer tube(s), removing the barrier from the catheter body subsequent to allowing the melted outer tube(s) to solidify, thereby exposing a portion of the wire support structure, and disposing the electrode on the exposed portion of the wire support structure.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of various embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 7 is a plan view of one catheter having a single region of articulation with four pullwires for use in the catheter assembly of FIG. 6;

FIGS. 7A-7C are cross-sectional views of the catheter of FIG. 7, respectively taken along the lines 7A-7A, 7B-7B, and 7C-7C;

FIG. 13 is a plan view of one catheter having a single region of articulation with three pullwires for use in the catheter assembly of FIG. 6;

FIGS. 13A-13C are cross-sectional views of the catheter of FIG. 13, respectively taken along the lines 13A-13A, 13B-13B, and 13C-13C;

FIG. 17 is a plan view of a rapid exchange catheter having a single region of articulation with four pullwires for use in the catheter assembly of FIG. 18;

FIGS. 17A-17C are cross-sectional views of the catheter of FIG. 17, respectively taken along the lines 17A-17A, 17B-17B, and 17C-17C;

FIG. 18 is a side view of a rapid exchange catheter assembly that can alternatively be used in the robotic catheter assembly of FIG. 5;

FIG. 19 is a plan view of one catheter having two regions of articulation with four pullwires for use in the catheter assembly of FIG. 6;

FIGS. 19A-19C are cross-sectional views of the catheter of FIG. 19, respectively taken along the lines 19A-19A, 19B-19B, and 19C-19C;

FIG. 25 is a plan view of another catheter having two regions of articulation with four pullwires for use in the catheter assembly of FIG. 6;

FIGS. 25A-25D are cross-sectional views of the catheter of FIG. 25, respectively taken along the lines 25A-25A, 25B-25B, 25C-25C, and 25D-25D;

FIG. 28 is a control diagram illustrating a multi-bend algorithm that control the distal articulating section and proximal articulating section of the catheter of FIG. 25;

FIG. 29 is a diagram illustrating the moment applied to the transition section of the catheter of FIG. 25 caused by the pullwires extending through the transition section;

FIGS. 30A and 30B are plan views showing one method of accessing the right coronary artery of an anatomy using the catheter of FIG. 25;

FIG. 32 is a plan view illustrating one embodiment of a braiding machine that can be used to braid a catheter for use in the catheter assembly of FIG. 6;

FIGS. 33A and 33B are front views of interchangeable nose cones that can be used in the braiding machine of FIG. 32;

FIG. 34 is a plan view illustrating another embodiment of a braiding machine that can be used to braid a catheter for use in the catheter assembly of FIG. 6;

FIG. 35 is a front view of a nose cone that can be used in the braiding machine of FIG. 34;

DETAILED DESCRIPTION OF THE ILLUSTRATED EMBODIMENTS

Figure 1A:
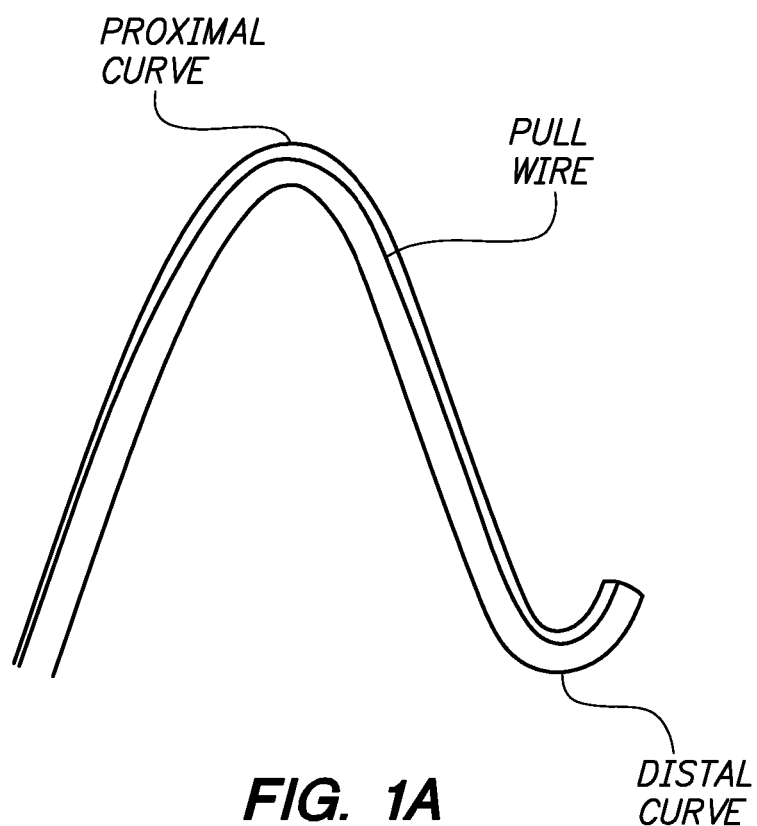
FIGS. 1A and 1B are plan views showing a curve alignment phenomenon that may occur when articulating a prior art steerable catheter.
Figure 1B:
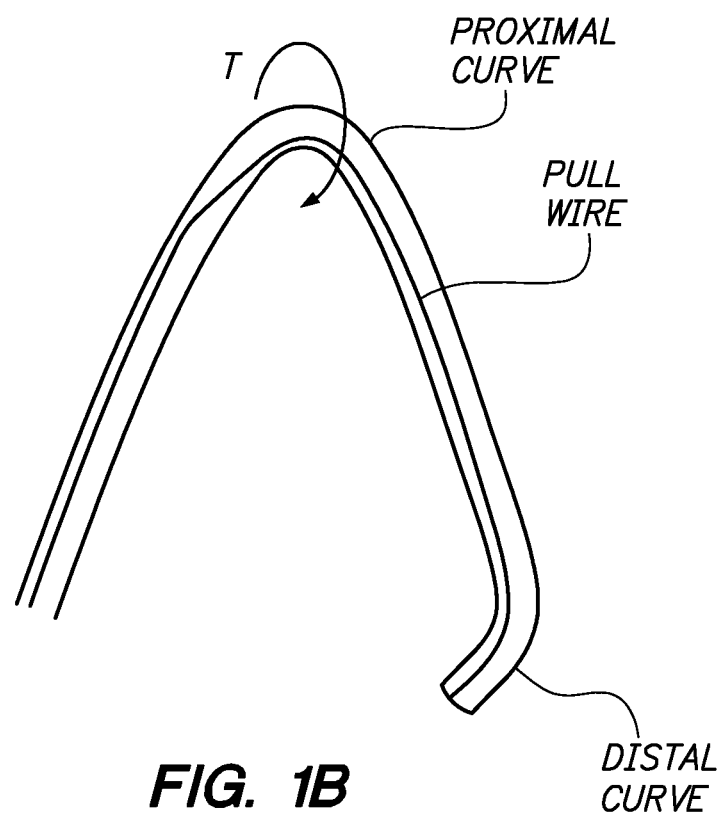
Figure 2A:
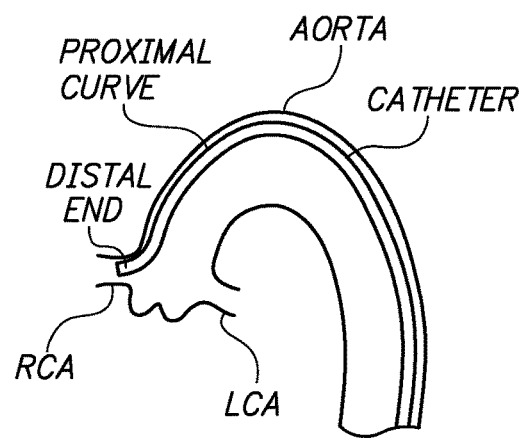
FIGS. 2A-2D are plan views showing possible issues related to using a prior art catheter having a single region of articulation for accessing both the left coronary artery and a right coronary artery of a patient's anatomy.
Figure 2B:
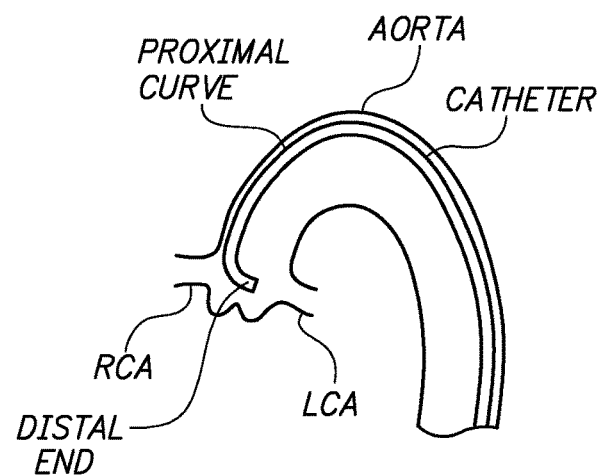
Figure 2C:
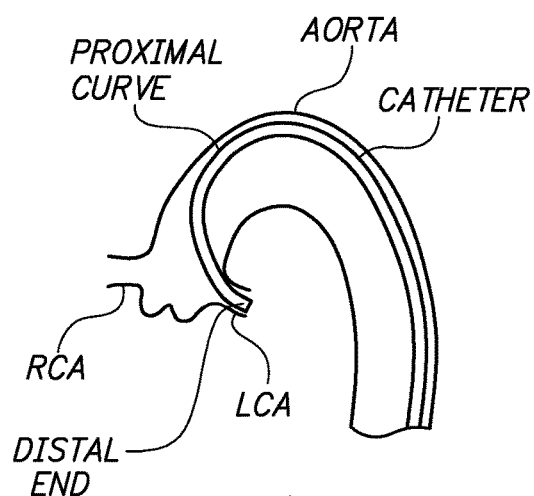
Figure 2D:
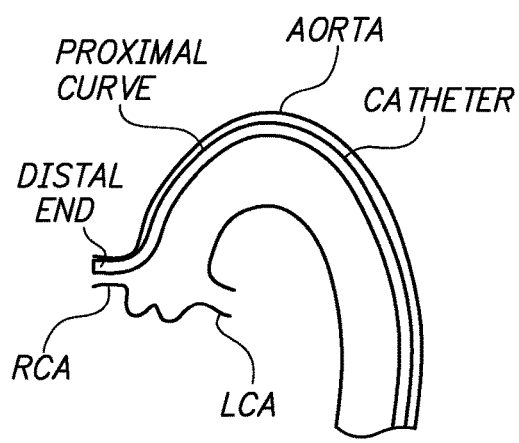
Figure 3A:
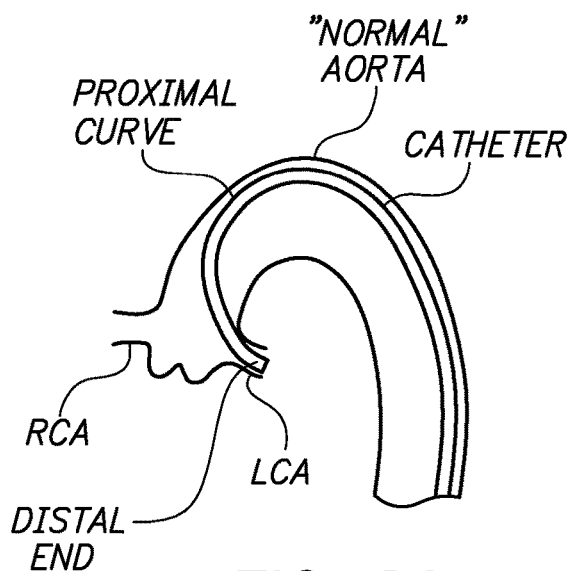
FIGS. 3A-3C are plan views showing possible issues related to using a prior art catheter having a single region of articulation for accessing different left coronary artery anatomies.
Figure 3B:
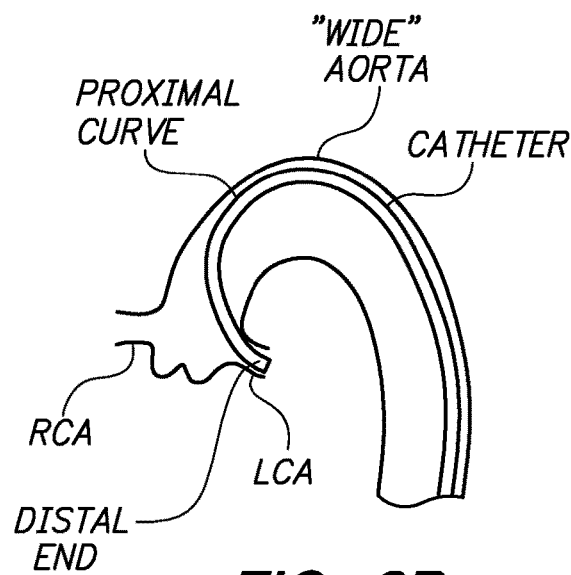
Figure 3C:
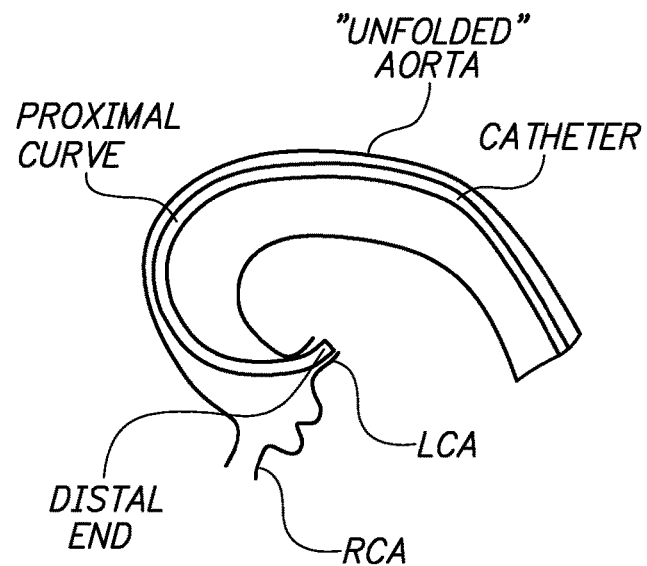
Figure 4:
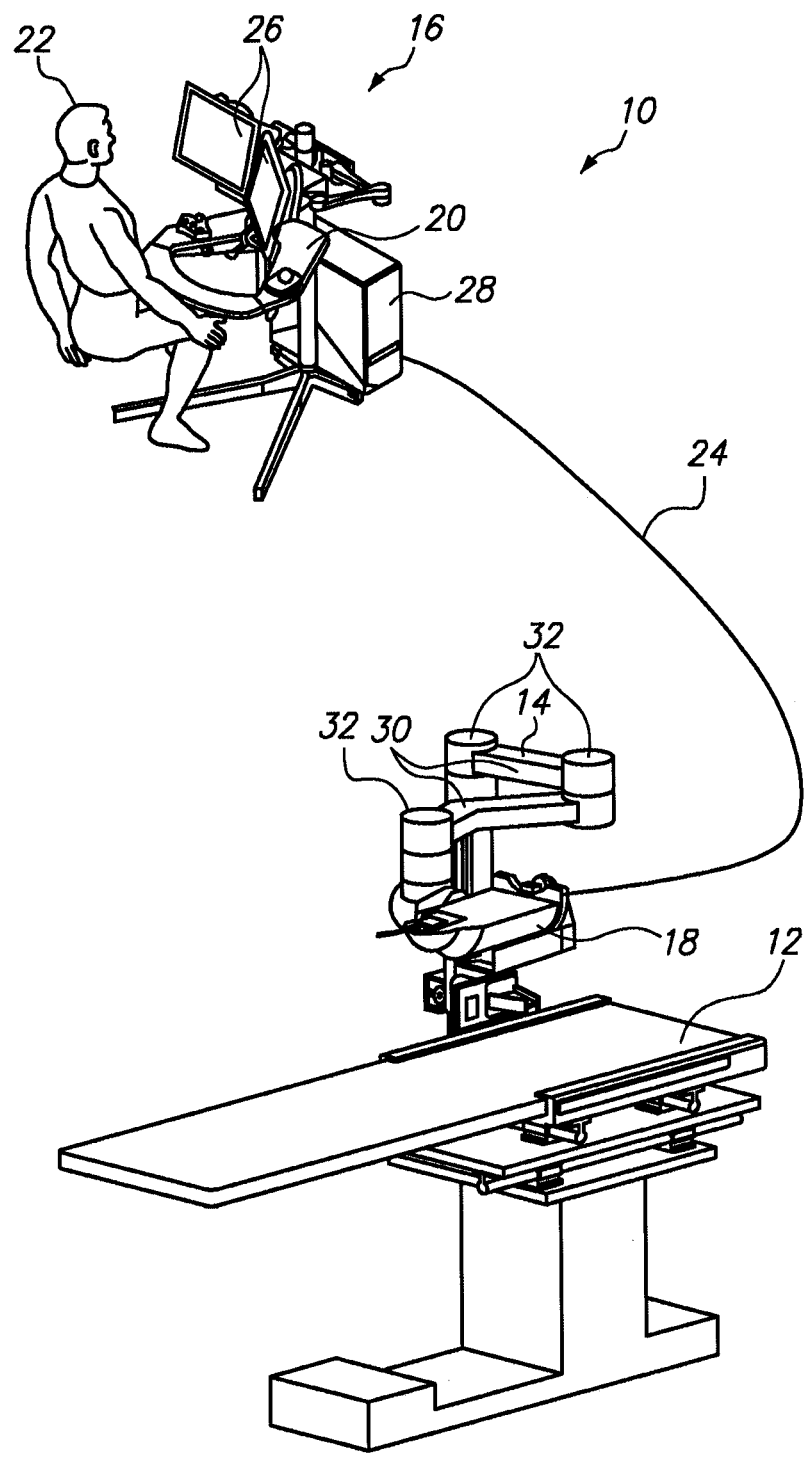
FIG. 4 is a perspective view of a medical robotic system constructed in accordance with one embodiment of the present inventions.

Referring to FIG. 4, one embodiment of a robotic catheter system 10 constructed in accordance with the present invention will now be described. The system 10 generally comprises an operating table 12 having a movable support-arm assembly 14, an operator control station 16 located remotely from the operating table 12, and a robotic catheter assembly 18 mounted to the support-arm assembly 14 above the operating table 12. Exemplary robotic catheter systems that may be modified for constructing and using embodiments of the present invention are disclosed in detail in the following U.S. Patent Applications, which are all expressly incorporated herein by reference in their entirety: U.S. patent application Ser. No. 11/678,001, filed Feb. 22, 2007 and issued as U.S. Pat. No. 8,092,397 on Jan. 10, 2012; U.S. patent application Ser. No. 11/073,363, filed Mar. 4, 2005 and issued as U.S. Pat. No. 7,972,298 on Jul. 5, 2011; U.S. patent application Ser. No. 11/179,007, filed Jul. 6, 2005 and issued as U.S. Pat. No. 7,850,642 on Dec. 14, 2010; U.S. patent application Ser. No. 11/418,398, filed May 3, 2006 and issued as U.S. Pat. No. 7,963,288 on Jun. 21, 2011; U.S. patent application Ser. No. 11/481,433, filed Jul. 3, 2006 and issued as U.S. Pat. No. 8,052,636 on Nov. 8, 2011; U.S. patent application Ser. No. 11/637,951, filed Dec. 11, 2006 and issued as U.S. Pat. No. 8,190,238 on May 29, 2012; U.S. patent application Ser. No. 11/640,099, filed Dec. 14, 2006 and issued as U.S. Pat. No. 8,498,691 on Jul. 30, 2013; U.S. Patent Application Ser. No. 60/833,624, filed Jul. 26, 2006; and U.S. Patent Application Ser. No. 60/835,592, filed Aug. 3, 2006.

The control station 16 comprises a master input device 20 that is operatively connected to the robotic catheter assembly 18. A physician or other user 22 may interact with the master input device 20 to operate the robotic catheter assembly 18 in a master-slave arrangement. The master input device 20 is connected to the robotic catheter assembly 18 via a cable 24 or the like, thereby providing one or more communication links capable of transferring signals between the control station 16 and the robotic catheter assembly 18. Alternatively, the master input device 20 may be located in a geographically remote location and communication is accomplished, at least in part, over a wide area network such as the Internet. The master input device 20 may also be connected to the robotic catheter assembly 18 via a local area network or even wireless network that is not located at a geographically remote location.

The control station 16 also comprises one or more monitors 26 used to display various aspects of the robotic instrument system 10. For example, an image of the sheath and leader catheter (described in further detail below) may be displayed in real time on the monitors 26 to provide the physician 22 with the current orientation of the various devices as they are positioned, for example, within a body lumen or region of interest. The control station 16 further comprises a processor in the form of a computer 28, which may comprise a personal computer or other type of computer work station for accurately coordinating and controlling actuations of various motors within robotic catheter assembly 18.

The support-arm assembly 14 is configured for movably supporting the robotic catheter assembly 18 above the operating table 12 to provide convenient access to the desired portions of the patient (not shown) and provide a means to lock the catheter assembly 18 into position subsequent to the preferred placement. In this embodiment, the support-arm assembly 14 comprises a series of rigid links 30 coupled by electronically braked joints 32, which prevent joint motion when unpowered, and allow joint motion when energized by the control station 16. In an alternative embodiment, the rigid links 30 may be coupled by more conventional mechanically lockable joints, which may be locked and unlocked manually using, for example, locking pins, screws, or clamps. The rigid links 30 preferably comprise a light but strong material, such as high-gage aluminum, shaped to withstand the stresses and strains associated with precisely maintaining three-dimensional position of the weight of the catheter assembly 18.

Figure 5:
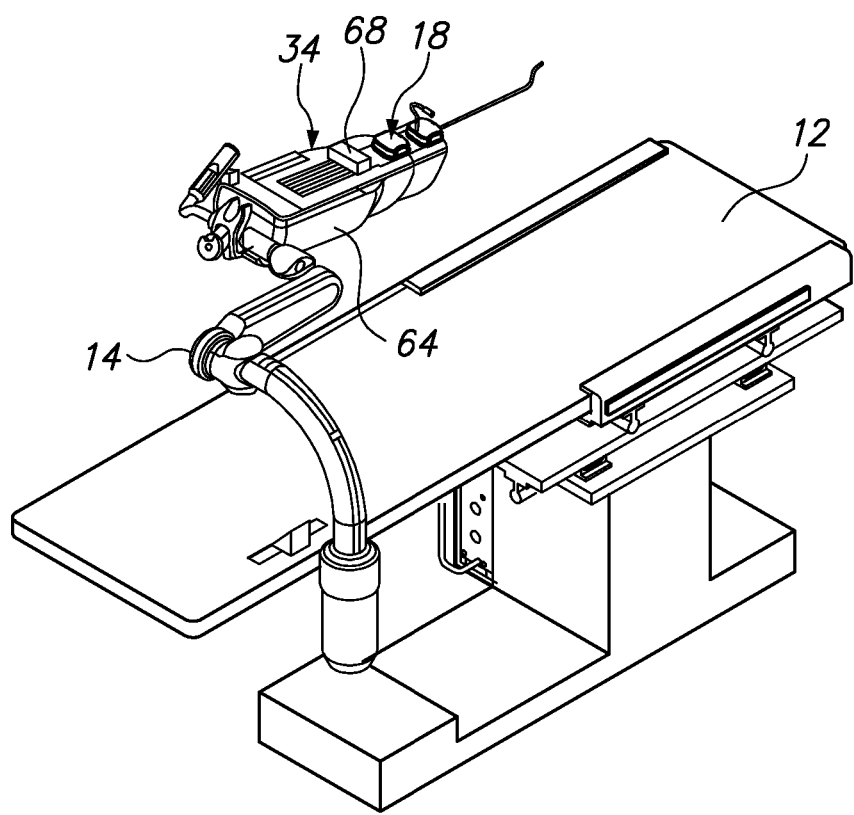
FIG. 5 is a perspective view of a robotic catheter assembly used in the medical robotic system of FIG. 4.
Figure 6:
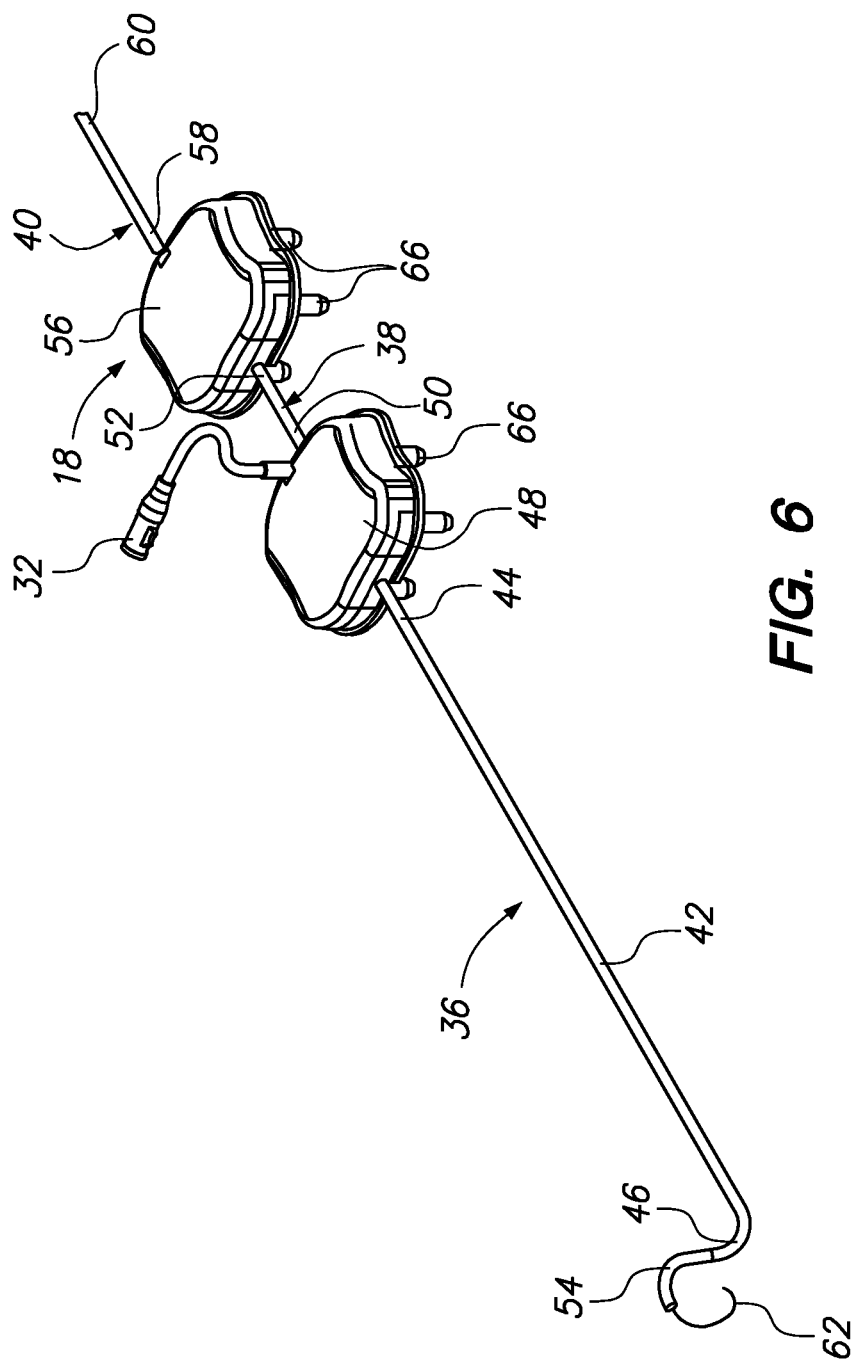
FIG. 6 is a perspective view of the catheter assembly used in the robotic catheter assembly of FIG. 5.

Referring further to FIGS. 5 and 6, the robotic catheter assembly 18 will now be described in detail. The robotic catheter assembly 18 comprises a robotic instrument driver 34, a robotic guide sheath 36, a robotic leader catheter 38, and a guide wire 40 mounted to the instrument driver 34 in a coaxial relationship. The robotic catheter assembly 18 may also include a drape (not shown) that covers the instrument driver 34. As will be described in further detail below, the instrument driver 34 provides robotic steering actuation, as well as robotic insertion and retraction actuation, to the guide sheath 36, working catheter 38, and guide wire 40 in accordance with control signals transmitted from the control station 16 (shown in FIG. 4). The guide sheath 36 generally includes a sheath body 42 having a proximal end 44 and a distal end 46, as well as a proximal interface in the form of a guide sheath steering adapter 48 ("splayer") operably coupled to the proximal end 44 of the sheath body 42. The leader catheter 38 generally includes a catheter body 50 having a proximal end 52 and a distal end 54, as well as a proximal interface in the form of a leader catheter steering adapter 56 operably mounted to the proximal end 52 of the catheter body 50. The guide wire 40 generally includes a guide wire body 58 having a proximal end 60 and a distal end 62.

The instrument driver 34 comprises a housing 64 that contains motors (not shown). The respective adapters 48, 56 and the proximal end 60 of the guide wire body 58 are mechanically interfaced to the housing 64 in such a manner that they may be axially displaced relative to each other via operation of the motors, thereby effecting insertion or retraction movements of the respective guide sheath 36, leader catheter 38, and guide wire 40 relative to each other, and thus, relative to the operating table 12 (shown in FIG. 4).

To this end, the guide sheath 36 comprises a working lumen (not shown in FIGS. 5 and 6) that extends all the way through the sheath body 42. The geometry and size of the working lumen will be selected in accordance with the cross-sectional geometry and size of the lead catheter 38. The sheath body 42 may be composed of a low-friction inner layer (e.g., a coating of silicone or polytetrafluoroethylene) to provide a low-friction surface to accommodate movement of the leader catheter 38 within the working lumen. The lead catheter 38 passes through the lumen of the guide sheath 36, and is thus, moveable relative thereto. As shown in FIGS. 5 and 6, the leader catheter 38 projects distally with respect to the distal end 46 of the sheath body 42. Of course, the leader catheter 38 may be withdrawn proximally such that its distal end 54 is substantially flush with the distal end 46 of the sheath body 42, or withdrawn proximally even further such that its distal end 54 is disposed within the distal end 46 of the sheath body 42. The leader catheter 38 may be movably positioned within the working lumen of the guide sheath 36 to enable relative insertion of the two devices, relative rotation, or "roll" of the two devices, and relative steering or bending of the two devices relative to each other, particularly when the distal end 54 of the leader catheter 38 is inserted beyond the distal tip of the guide sheath 36.

Similarly, the leader catheter 38 comprises a working lumen (not shown in FIGS. 5 and 6) that extends at least partially through the catheter body 50. The geometry and size of the working lumen will be selected in accordance with the cross-sectional geometry and size of the guide wire 40. The catheter body 50 may be composed of a low-friction inner layer (e.g., a coating of silicone or polytetrafluoroethylene) to provide a low-friction surface to accommodate movement of the guide wire 40 within the working lumen. The guide wire 40 passes through the lumen of the leader catheter 38, and is thus, moveable relative thereto. As shown in FIGS. 5 and 6, the guide wire 40 projects distally with respect to the distal end 54 of the catheter body 50. Of course, the guide wire 40 may be withdrawn proximally such that its distal end 62 is substantially flush with the distal end 54 of the catheter body 50, or withdrawn proximally even further such that its distal end 62 is disposed within the distal end 62 of the catheter body 50. The guide wire 40 may be movably positioned within the working lumen of the leader catheter 38 to enable relative insertion of the two devices, relative rotation, or "roll" of the two devices, and relative steering or bending of the two devices relative to each other, particularly when the distal end 62 of the guide wire 40 is inserted beyond the distal tip of the leader catheter 38. Notably, by movably positioning the guide wire 40 relative to the leader catheter 38, and movably positioning the leader catheter 38 relative to the guide sheath 36, the bending stiffness of the assembly may be varied as needed to optimize the tracking ability of the leader catheter 38.

Each of the adapters 48, 56 also comprises one or more rotating spools or drums 66 that can selectively tension or release pullwires (not shown in FIG. 6) disposed within the respective sheath body 42 and catheter body 50, thereby effecting a single articulation (and optionally, multiple articulations) of the distal ends 46, 54 of the sheath and catheter bodies 42, 50. In the illustrated embodiment, each of the adapters 48, 56 comprises four rotating spools or drums 66 (only one shown for the proximal adapter 48, and only three shown for the proximal adapter 56) for four corresponding pullwires. The instrument driver 34 further comprises a guide wire driver 68 to which the proximal end of the guide wire body 58 is affixed. The distal end 62 of the guide wire body 58 may have a J-shape as is conventional for guide wires. Each of the adapters 48, 56 and guide wire driver 68 may optionally be capable of rotating or rolling the sheath body 42, catheter body 50, and guide wire body 58 relative to each other.

With reference now to FIG. 7, an embodiment of a flexible and steerable elongate catheter 100 will be described. The catheter 100 can be used as either of the guide sheath 36 or leader catheter 38 illustrated in FIGS. 5 and 6, and can be operably coupled to the instrument driver 34 via a proximal adapter 101 (e.g., either of proximal adapters 48, 56). The catheter 100 is substantially pliable or flexible, such that when it is advanced into a patient, an operator or surgeon may easily manipulate the catheter 100 to conform, adopt, or match the shape or curvatures of the internal pathways (e.g., gastrointestinal tract, blood vessels, etc.) of the patient.

The catheter 100 generally includes an elongate catheter body 102, which in the illustrated embodiments, has a circular cross-section, although other cross-sectional geometries, such as rectangular, can be used. As will be described in further detail below, the catheter body 102 may be comprised of multiple layers of materials and/or multiple tube structures that exhibit a low bending stiffness, while providing a high axial stiffness along the neutral axis. Typical designs include a nitinol spine encapsulated in braid and any flexible, pliable, or suitable polymer material or bio-compatible polymer material or a braided plastic composite structure composed of low durometer plastics (e.g., nylon-12, Pebax®, polyurethanes, polyethylenes, etc.).

The catheter 100 further includes a working lumen 104 disposed through the entire length of the catheter body 102 for delivering one or more instruments or tools from the proximal end of the catheter body 102 to the distal end of the catheter body 102. The nature of the working lumen 104 will depend on the intended use of the catheter 100. For example, if the catheter 100 is to be used as the guide sheath 36 (shown in FIG. 6), the working lumen 104 will serve to accommodate the leader catheter or working catheter 38 (shown in FIG. 6). If the catheter 100 is to be used as a leader catheter or working catheter, the working lumen 104 will serve to accommodate a guide wire 40 (shown in FIG. 6).

To enable steering, the catheter 100 further includes a control ring 106 (shown in phantom) secured around the working lumen 104 at any location, section, portion, or region along the length of the catheter body 102, a plurality of pullwires 108 housed within one or more lumens 110 extending through the catheter body 102, and a proximal adapter (not shown). Each of pullwires 108 may be a metallic wire, cable or filament, or it may be a polymeric wire, cable or filament. The pullwire 108 may also be made of natural or organic materials or fibers. The pullwire 108 may be any type of suitable wire, cable or filament capable of supporting various kinds of loads without deformation, significant deformation, or breakage.

The distal ends of the pullwires 108 are anchored or mounted to the control ring 106, such that operation of the pullwires 108 may apply force or tension to the control ring 106, which may steer or articulate (e.g., up, down, pitch, yaw, or any direction in-between) the pertinent location, section, portion, or region of the catheter 100, which may in effect provide or define various bend radii for the articulated portion of the catheter 100. In the illustrated embodiment, the control ring 106 is secured to the distal end of the catheter 100, and therefore, the distal end of the catheter 100 will articulate when any of the pullwires 108 are tensioned. The proximal ends of the pullwires 108 terminate in the proximal adapter 101, and in particular, spools or drums 103 located within the proximal adapter 101. Thus, robotic or manual actuation of the proximal interface will cause the pertinent location, section, portion, or region of the catheter 100 to articulate in the direction of the pullwire or pullwires 108 that are tensioned. The catheter 100 may alternatively be manually controlled, in which case, it may include a conventional manually controlled steerable interface (not shown).

In other embodiments, no control ring may be used. Instead, the distal ends of the pullwires 108 may be attached directly to a section or portion of the catheter body 102 where it may be steered, articulated, or bent, as described in an alternative embodiment below. The wires may be crimped, soldered, welded or interlocked in any suitable manner to a specific location on a bending section or portion of the catheter body 102. In some embodiments there may be more than one control ring 106 secured to the catheter body 102 or more than one control wire attachment control locations, sections, or portions for controlling, steering, or articulating more than one section or portion of the catheter body 102, e.g., into various complex shapes or curvatures (e.g., "S" curved shapes or "J" curved shapes, etc.). For example, the catheter 100 may be steered, articulated, or deflected into various complex shapes or curvatures that may conform to various complex shapes or curvatures of internal pathways of a patient to reach a target tissue structure of an organ inside the patient.

In this embodiment, the catheter 100 is functionally divided into four sections: a distal tip 112, a distal articulating section 114, a transition section 116, and a proximal shaft section 120.

The distal tip 112 includes an atraumatic rounded tip portion 122 and a control portion 124 in which the control ring 106 is mounted. The distal tip 112 also includes an exit port (not shown) in communication with the working lumen 104 and from which a working catheter or guidewire may extend distally therefrom. In one embodiment, the atraumatic rounded tip portion 122 is 2 mm in length and is composed of a suitable polymer material (e.g., Pebax® 55D/35D); and the control portion 124 is 1 mm in length and is composed of a suitable polymer material (e.g., Pebax® 35D).

In the distal articulating section 114, there are four pullwire lumens 110 that are equally spaced in an arcuate manner (i.e., ninety degrees apart), and thus, the four corresponding pullwires 108 are equally spaced as well. In an alternative embodiment, a different number of pullwires lumens 110, and thus, pullwires 108, can be used. For example, three pullwire lumens 110, and thus three pullwires 108, can be equally spaced in an arcuate manner (i.e., one hundred twenty degrees apart) in the distal articulating section 114. Thus, the pullwires 108 are mounted to the control ring 106 in orthogonal positions (i.e., ninety degrees apart), such that tensioning one of the pullwires 108 will selectively articulate the distal articulating section 114 in one of four orthogonal directions. Tensioning two of the pullwires 108 will allow the pertinent section to be articulated in an infinite number of directions (effectively, providing two degrees of freedom: pitch and roll).

The distal articulating section 114 preferably allows for a moderate degree of axial compression and optimal lateral flexibility. In one embodiment, the distal articulating section 114 is 30 mm in length. The pullwire lumens 110 extend through the distal articulating section 114 and may be constructed of a low friction material or may simply be unsupported tubular cavities in which the pullwires 108 respectively float. The entire working lumen 104 within the distal articulating section 114 is formed by an inner polymer tube (e.g., 0.001" thick PTFE). The distal articulating section 114 has a several portions of differing rigidities formed by having different polymer outer tubes. For example, the distal articulating section 114 may include a 5 mm rigid portion 126 having a moderately rigid outer polymer tube (e.g., Pebax® 55D) and a 25 mm articulatable portion 128 having an outer tube composed of a relatively flexible outer polymer tube (e.g., Pebax® 35D). The length of the articulatable portion 128 can vary depending on the performance requirements for the catheter 100. A longer articulatable portion 128 may be beneficial to increase the area of reach, while a shorter articulatable portion 128 may be beneficial for cannulating tight side branches in the anatomical vasculature. To increase its axial rigidity and elastic properties, the articulatable portion 128 comprises a double braided layer (e.g., sixteen 0.0005"×0.003" spring temper 304V stainless steel wires braided at 68 picks per inch (ppi) in a 2 over 2 pattern) embedded within the outer polymer tube. As will be described in further detail below, the distal ends of the pullwires 108 may be directly anchored between the two layers of the braid.

Figure 8:
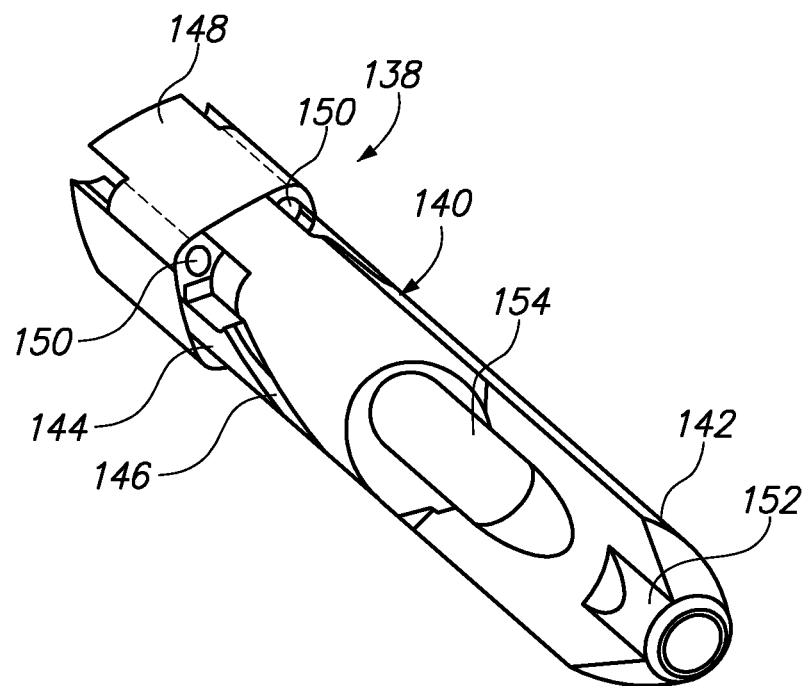
FIG. 8 is a perspective view of an adapter used to transition pullwires from one circumferential orientation to another circumferential orientation in the catheter of FIG. 7.
Figure 9:
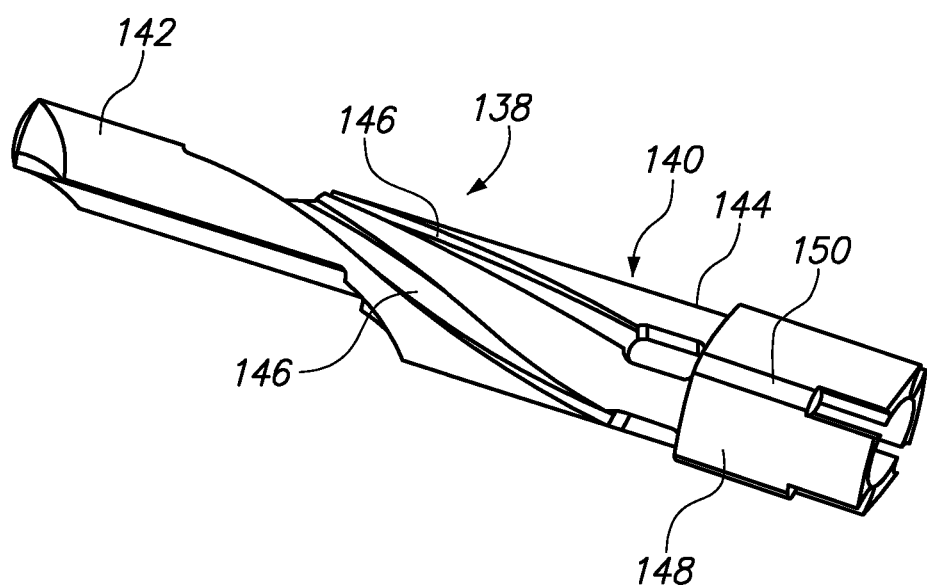
FIG. 9 is another perspective view of the adapter of FIG. 8.

The transition section 116 resists axial compression to clearly define the proximal end of the distal articulating section 114 and transfer the motion of the pullwires 110 to the distal articulating section 114, while maintaining lateral flexibility to allow the catheter 100 to track over tortuous anatomies. The transition section 136 may be 28 mm in length and be composed of an outer polymer tube (e.g., Pebax® 55D). Significantly, the transition section 116 transitions the four lumens 110 in the distal articulating section 114 to a single hollow stiffening tube 130 in the proximal shaft section 120. With further reference to FIGS. 8 and 9, the illustrated embodiment accomplishes this by using a molded adapter 138, which may be mounted within the outer polymer tube of the transition body section 120.

The adapter 138 includes an adapter body 140 having a proximal end 142 that interfaces with stiffening tube 130 in the proximal shaft section 120, and a distal end 144 that interfaces with the four pullwire lumens 110 in the distal articulating section 114. The adapter body 140 may be composed of a suitable rigid material, such as stainless steel or a glass-filled or high durometer plastic. The adapter 138 further includes a plurality of channels 146 formed in the external surface of the adapter body 140, a square-shaped boss 148 formed at the distal end 144 of the adapter body 140, a plurality of lumens 150 extending through boss 148, and a single port 152 formed in the proximal end 142 of the adapter body 140. The lumens 150 within the boss 148 are equally spaced from each other in coincidence with the equally spaced lumens 110 in the distal articulating section 114 of the catheter 100. In particular, the four lumens 150 are respectively disposed through the four corners of the boss 148. The lumens 150 within the boss 148 are also respectively coincident with the distal ends of the channels 146, and the single port 152 is coincident with the proximal ends of the channels 146. One of the channels 146 linearly extends along the length of the adapter body 140, while the remaining three channels 146 spiral around the length of the adapter body 140, so that the proximal ends of all four channels 146 converge into the single port 152. Thus, the four pullwires 108 extend proximally from the distal articulating section 114, into the lumens 150 formed in the boss 148 of the adapter body 140, along the channels 146, into the single port 152, and then into the stiffening tube 130.

The adapter 138 further includes a working lumen 154 extending through the boss 148 and a distal portion of the adapter body 140. The distal end of the working lumen 154 is in coincidence with the portion of the working lumen 104 extending through the distal articulating section 114. The proximal end of the working lumen 130 exits the adapter body 140 just proximal to the single port 152, such that it is in coincidence with the lumen of the transition section 136, which, in turn, is in coincidence with the working lumen 104 extending through the proximal shaft section 120. In the same manner that the working lumen 104 and stiffening tube 130 are offset from the axis of the proximal shaft section 120 (as described below), the working lumen 154 and single port 152 are offset from the axis of the adapter body 140. It should be appreciated that the use of the adapter 138 allows the four pullwires 108 to be transitioned from the respective lumens 110 of the distal articulating section 114 into the single stiffening tube 130 without having to spiral the pullwires 108 and corresponding lumens through the wall of the catheter tube 102, thereby allowing the thickness of the wall to be uniform and minimizing the possibility of weakened regions in the catheter tube 102 and possible inadvertent kinking Therefore, it is particularly suitable for thin walled catheters.

As will be described below in further embodiments, where wall thicknesses are not as thin, instead of using the adapter 140, the equally spaced pullwire lumens 110 from the distal articulating section 114 may be gradually converged via the transition section 116 onto one side of the proximal shaft section 120 and into the stiffening tube 130.

Referring back to FIG. 7, the proximal shaft section 120 combines lateral flexibility (which is needed for optimal tracking) with axial stiffness (which is needed for optical articulation performance). The proximal shaft section 120 represents the majority of the length of the catheter 100. The entire working lumen 104 within the proximal shaft section 120 is formed by an inner polymer tube (e.g., 0.001" thick PTFE).

The proximal shaft section 120 gradually transitions the catheter 100 from the transition section 116 to the more rigid remaining portion of the catheter 100 by having several portions of differing rigidities formed by having different polymer outer tubes. For example, the proximal shaft section 120 may include a first 6 mm proximal portion 132 including outer polymer tube (e.g., Pebax® 55D); a second 7.5 mm proximal portion 134 including an outer polymer tube (e.g., Pebax® 72D) that is more laterally rigid than the outer polymer tube in the first proximal portion 128; and a third lengthy (e.g., 1 meter long) proximal shaft section 136 including an outer polymer tube (e.g., Nylon-12) that is resistant to rotational forces to reduce the effect of curve alignment when the catheter 100 is contorted to the tortuous anatomy. To increase its axial rigidity, the proximal shaft section 120 comprises a double braided layer (e.g., sixteen 0.0005"×0.003" spring temper 304V stainless steel wires braided at 68 picks per inch (ppi) in a 2 over 2 pattern) embedded within the outer polymer tube.

Significantly, unlike with the distal articulating section 114 in which the pullwires 108 are disposed in equally spaced apart lumens, the pullwires 108 in the proximal shaft section 120 are disposed in one or more lumens on one arcuate side of the proximal shaft section 120. In the illustrated embodiment, the one or more lumens takes the form of the previously mentioned stiffening tube 130 disposed along the catheter body 102 along the proximal shaft section 120, and through which the pullwires 108 are housed and passed back to the proximal adapter 101. As will be described in further embodiments below, the one or more lumens may take the form of a plurality of tubes that respectively house the pullwires 108.

The inner diameter of the stiffening tube 130 is preferably large enough to allow the pullwires 108 to slide freely without pinching each other. The stiffening tube 130 is composed of a material that is more axially rigid than the surrounding material in which the catheter body 102 is composed. For example, the stiffening tube 130 may take the form of a stainless steel hypotube or coil pipe, while the catheter body 102 along the proximal shaft section 120 may be composed of a more flexible polymer or polymer composite, as will be described in further detail below. The stiffening tube 130 must be laminated into the catheter body 102, thereby allowing the stiffening tube 130 to support the axial loads on the catheter 100 from the tensioning of the pullwires 108. Due to the non uniform stiffness in the catheter cross section, the neutral axis will no longer be in the geometric center of the catheter body 102 along the proximal shaft section 120, but rather be shifted closer to the axis of the stiffening tube 130, thereby minimizing the impact on bending stiffness. Thus, by locating the pullwires 108 in one lumen (i.e., the stiffening tube 130) in the catheter body 102, and designing the catheter body 102 to be relatively flexible, thereby controlling the location of the neutral axis, an axially stiff, but laterally flexible, proximal shaft section 120 can be achieved.

Figure 10:
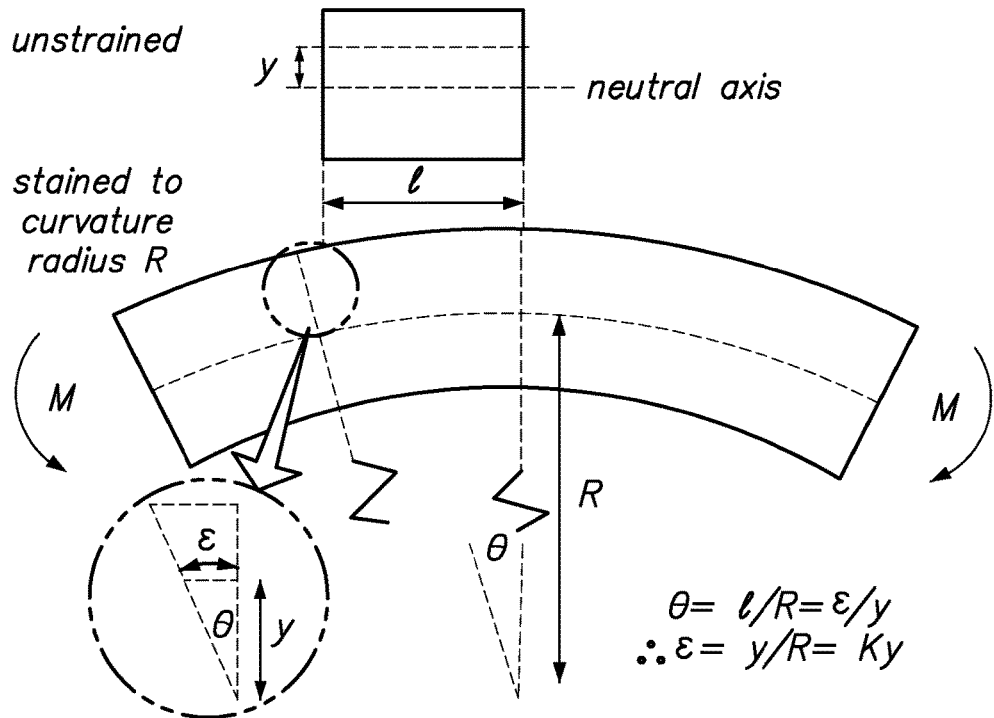
FIG. 10 is a diagram showing the neutral axis of the bend in a distal articulating section of the catheter of FIG. 7.

The effects of bending stiffness relative to the neutral axis will now be described. The neutral axis can be considered the axis in the cross-section of a beam or shaft along which there are no longitudinal stresses or strains when the beam or shaft is bent. If the cross-section of the beam or shaft is symmetrical, isotropic, and is not curved before a bend occurs, then the neutral axis is at the geometric centroid of the cross-section. When the bend occurs, all fibers on one side of the neutral axis are in a state of tension, while all fibers on the other side of the neutral axis are in a state of compression. As shown in FIG. 10, the axial strain ε is given by the ratio y/R, where y is the distance from the neutral axis, and R is the radius of curvature of the neutral axis. It follows that the axial stress σ at any point is given by $E_{Ky}$, where E is the modulus of elasticity and K is the curvature of the beam or shaft. Thus, the axial stress σ is also proportional to the distance from the neutral axis y. Therefore, when high stiffness members are further from the neutral axis, the bending stress and hence bending stiffness is higher.

Figure 11:
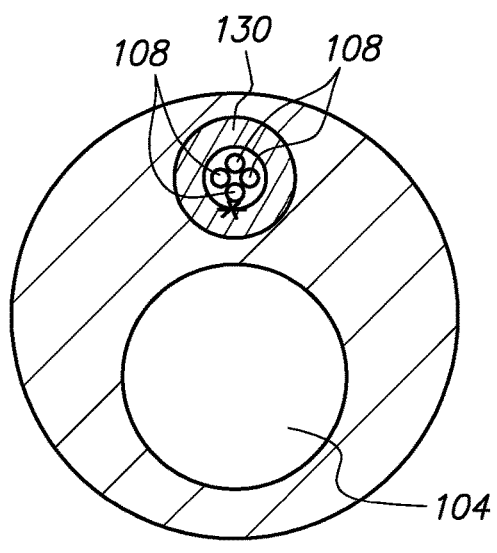
FIG. 11 is a cross-sectional view of the proximal shaft of the catheter of claim 7, particularly showing the location of a neural bending axis relative to the pullwires.
Figure 12:
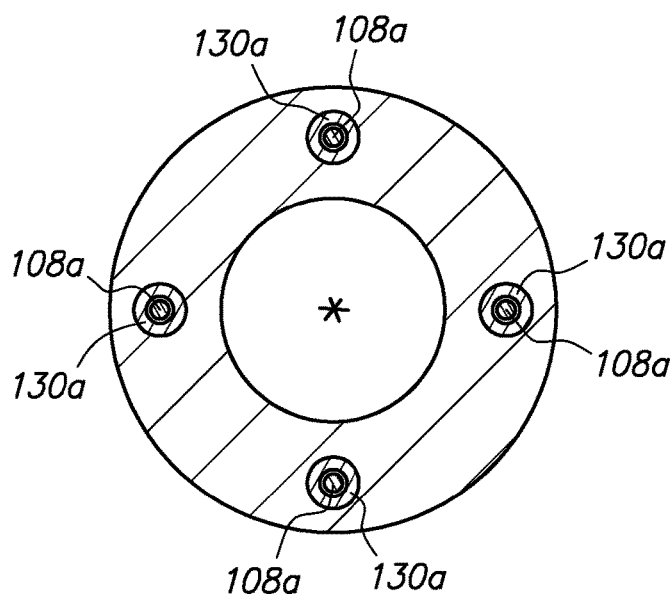
FIG. 12 is a cross-sectional view of the proximal shaft of a prior art catheter of claim 7, particularly showing the location of a neural bending axis relative to the pullwires.

It follows that when the pullwires 108 (and any axially stiff compressive members that provide the reaction force) are located closer to the neutral axis, the bending stiffness of the proximal shaft section 120 is decreased. That is, as shown in FIG. 11, there is only one stiff member (i.e., the stiffening tube 130) that supports the axial load of the pullwires 108, and therefore, the neutral axis (represented by the asterisk) of the proximal shaft section 120 will be close to the location of the stiffening tube 130. Ultimately, the exact location of the neutral axis will depend on the relative stiffness of the stiffening tube 130 relative to the remainder of the material in the proximal shaft section 120. Therefore, each of the pullwires 108 will be relatively close to the neutral axis. Notably, the working lumen 104 is offset from the geometric center of the proximal shaft section 120 in order to accommodate the stiffening tube 130. In contrast, as shown in FIG. 12, a conventional symmetrical arrangement may distribute four stiffening members 130a about the geometric center of the proximal shaft section 130a, and therefore, the neutral axis of the proximal shaft section 130a will essentially be at its geometric center. As a result, the pullwires 108a will be relatively far from this neutral axis. Thus, it can be appreciated from a comparison between FIGS. 11 and 12 that the maximum distance from any of the pullwires 108 to the neutral axis in the preferred embodiment is far shorter than the pullwires 108a to the neutral axis in the conventional design.

Therefore, by having the pullwires 108 close to or on the neutral axis, the pullwires 108 will have a minimum change in length during an externally applied shaft curvature. This achieves consistent articulation of the distal articulating section 114 independent of the curvature of the proximal shaft section 120. In other words, the proximal shaft section 120 does not need to be maintained substantially straight in contrast to the conventional pullwire arrangement, which requires the operator to maintain the proximal shaft section relatively straight. Thus, locating the pullwires 108 close to the neutral axis of the proximal shaft section 120 allows the operator to traverse anatomical features, such as the iliac bifurcation or the aortic arch—not just with the flexible distal articulating section 108, but with the entire catheter 100 as required, while at the same time having full control of the distal tip of the catheter 100.

Furthermore, because the proximal shaft section 120 is relatively axially stiff, articulation of the distal articulating section 114 by tensioning one or more of the pullwires 108 will not cause significant lateral deflection of the proximal shaft section 120, thereby improving instrument stability. Furthermore, because the pullwires 108 are close to the neutral axis in the proximal shaft section 120, there is only a small radial distance between the pullwires 108 and the neutral axis. This radial distance is what causes the bending moment that leads to articulation of the distal articulating section 114 (or any other articulating section). With small bending moments generated by tensioning the pullwires 108, there will be minimal articulation of the proximal shaft section 120. Therefore, varying the position of the neutral axis with respect to the position of the pullwires 108 in any section of the catheter 100 can influence how much the distal articulating section 114 will bend when a given load is applied to a pullwire 108. For example, the distal articulation section 114 has the neutral axis in the geometric center and when any tension is applied to one or more pullwires 108, a moment will be generated and the distal tip 112 will articulate. On the other hand, the proximal shaft section 120 will not tend to bend and hence twist during tensioning of those same pullwires 108 of the distal articulating section 114 because of the smaller moment arm, thereby minimizing the tendency for the catheter 100 to curve align. Notably, even if a tensioned pullwire 108 initially causes curve alignment by moving to the inside of the curved proximal shaft section 120, the catheter 100 will be stable thereafter, since all the pullwires 108 are located on one arcuate side of the catheter body 102. That is, once the stiffening tube 130, and thus the pullwires 108, move to the inside of the curved proximal shaft section 120, any of the pullwires 108 can be tensioned without causing further rotation of the curved proximal shaft section 120, thereby allowing the distal articulating section 114 to be articulated in the desired direction. Furthermore, because only one stiffening tube 130 is utilized, as opposed to four separate stiffening tubes or coil pipes, for the respective four pullwires 108, there is a significant reduction in cost and a consistent low bending stiffness irrespective of the articulation loads applied to the pullwires 108.

Having described the construction of the catheter 100, one method of manufacturing the catheter 100 will now be described. In this method, the distal articulating section 114 and proximal shaft section 120 are fabricated separately, and then mounted to each other when the transition section 136 is fabricated. The distal tip 112 can then be formed onto the assembly to complete the catheter 300.

The distal articulating section 114 can be fabricated by first inserting a copper wire process mandrel through a lumen of an inner polymer tube (e.g., a PTFE extrusion) having the intended length of the distal articulating section 114. Then, using a braiding machine (embodiments of which will be described in further detail below), a first layer of braiding is laid down over the length of the inner polymer tube. Next, four PTFE-coated stainless steel wire process mandrels are respectively disposed over the length of the braided inner polymer tube in four equally spaced circumferential positions (i.e., clocked ninety degrees from each other), and a second layer of braiding is laid down over the four wire process mandrels. Next, outer polymer tubes having different durometers and lengths corresponding to the lengths of the different portions of the distal articulating section 114 (e.g., a Pebax® 55D extrusion for the rigid section 120 and a Pebax® 35D extrusion for the articulatable section 122) are slid over the fully braided inner polymer tube, and then heat shrink tubing is slid over the outer polymer tubes. The assembly is then heated to a temperature above the melting temperature of the outer polymer tubes, but below the melting temperature of the heat shrink tubing.

As a result, the outer polymer tubes are laminated to the assembly. In particular, the outer polymer tubes melt and flow, while the heat shrink tubing shrinks and compresses the melted polymer tubes into the braid and around the four stainless steel process mandrels. The assembly then cools and solidifies to integrate the inner polymer tube, braid, and outer polymer tubes together. Then, the center copper wire can be pulled from the assembly to create the working lumen 104, and the four stainless steel wires can be pulled from the assembly to respectively create the four pullwire lumens 110.

In a similar manner, the proximal shaft section 120 can be fabricated by first inserting a copper wire process mandrel and the stiffening tube 130 through respective offset lumens of an inner polymer tube (e.g., a PTFE extrusion) having the intended length of the proximal shaft section 120. Then, using a conventional braiding machine, two layers of braiding are laid down over the length of the inner polymer tube. Next, outer polymer tubes having different durometers and lengths corresponding to the lengths of the different portions of the first proximal shaft section 120 (e.g., a Pebax® 55D extrusion for the proximal portion 130, a Pebax® 72D extrusion for the second proximal portion 132, and a Nylon-12 extrusion for the third proximal portion 134) are slid over the fully braided inner polymer tube, and then heat shrink tubing is slid over the outer polymer tubes. The assembly is then heated to a temperature above the melting temperature of the outer polymer tubes, but below the melting temperature of the heat shrink tubing. As a result, the outer polymer tubes are laminated to the assembly. In particular, the outer polymer tubes melt and flow, while the heat shrink tubing shrinks and compresses the melted polymer tubes into the braid and around the four stainless steel process mandrels. The assembly then cools and solidifies to integrate the inner polymer tube, braid, stiffening tube 130, and outer polymer tubes together. Then, the center copper wire can be pulled from the assembly to create the working lumen 104.

Next, the distal articulating section 114 and proximal shaft section 120 are coupled to each other by fabricating the transition section 136 between the distal articulating section 114 and proximal shaft section 120. In particular, a center wire process mandrel is inserted through the working lumen 154 of the adapter 138 and four wire process mandrels are inserted through the single port 152, four channels 146, and four lumens 150 of the adapter 138. The proximal end of the center wire process mandrel is then inserted through the working lumen 104 in the proximal shaft section 120, and the distal end of the center wire process mandrel is then inserted through the working lumen 104 in the distal articulating section 114. The proximal ends of the four wire process mandrels are inserted through the stiffening tube 130 in the proximal shaft section 120, and the distal ends of the four wire process mandrels are inserted through the pullwire lumens 110 in the distal articulating section 114. The proximal shaft section 120 and distal section 116 are then moved towards each other until they abut the opposite ends of the adapter 138.

Next, an outer polymer tube having a durometer and length corresponding to the length of the transition catheter 136 (e.g., Pebax® 55D) is slid over the adapter 138, and then heat shrink tubing is slid over the outer polymer tube. The assembly is then heated to a temperature above the melting temperature of the outer polymer tube, but below the melting temperature of the heat shrink tubing. As a result, the outer polymer tube is laminated to the assembly. In particular, the outer polymer tube melts and flows, while the heat shrink tubing shrinks and compresses the melted polymer tube into the desired cylindrical shape. The assembly then cools and solidifies to integrate the inner polymer tube, adapter 138, and outer polymer tube together. Then, the center copper wire can be pulled from the assembly to create the working lumen 104.

Then, the proximal ends of the pullwires 108, which may be pre-fastened (e.g., soldered, welded, brazed, or glued) to the control ring 106, are inserted into the pullwire lumens 110 at the distal end of the catheter body 102, and advanced through the lumens 110 until they exit the proximal end of the catheter body 102. The control ring 106 is then slid over the distal end of the central wire process mandrel extending from the distal articulating section 114 until it abuts the rigid portion 120 of the distal articulating section 114. Then, outer polymer tubes having different durometers and lengths corresponding to the lengths of the different portions at the distal tip 112 (e.g., a Pebax® 55D/35D extrusion for the tip portion 122, and a Pebax® 35D extrusion for the control portion 124) are slid over the center wire process mandrel and control ring 106, and then heat shrink tubing is slid over the outer polymer tubes. The assembly is then heated to a temperature above the melting temperature of the outer polymer tube, but below the melting temperature of the heat shrink tubing. As a result, the outer polymer tube melts and flows, while the heat shrink tubing shrinks and compresses the melted polymer tube into the desired cylindrical shape. The assembly then cools and solidifies to integrate the inner polymer tube, adapter 138, and outer polymer tube together. Then, the distal tip 122 can be cut to a rounded shape, and the center wire process mandrel can be pulled from the catheter 100. The proximal end of the catheter tube 102 can then be mounted to the proximal adapter 100, and the proximal ends of the pullwires 108 can be installed on the spools or drums 103 of the proximal adapter 101.

As briefly discussed above, instead of utilizing a control ring 106, the distal ends of the pullwires 108 may be attached directly to a section or portion of the catheter body 102 where it may be steered, articulated, or bent. In particular, the working lumen 104 and pullwire lumens 110 are formed and the braid and outer polymer tubes are applied to the inner polymer tube in the same manner described above, with the exception that the distal ends of the pullwires 108 are anchored between the braid layers (or alternatively, layers of a different type of wire support structures, such as a coil or mesh), as illustrated in FIGS. 31A-31I. The wire support structure may be made of metal, plastic, fabric, thread, or any other suitable material.

Figure 31A:
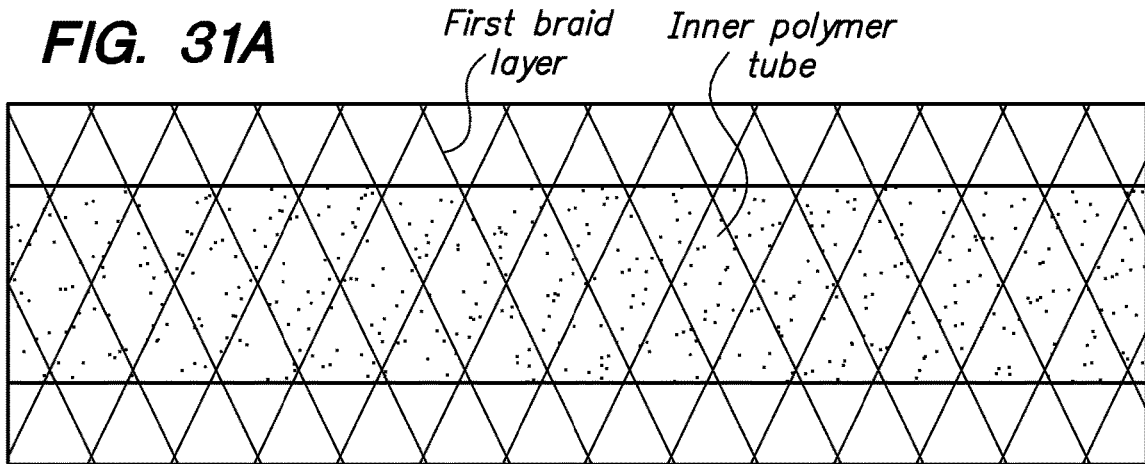
FIGS. 31A-31I are plan views illustrating one method of directly anchoring a pullwire to the braid of a steerable catheter.
Figure 31B:
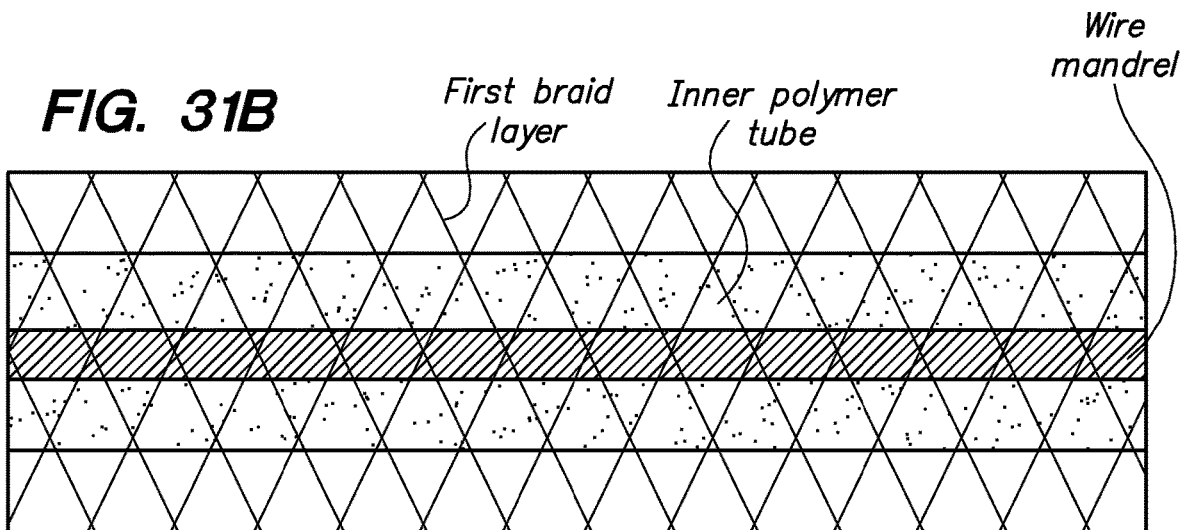
Figure 31C:
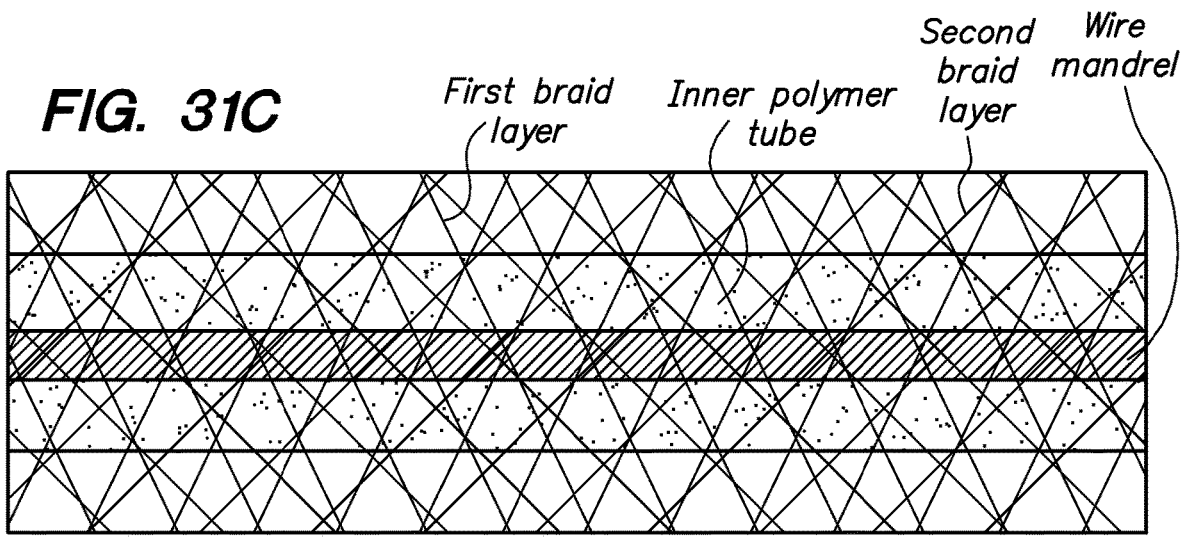

The distal articulating section 114 is fabricated by disposing a first layer of braiding over the length of the inner polymer tube (FIG. 31A), four PTFE-coated stainless steel wire process mandrels (only one shown for purposes of clarity) are respectively disposed over the length of the braided inner polymer tube in four equally spaced circumferential positions (i.e., clocked ninety degrees from each other) (FIG. 31B), and a second layer of braiding is laid down over the four wire process mandrels the length of the inner polymer tube (FIG. 31C).

Figure 31D:
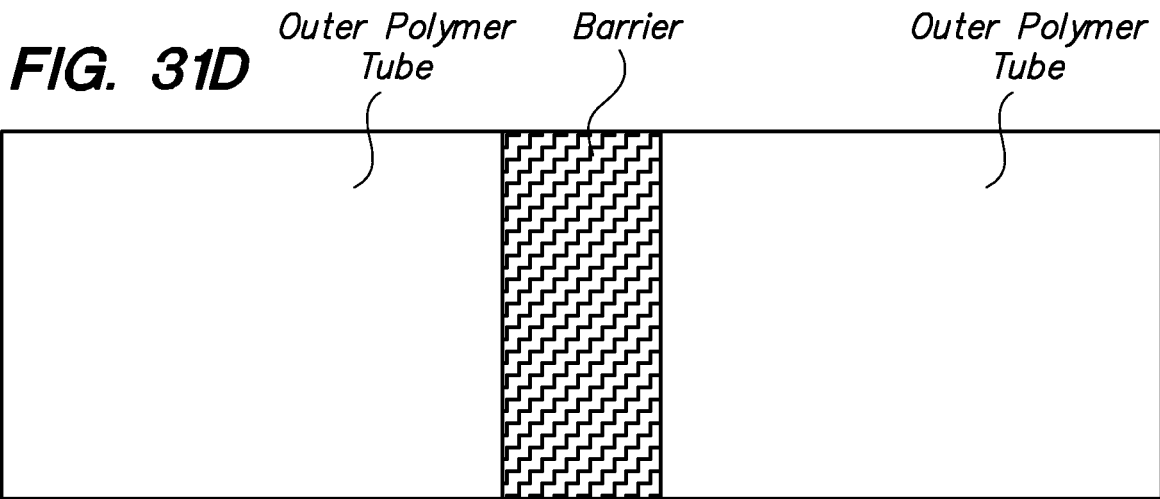

Next, the outer polymer tubes are slid over the fully braided inner polymer tube in the same manner as discussed above, with the exception that a barrier is disposed over a region of the braided inner polymer tube to which the pullwires 108 will eventually be anchored (FIG. 31D). In the illustrated embodiment, the barrier is a cylindrical, and in particular, takes the form of a short section of heat shrink tubing that is disposed over a corresponding short cylindrical region of the braided inner polymer tube. Additional heat shrinking (not shown) is then disposed over the outer polymer tubes and barrier, and the assembly is then heated to a temperature above the melting temperature of the outer tube tubes, but below the melting temperature of the heat shrink tubing and barrier.

Figure 31E:
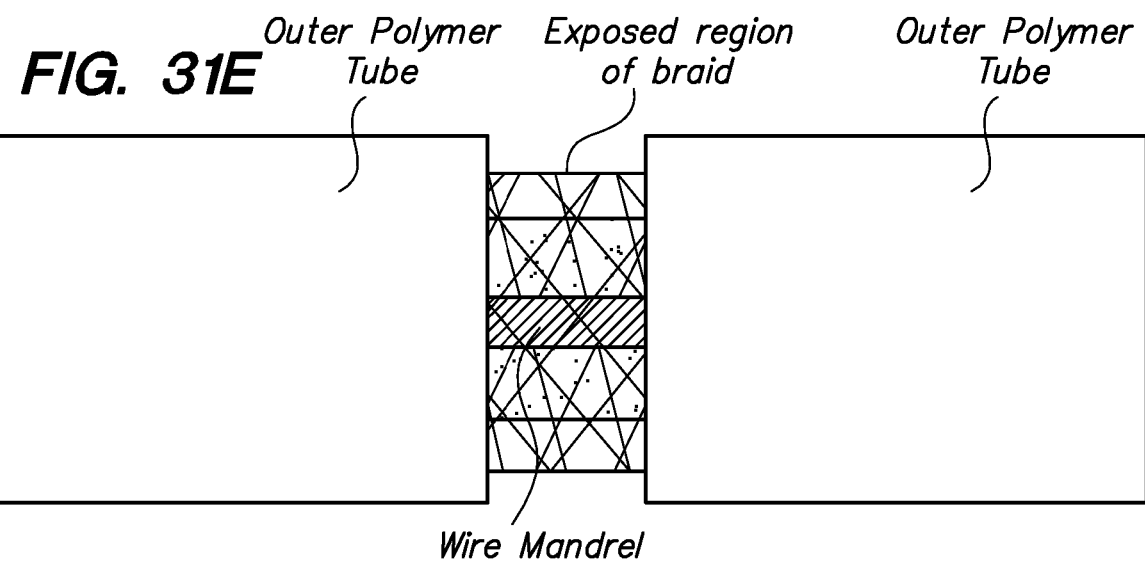
Figure 31F:
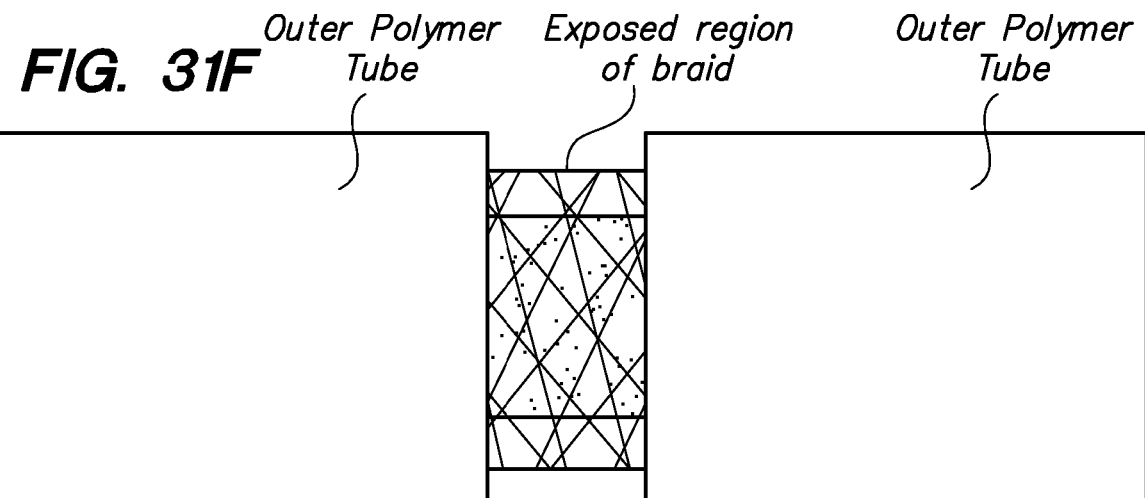

As a result, the outer polymer tubes are laminated to the assembly. In particular, the outer polymer tubes melt and flow, while the heat shrink tubing shrinks and compresses the melted polymer tubes into the braid and around the four stainless steel process mandrels. Because the barrier has a melting temperature above the temperature of the applied heat, the barrier does not melt and prevents the melted outer polymer tubes from being compressed into the circumferential region of the braid. The assembly then cools and solidifies to integrate the inner polymer tube, braid, and outer polymer tubes together. The barrier is then removed from the catheter body 102, thereby exposing the circumferential region of the braid (FIG. 31E). The center copper wire (not shown) can then be pulled from the assembly to create the working lumen 104, and the four stainless steel wires can be pulled from the assembly to respectively create the four pullwire lumens 110 in the same manner discussed above (FIG. 31F). The proximal shaft section 120 and transition section 136 are then fabricated with the distal articulating section 114 in the same manner described above.

Figure 31G:
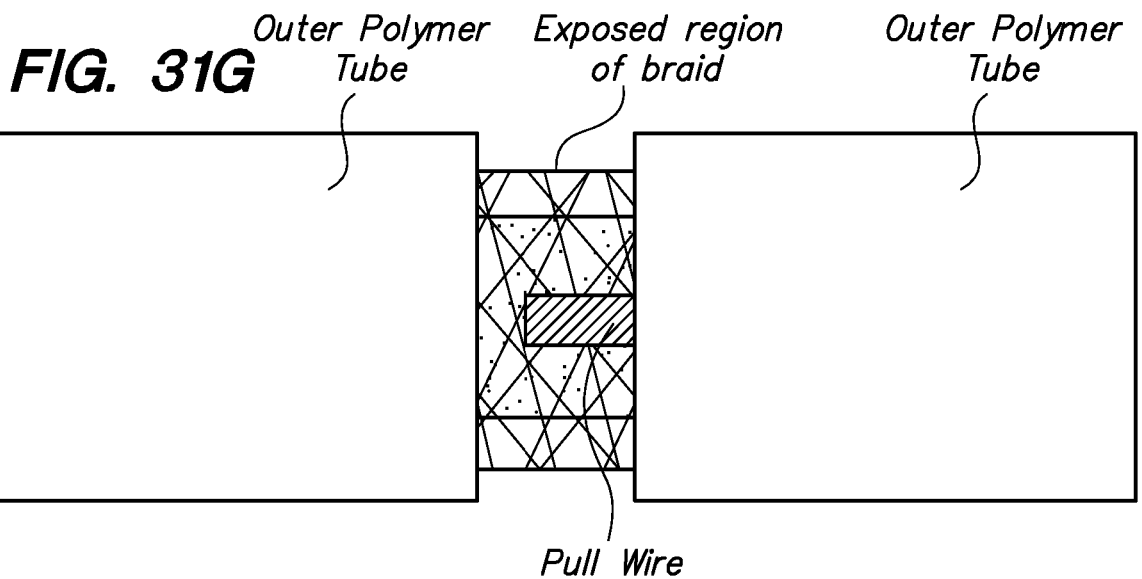
Figure 31H:
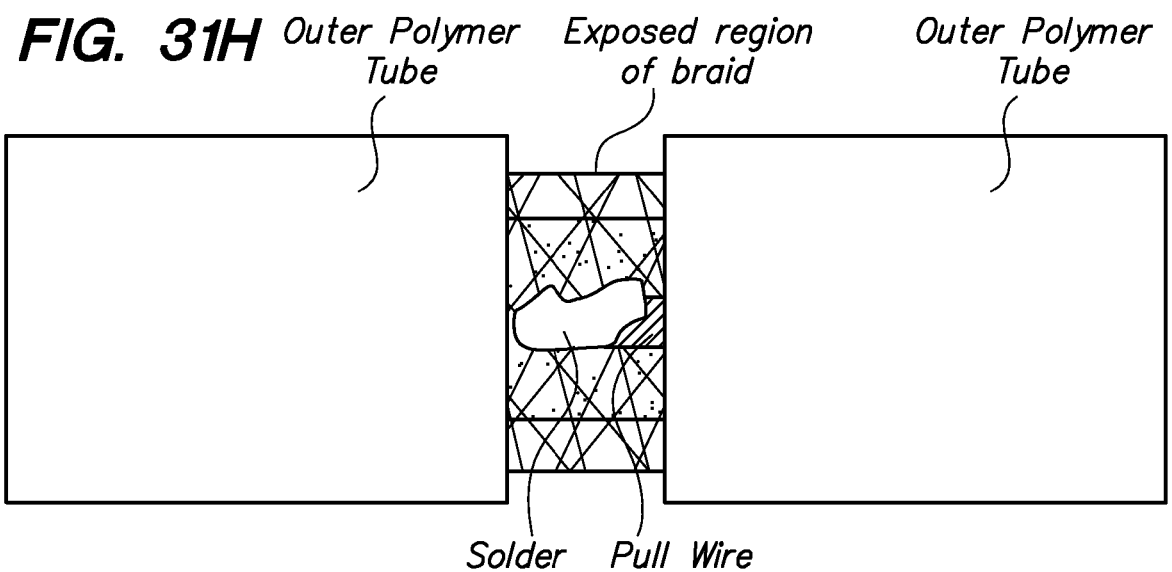

Then, the proximal ends of the pullwires 108 are inserted into the pullwire lumens 110 at the distal end of the catheter body 102, and advanced through the lumens 110 until they exit the proximal end of the catheter body 102 and the distal ends of the pullwires 108 are disposed within the exposed circumferential region of the braid (FIG. 31G). The distal ends of the pullwires 108 are then anchored to the exposed circumferential region of the braid via, e.g., soldering, welding, brazing, or gluing (FIG. 31H). In the case where the distal ends of the pullwires 108 are anchored via soldering, 80/20 Au/Sn, which has a melting temperature below the temperature required to damage adjacent components, namely the inner PTFE polymer tube and the stainless steel braid, can be used. Because the distal ends of the pullwires 108 are anchored between the two layers of braid by virtue of the disposition of the pullwire lumens 110 between the two layers of braid, the distal ends of the pullwires 108 are more firmly anchored to the braid, since the bonding material anchored the pullwires 108 above and below the pullwires 108. In contrast, if the pullwires 108 are anchored only to one side of the braid, the pullwires 108 would tend to pull away from the braid by either pushing toward the inner polymer tube or being forced outwardly from the inner polymer tube.

Figure 31I:
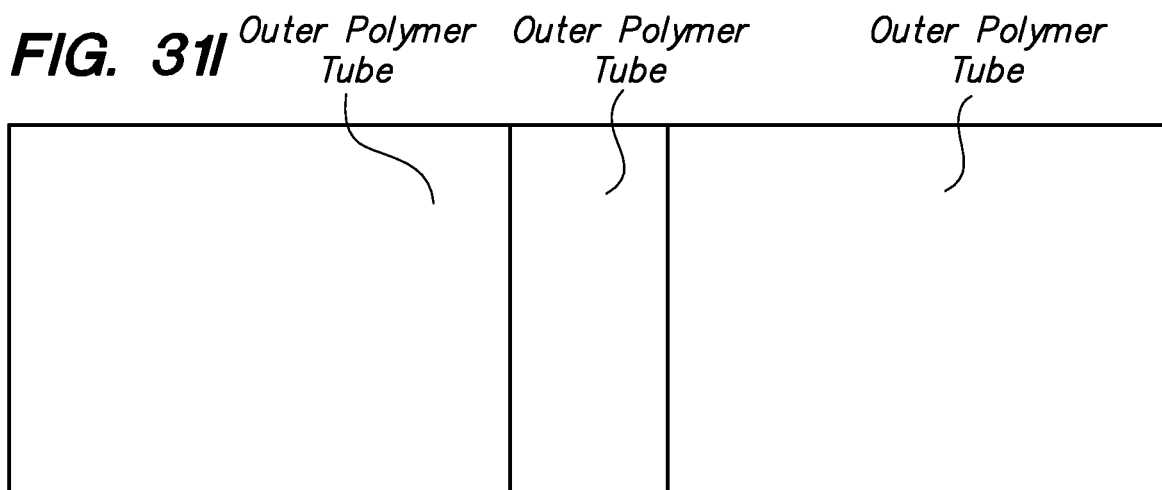
Figure 36:
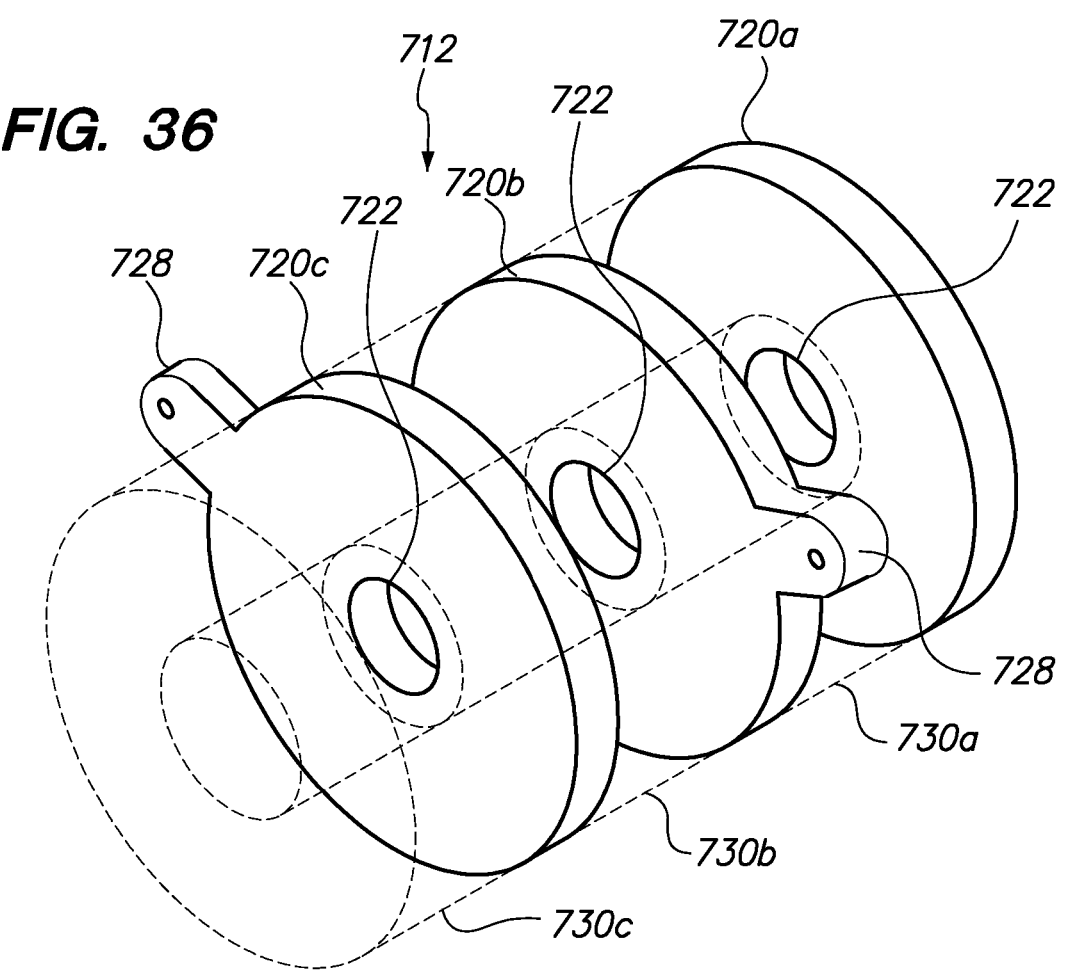
FIG. 36 is a perspective view of an iris assembly that can be used in the nose cone of FIG. 35.
Figure 37:
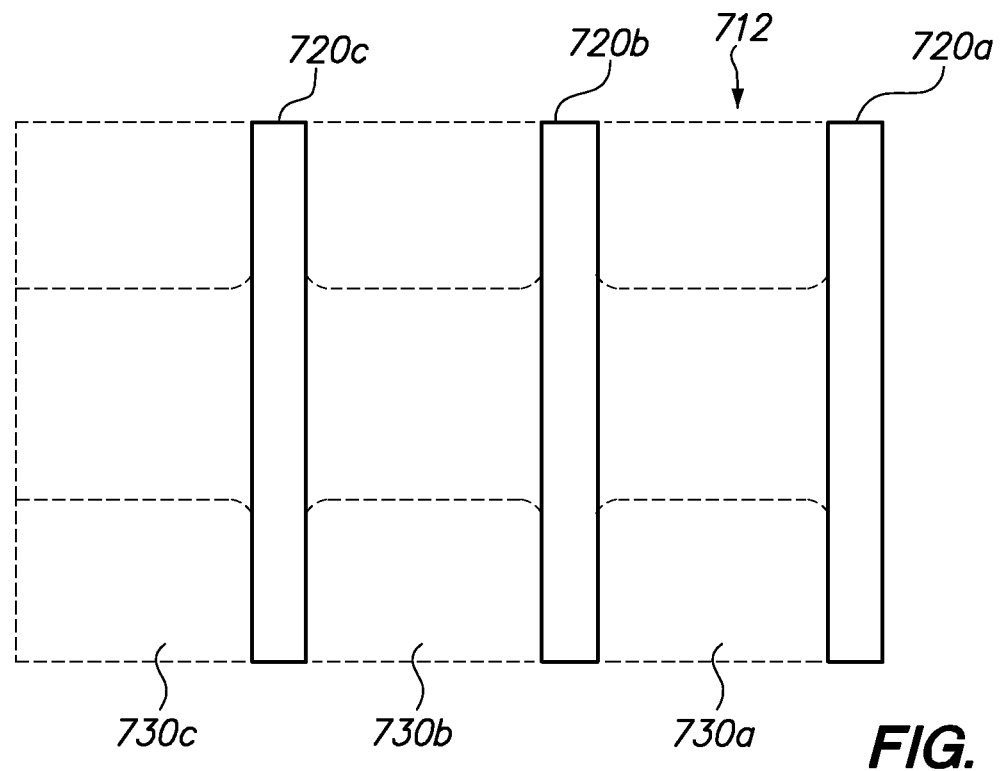
FIG. 37 is a side view of the iris assembly of FIG. 36.

Once the distal ends of the pullwires 108 are anchored to the braid, an outer polymer tube (e.g., a Pebax® 35D extrusion) can then be slid over the exposed circumferential region of the braid, and then heat shrink tubing (not shown) is slid over the outer polymer tube (FIG. 31I). The assembly is then heated to a temperature above the melting temperature of the outer polymer tube, but below the melting temperature of the heat shrink tubing. As a result, the outer polymer tube melts and flows, while the heat shrink tubing shrinks and compresses the melted polymer tube into the circumferential portion of the braid. The assembly then cools and solidifies. The proximal end of the catheter tube 102 can then be mounted to the proximal adapter 100, and the proximal ends of the pullwires 108 can be installed on the spools or drums 103 of the proximal adapter 101.

It should be appreciated the technique of directly anchoring the distal ends of the wires to the braid eliminates the need for the control ring, thereby reducing the cost and fabrication process time for the catheter 100. Furthermore, the resulting catheter has a less abrupt stiffness characteristic. Although, the technique of directly anchoring the distal ends of wires to the braid has been disclosed in the context of pullwires, it should be appreciated that this technique can be performed in the context of other types of wires. For example, the wires can be electrical signal wires and/or radio frequency (RF) ablation wires in an electrophysiology catheter. In this case, an electrode, rather than an outer polymer tube, can be disposed over the exposed portion of the braid in electrical communication with the wire or wires. The electrode can be used as a conductive surface that either measures a localized electrical potential or delivers RF ablation energy. In the case where the distal end of the wire or wires are soldered to the braid, the electrode can, e.g., be formed by flowing solder into and over the exposed portion of the braid during the same procedure used to solder the distal end of the wire or wires to the braid.

With reference now to FIG. 13, an embodiment of another flexible and steerable elongate catheter 200 will be described. The catheter 200 is similar to the previously described catheter 100, with the exception that the catheter 200 is designed with three, instead of four pullwires. The catheter 200 may be used in the robotic catheter assembly 18 illustrated in FIGS. 5 and 6.

The catheter 200 generally includes an elongate catheter body 202, a working lumen 204 disposed through the entire length of the catheter body 202 for delivering one or more instruments or tools from the proximal end of the catheter body 202 to the distal end of the catheter body 202, a control ring 206 secured the distal end of the catheter body 202, a plurality of pullwires 208 housed within one or more lumens 210 extending through the catheter body 202, and a proximal adapter 151 (with associated spools or drums 153 to which the proximal ends of the pullwires 208 are coupled). The working lumen 204, control ring 206, pullwires 208, and pullwire lumens 210 may be constructed and function in a similar manner as the working lumen 104, control ring 106, pullwires 108, and pullwire lumens 110 described above.

Like the catheter 100, the catheter 200 is functionally divided into four sections: a distal tip 212, a distal articulating section 214, a transition section 216, and a proximal shaft section 220.

The distal tip 212, distal articulating section 214, proximal shaft section 220, and proximal adapter 151 may be respectively identical to the distal tip 112, distal articulating section 114, proximal shaft section 120, and proximal adapter 103 of the catheter 100, with the exception that three pullwires 208, instead of three, are accommodated. Thus, three pullwire lumens 210, and thus three pullwires 208, are equally spaced in an arcuate manner (i.e., one hundred twenty degrees apart) within the distal articulating section 214, and the stiffening tube 230 within the proximal shaft section 220 houses the three pullwires 208. The proximal adapter 201 includes three spools or drums 153 to which the proximal ends of the pullwires 208 terminate.

Figure 14:
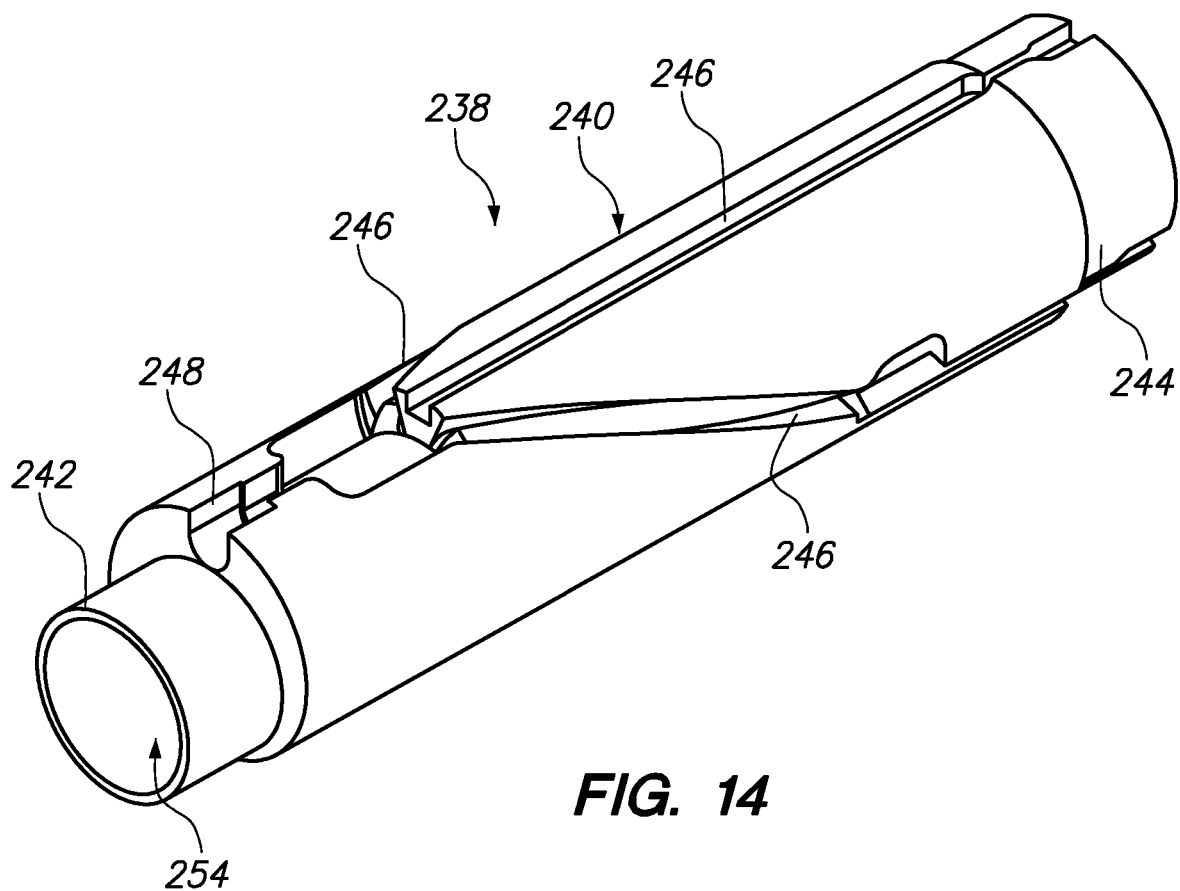
FIG. 14 is a perspective view of an adapter used to transition pullwires from one circumferential orientation to another circumferential orientation in the catheter of FIG. 13.
Figure 15:
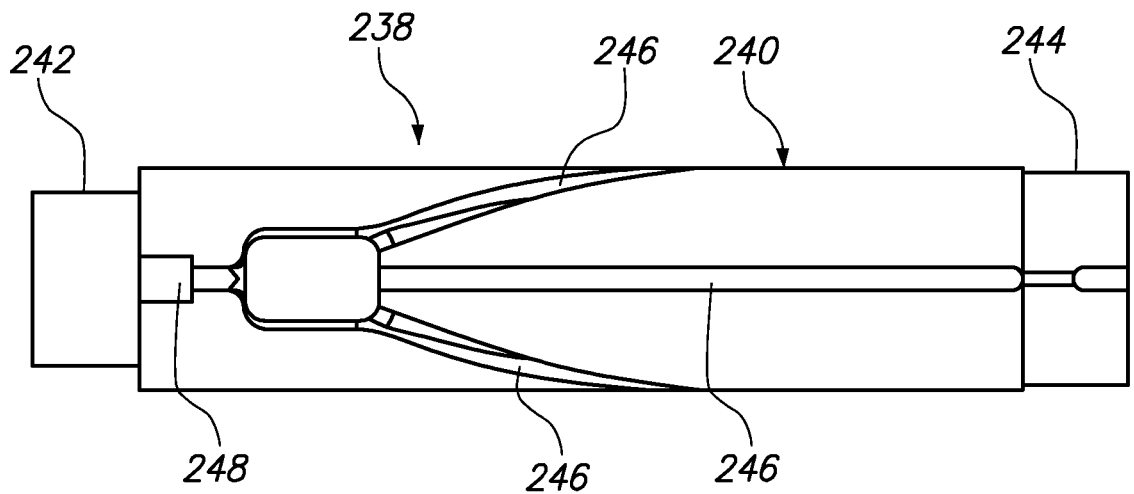
FIG. 15 is a top view of the adapter of FIG. 14.
Figure 16:
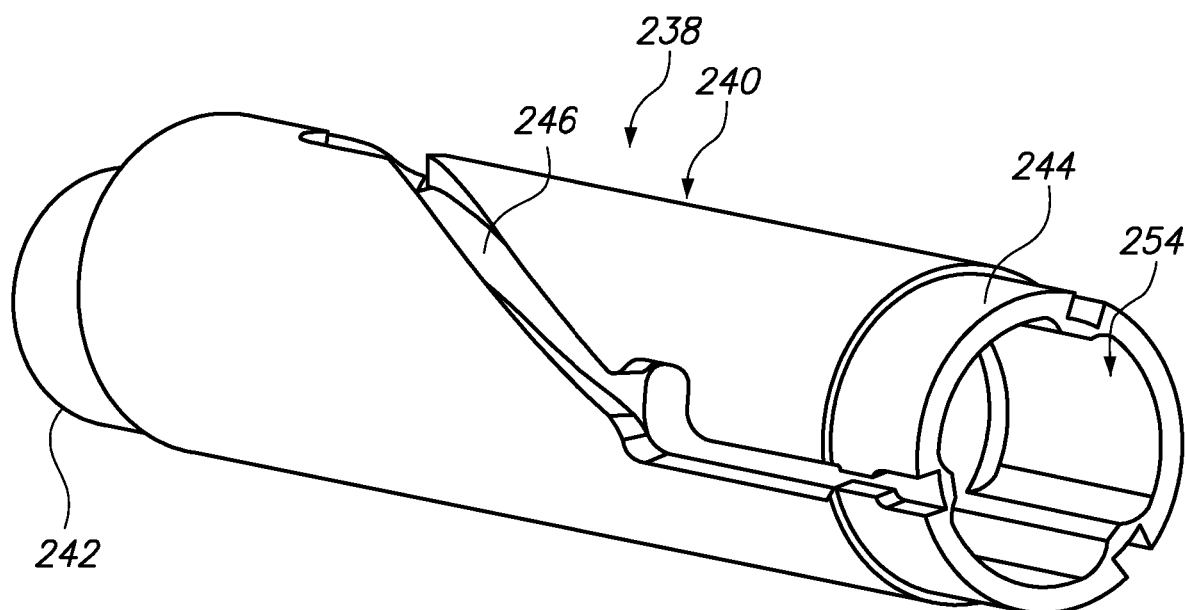
FIG. 16 is another perspective view of the adapter of FIG. 14.

Like the transition section 116, the transition section 216 transitions the equal spacing of the lumens 210 in the distal articulating section 214 to a single stiffening tube 230 within the proximal shaft section 214. With further reference to FIGS. 14-16, the illustrated embodiment accomplishes this by using an adapter 238, which may be mounted within the outer polymer tube of the transition body section 220. The adapter 238 is similar to the adapter 138 of the catheter 100, with the exception that it is designed to transition three, instead of four, pullwires 208.

In particular, the adapter 238 includes an adapter body 240 having a proximal end 242 that interfaces with the stiffening tube 230 in the proximal shaft section 220, and a distal end 244 that interfaces with the three pullwire lumens 210 in the distal articulating section 214. The adapter body 240 may be composed of a suitable rigid material, such as stainless steel. The adapter 238 further includes a plurality of channels 246 formed in the external surface of the adapter body 240, and a single channel 248 formed in the external surface of the adapter body 240 in communication with the plurality of channels 246. The distal ends of the channels 246 are equally spaced from each other in coincidence with the equally spaced lumens 210 in the distal articulating section 214, and the proximal end of the single channel 248 is in coincidence with the stiffening tube 230 in the proximal shaft section 220. One of the channels 246 linearly extends along the length of the adapter body 240, while the remaining two channels 246 spirals around the length of the adapter body 240, so that the proximal ends of all three channels 246 converge into the single channel 248. Thus, the three pullwires 208 extend proximally from the distal articulating section 214, along the three channels 246, converge into the single channel 248, and then into the stiffening tube 230.

The adapter 238 further includes a working lumen 254 extending entirely through the adapter body 240. The distal end of the working lumen 254 is in coincidence with the portion of the working lumen 204 extending through the distal articulating section 214, and the proximal end of the working lumen 254 is in coincident with the portion of the working lumen 204 extending through the proximal shaft section 220. In the same manner that the working lumen 204 and stiffening tube 230 are offset from the axis of the proximal shaft section 120, the working lumen 254 and single channel 248 are offset from the axis of the adapter body 240. Like with the adapter 138 of the catheter 100, the adapter 238 allows the three pullwires 208 to be transitioned from the respective lumens 210 of the distal articulating section 214 into the single stiffening tube 230 of the proximal shaft section 220 without having to spiral the pullwires 208 and corresponding lumens through the wall of the catheter tube 202, thereby allowing the thickness of the wall to be uniform and minimizing the possibility of weakened regions in the catheter tube 202 and possible inadvertent kinking.

With reference now to FIG. 17, an embodiment of another flexible and steerable elongate catheter 300 will be described. The catheter 300 is similar to the previously described catheter 100, with the exception that the catheter 300 is designed as a rapid exchange catheter, which is facilitated by the placement of the pullwires on one arcuate side of the proximal shaft section, and in particular, within the stiffening tube. The catheter 300 may be used in a robotic catheter assembly 358, which is similar to the robotic catheter assembly 18 illustrated in FIGS. 5 and 6, with the exception that the robotic catheter assembly 358 includes a guidewire manipulator 360 that is in a side-by-side arrangement with a leader catheter manipulator 362, as shown in FIG. 18, which is facilitated by the rapid exchange architecture of the catheter 300.

The design of the catheter 300 applies to a leader catheter of a telescoping catheter pair; e.g., a leader catheter 300 and outer guide sheath 36. With a pair of telescoping catheters, the therapy will usually be delivered through the outer catheter after the inner catheter has been removed. Therefore, the inner catheter does not need to have a lumen extending through its center the entire length of its shaft. The purpose of the outer catheter is to facilitate access to the site of interest and then to provide a stable, controllable (steerable) lumen to deliver a therapeutic device. Therefore, the outer catheter needs to have a lumen through the center the entire length of its shaft. The purpose of the inner catheter is to work in conjunction with the outer catheter and guide wire in a telescoping motion to inchworm the catheter system through the anatomy. This can be achieved by just having a short section at the distal end of the leader catheter supporting the guide wire, and allowing the remainder of the wire to run parallel to the leader catheter.

The catheter 300 generally includes an elongate catheter body 302, a working lumen 304 disposed through the entire length of the catheter body 302 for delivering one or more instruments or tools from the proximal end of the catheter body 302 to the distal end of the catheter body 302, a control ring 306 secured the distal end of the catheter body 302, a plurality of pullwires 308 housed within one or more lumens 310 extending through the catheter body 302, and a proximal adapter 301 (with associated spools or drums 303 to which the proximal ends of the pullwires 308 are coupled). The working lumen 304, control ring 306, pullwires 308, and pullwire lumens 310, and proximal adapter 301 may be constructed and function in a similar manner as the working lumen 104, control ring 106, pullwires 108, pullwire lumens 110, and proximal adapter 101 described above.

Like the catheter 100, the catheter 300 is functionally divided into four sections: a distal tip 312, a distal articulating section 314, a proximal shaft section 320, and a transition section 316. The distal tip 312 and distal articulating section 314 of the catheter 300 may be identical to the distal tip 112 and distal articulating section 114 of the catheter 100. The transition section 318 of the catheter 300 is identical to the transition section 116 of the catheter 100 with the exception that the transition section 316 includes a rapid exchange port 322 that is in communication with a guidewire lumen 304. The exact location of the rapid exchange port 322 relative to the distal tip of the catheter 300 can vary by varying the length of the distal articulating section 314 and transition section 316. Ultimately, the location of the rapid exchange port 322 will depend on the required distance that the catheter 300 needs to extend beyond the distal tip of the outer guide sheath 36. However, the rapid exchange port 322 should never exit the distal tip of the outer guide sheath 36—else it would be difficult to retract the distal end of the catheter 300 back into the outer guide sheath 36. Thus, the length of the over-the-wire segment of the catheter 300 (i.e., the total length of the distal tip 312, distal articulating section 314, and transition section 316) should always be greater than the maximum extension of the catheter 300 from the outer guide sheath 36. A shorter the over-the-wire segment length, however, will be easier and faster to use, because the robot may control more of the insertion and withdrawal of the catheter 300.

The proximal end of transition section 316 is tapered to provide a smooth rapid exchange port 322. This allows the guide wire 40 to be front-loaded through the proximal end of the outer guide sheath 36 and then exit out through the exit port (not shown) at the distal tip 312 of the catheter 300. The proximal shaft section 320 of the catheter 300 is composed of a stiffening tube 330, which is in communication with the pullwire lumens 310 via the transition section 316 (e.g., via use of the adapter 138 illustrated in FIGS. 8 and 9).

Thus, when the catheter 300 is used with the outer guide sheath 36, the guide wire 40 will travel outside the catheter 300 within the outer guide sheath 36, until it enters the rapid exchange port 322, and then through the guide wire lumen 304, and then out through the guide wire exit port. Thus, the catheter 300 and the guide wire 40 will travel parallel to each other through the outer guide sheath 36 until the guide wire 40 enters the rapid exchange port 322, after which they travel concentrically relative to each other. In addition, contrast agents can also be injected through a flush port (not shown) at the proximal end of the outer guide sheath 36, which may enter the rapid exchange port 322, and exit out the guide wire exit port.

The design of the rapid exchange leader catheter 300 allows for significantly greater robotic control of position. In particular, because the catheter 300 and guide wire 40 are not concentrically arranged relative to each other, but instead are two independent devices, at the proximal end of the assembly, greater independent robotic control is enabled without the need for an excessively long instrument driver. That is, the guidewire manipulator 360 can now be placed in a side-by-side arrangement with the leader catheter manipulator 362. The instrument driver has separate drive trains for the catheter 300 and guide wire 40, allowing the user to have full independent insertion and withdrawal control of both the catheter 300 and the guide wire 40 at all times. This results in less fluoroscopic time and radiation exposure, faster procedure time, greater length of robotic insertion and retraction of the catheter 300 and guide wire 40, less risk of losing guide wire position, less risk of breaching the sterile field, and allows for use of shorter guide wires and therefore one less person in the sterile field.

It should be appreciated that this rapid exchange design is applicable to other non-steerable catheters (e.g., atherectomy devices or graspers) that require the routing of wires from the proximal end to an operative element at the distal end of the catheter. The method of manufacturing the catheter 100 may be similar to the method of manufacturing the catheter 300 described above, with the exception that the proximal end of the transition section 316 is tapered, and the stiffening tube 330 forms the entirety of the catheter proximal shaft section 320 and is suitably bonded within the proximal end of the transition section 316.

One method of using the robotic catheter assembly 358 illustrated in FIG. 18 to access a diseased site within the vasculature of a patient will now be described. First, an incision in a blood vessel of the patient (e.g., a femoral artery) is made using a conventional techniques, and a starter wire is advanced into the artery. Next, the leader catheter 300 is preloaded into the outer guide sheath 36, ensuring that the rapid exchange port 322 remains inside the outer guide sheath 36. Then, the guide wire 40 is backloaded into the tip of the leader catheter 300. When the guide wire 40 exists the rapid exchange port 322, the guide wire 40 is advanced through the outer guide sheath 36 next to the leader catheter 300 until it exits at the back of the proximal adapter 48 of the outer guide sheath 36. Next, the guide wire 40 is held in a fixed position, while the leader catheter 300 is advanced several centimeters into the femoral artery over the guide wire 40. Then, the proximal adapter 301 of the leader catheter 300 and guide wire 40 are loaded onto the robotic instrument driver 34.

Then, the guide wire 40 and leader catheter 300 can be robotically driven remotely to the site of interest using the operator control station 16. If a selective angiogram is required when driving the guide wire 40 and leader catheter 300, a contrast agent may be injected through an injection port on the outer guide sheath 36. If the guide wire 40 is 0.035" in diameter and occupies most of the available space through the leader catheter, almost all of the contrast agent will exit the distal tip of the outer guide sheath 36. In contrast, if guide wire 40 is 0.018" in diameter, some of the contrast agent will exit out the distal tip of the leader catheter 300, and some of the contrast agent will exit out the distal tip of the outer guide sheath 36. Either way, the physician will be capable of obtaining a selective angiogram for the vessel of interest.

Once the guide wire 40 is at the site of interest, the physician may then robotically withdraw the leader catheter 300 until the "over-the-wire" section exits at the back of the proximal adapter 48 of the outer guide sheath 36. This can be accomplished without the use of fluoroscopy, since the robotic catheter system 358 will ensure that the position of the guide wire 40 relative to the patient is maintained. Depending on the robotic configuration used (i.e., the travel distance of the leader catheter carriage), this leader catheter 300 removal step may be accomplished entirely remotely or part manually and part robotically.

The physician may then manually remove the guide wire 40 from the guide wire manipulator 360, slide out the last few inches of the leader catheter 300 under fluoroscopy, and remove leader catheter 300 from the patient. A therapeutic device may then be manually delivered through the outer guide sheath 36. If the therapeutic device is itself a rapid exchange catheter, after the "over-the-wire" section has been manually passed into the outer guide sheath 36, the guide wire 40 may then be positioned back onto the guide wire manipulator 30, and the robot can be used to hold the position of the guide wire 40 while the therapeutic device is manually advanced. If the leader catheter 300 needs to be reinstalled to access another site of interest within the patient, it may be backloaded over the guide wire 40 until the guide wire 40 exits the rapid exchange port 322. The guide wire 40 may then be loaded onto the guide wire manipulator 360 and the leader catheter 300 is reinstalled on the instrument driver 34. The guide wire 40 and leader catheter 300 can then be robotically driven remotely to the new site of interest using the operator control station 16.

With reference now to FIG. 19, an embodiment of yet another flexible and steerable elongate catheter 400 will be described. The catheter 400 is similar to the previously described catheter 100, with the exception that the catheter 400 has multiple regions of articulation, and in particular, a distal region of articulation and a proximal region of articulation. The catheter 400 enables two regions of articulation by altering the axial stiffness, flexural stiffness, and torsional stiffness of the catheter body in very specific locations. The catheter 400 may be used in the robotic catheter assembly 18 illustrated in FIGS. 5 and 6.

The catheter 400 generally includes an elongate catheter body 402, which like the catheter body 102, may be comprised of multiple layers of materials and/or multiple tube structures that exhibit a low bending stiffness, while providing a high axial stiffness along the neutral axis. Also like the catheter 100, the catheter 400 further includes a working lumen 404 disposed through the entire length of the catheter body 402 for delivering one or more instruments or tools from the proximal end of the catheter body 402 to the distal end of the catheter body 402, a control ring 406 secured the distal end of the catheter body 402, a plurality of pullwires 408 housed within one or more lumens 410 extending through the catheter body 402, and a proximal adapter 401 (with associated spools or drums 403 to which the proximal ends of the pullwires 408 are coupled). The working lumen 404, control ring 406, pullwires 408, pullwire lumens 410, and proximal adapter 401 may be constructed and function in a similar manner as the working lumen 104, control ring 106, pullwires 108, pullwire lumens 110, and proximal adapter 101 described above.

The catheter 400 is functionally divided into five sections: a distal tip 412, a distal articulating section 414, a transition section 416, a proximal articulating section 418, and a proximal shaft section 420.

The distal tip 412 includes an atraumatic rounded tip portion 422, a control portion 424 in which the control ring 406 is mounted, and an exit port (not shown) in communication with the working lumen 404 and from which a working catheter or guidewire may extend distally therefrom. The distal tip 412 may be constructed and function in a similar manner as the distal tip 112 described above.

Like the distal articulating section 114, four pullwire lumens 410 are equally spaced in an arcuate manner (i.e., ninety degrees apart) within the distal articulating section 414 to allow the distal articulating section 414 to be articulated in an infinite number of directions within the same plane (effectively, providing two degrees of freedom: pitch and roll). In an alternative embodiment, another number of pullwires lumens 410, and thus, pullwires 408, can be used. For example, three pullwire lumens 410 can be equally spaced in an arcuate manner (i.e., one hundred twenty degrees apart). The distal articulating section 414 preferably allows for a moderate degree of axial compression and optimal lateral flexibility. The distal articulating section 414 includes a rigid portion 426 and an articulatable portion 428. The distal articulating section 414 may be constructed and function in a similar manner as the distal articulating section 114 described above, with the pullwire lumens 410 extending through the rigid portion 426 and articulatable portion 428 as unsupported cavities in which the four pullwires 408 are respectively disposed.

The transition section 416 transitions the equal spacing of the lumens 410 in the distal articulating section 414 too close spacing of the lumens 410 in the proximal articulating section 418. Instead of using an adapter 138, as illustrated in FIGS. 8 and 9, the lumens 410 in the transition section 416 are gradually displaced about the axis of the catheter body 402 within the wall of the transition section 416. In particular, the one lumen 410 that is on the same side as the closely spaced lumens 410 in the proximal articulating section 418 may extend linearly along the length of the transition section 416, while the remaining three lumens spiral around the length of the transition section 416 until they converge onto the same side of the proximal articulating section 418. The transition section 416 is more rigid than the distal articulating section 414 to allow the distal articulating section 414 to bend about the transition section 416.

The transition section 416 resists axial compression to clearly define the proximal end of the distal articulating section 414 and transfer the motion of the pullwires 408 to the distal articulating section 414, while maintaining lateral flexibility to allow the catheter 400 to track over tortuous anatomies. In one embodiment, the transition section 416 is 33 mm in length. The pullwire lumens 410 extending through the transition section 416 take the form of 0.007"×0.009" polyimide tubes circumferentially oriented relative to each other by ninety degrees, and thus, can be considered stiffening members in which the pullwires 408 are respectively disposed. The entire working lumen 404 within the transition section 416 is formed by an inner polymer tube (e.g., 0.001" thick PTFE). The transition section 416 has a several portions of differing rigidities formed by having different polymer outer tubes. In one embodiment, the transition section 416 includes a 1 mm pullwire lumen anchoring portion 430 having a relatively rigid outer polymer tube (e.g., Nylon-12) that increases the support for holding the distal ends of the polyimide pullwire lumens 410. The transition section 416 further includes a 4 mm flexible portion 432 having a relatively flexible outer polymer tube (e.g., Pebax® 40D) that transitions from the relatively flexible distal section 314 to a 28 mm stiff portion 434 having a relatively stiff outer polymer tube (e.g., Pebax® 55D).

To increase its axial rigidity, the transition section 416 comprises a double braided layer (e.g., sixteen 0.0005"×0.003" spring temper 304V stainless steel wires braided at 140 ppi in a 2 over 2 pattern) embedded within the outer polymer tubes of all three of the anchoring portion 430, flexible portion 432, and rigid portion 434. Three of the polyimide pullwire lumens 410 spiral around the stiff portion 434 of the transition section 416, which along with the remaining polyimide pullwire lumen 410, converge to the same side of the catheter body 402.

The proximal articulating section 418 significantly allows for a moderate degree of axial compression and optimal lateral flexibility. The pullwire lumens 410 are grouped on one arcuate side of the proximal articulating section 418 to allow it to be articulated in one direction. Preferably, the pullwire lumens 410 are grouped in a manner that locates their centers within an arcuate angle relative to the geometric cross-sectional center of the proximal shaft section of less than one hundred eighty degrees, and more preferably, less than ninety degrees, and most preferably, less than forty-five degrees.

In one embodiment, the proximal articulating section 418 is 16 mm in length. Preferably, the proximal articulating section 418 is more rigid than the distal articulating section 414, such that independent control of the distal articulating section 414 and the proximal articulating section 418 can be achieved, as discussed in further detail below. Like in the transition section 416, the pullwire lumens 410 extending through the proximal articulating section 418 take the form of 0.007"×0.009" polyimide tubes, and thus, can be considered stiffening members in which the pullwires 408 are respectively disposed. The entire working lumen 404 within the proximal articulating section 418 comprises an inner polymer tube (e.g., 0.001" thick PTFE). The proximal articulating section 418 has two portions of differing rigidities formed by having different polymer outer tubes. In one embodiment, the proximal articulating section 418 includes a 15 mm articulatable portion 436 having a relatively flexible outer polymer tube (e.g., Pebax® 40D) and a 1 mm pullwire lumen anchoring portion 438 having a relatively rigid polymer tube (e.g., Nylon) that increases the support for holding the polyimide pullwire lumens 410. To increase its axial rigidity and elastic properties, the proximal articulating section 418 comprises a double braided layer (e.g., sixteen 0.0005"×0.003" spring temper 304V stainless steel wires braided at 140 ppi in a 2 over 2 pattern) embedded within the outer polymer tubes.

The proximal shaft section 420 resists axial compression to clearly define the proximal end of the proximal articulating section 418 and transfer the motion of the pullwires 408 to the proximal articulating section 314, while maintaining lateral flexibility to allow the catheter 400 to track over tortuous anatomies. Like with the proximal articulating section 314, the pullwire lumens 410 are grouped on one arcuate side of the proximal shaft section 420. Because the pullwire lumens 410 are more rigid than the remaining material of the proximal articulating section 418 (i.e., the pullwire lumens 410 are composed of a polyimide, whereas the remaining portion of the proximal articulating section 418 is composed of a low durometer polymer composite), the neutral axis will be shifted closer to the axis of the grouping of pullwire lumens 410, thereby providing the aforementioned advantages discussed above with respect to the catheter 100.

The proximal shaft section 420 represents the majority of the length of the catheter 400, and gradually transitions the catheter 400 from the more flexible proximal articulating section 418 to the more rigid remaining portion of the catheter 400. For example, the proximal shaft section 420 may include three proximal portions 440, 442, 444 that increase in rigidity in the proximal direction. The proximal shaft section 420 may be constructed and function in a similar manner as the proximal shaft section 120 described above.

Having described its function and construction, one method of manufacturing the catheter 400 will now be described. Like the method of manufacturing the catheter 100, in this method, the distal articulating section 414 and the combined proximal articulating section 418/proximal shaft section 420 are fabricated separately, and then mounted to each other when the transition section 416 is fabricated. The distal tip 412 can then be formed onto the assembly to complete the catheter 400.

The distal articulating section 414 can be fabricated in the same manner as the distal articulating section 114 described above. The proximal articulating section 418 and proximal shaft section 420 are fabricated together by first inserting a copper wire process mandrel through a lumen of an inner polymer tube (e.g., a PTFE extrusion) having the intended length of the combined proximal articulating section 418/proximal shaft section 420. Then, using a conventional braiding machine, a first layer of braiding is laid down over the length of the inner polymer tube. Next, four PTFE-coated stainless steel wire process mandrels with polyimide tubing are respectively disposed over the length of the braided inner polymer tube in a group on one side of the inner polymer tube, and a second layer of braiding is laid down over the four wire process mandrels the length of the inner polymer tube. Next, outer polymer tubes having different durometers and lengths corresponding to the lengths of the different portions of the proximal articulating section 418 and the proximal shaft section 420 (e.g., a Pebax® 40D extrusion for the articulatable portion 436 and a Nylon-12 extrusion for the anchoring portion 438 of the proximal articulating section 418, and Pebax® 55D, Pebax® 72D, and Nylon-12 extrusions for the respective proximal portions 440, 442, 444 of the proximal shaft section 420) are slid over the fully braided inner polymer tube, and then heat shrink tubing is slid over the outer polymer tubes.

The assembly is then heated to a temperature above the melting temperature of the outer polymer tubes, but below the melting temperature of the heat shrink tubing. As a result, the outer polymer tubes melt and flows, while the heat shrink tubing shrinks and compresses the melted outer polymer tubes into the braid and around the four stainless steel process mandrels. The assembly then cools and solidifies to integrate the inner polymer tube, braid, and outer polymer tubes together. Then, the center copper wire can be pulled from the assembly to create the working lumen 404, and the four stainless steel wires can be pulled from the assembly, thereby leaving the polyimide tubing with the assembly to respectively create the four pullwire lumens 410.

Next, the distal articulating section 414 and the combined proximal articulating section 418/proximal shaft section 420 are coupled to each other by fabricating the transition section 416 between the distal articulating section 414 and the combined proximal articulating section 418/proximal shaft section 420. In particular, the transition section 416 is partially fabricated by first inserting a PTFE-coated copper wire process mandrel through a lumen of an inner polymer tube (e.g., a PTFE extrusion) having the intended length of the transition section 416. Then, using a conventional braiding machine, a first layer of braiding is laid down over the length of the inner polymer tube. Then, each of four PTFE-coated stainless steel wire process mandrels is inserted through a lumen of a polyimide tube having the intended length of the transition section 416. The linear length of one of these wire process mandrels will equal the length of the transition section 416, while the linear lengths of the remaining three wire process mandrels will be slightly greater than the length of the transition section 416 to compensate for the additional length required to spiral these wire process mandrels around the transition section 416.

Next, the opposing ends of the center wire process mandrel are respectively inserted through the working lumens 404 of the distal articulating section 414 and the combined proximal articulating section 418/proximal shaft section 420, and the opposing ends of four wire process mandrels are inserted through the pullwire lumens 410 of the distal articulating section 414 and the pullwire lumens 410 of the combined proximal articulating section 418/proximal shaft section 420. The distal articulating section 414 and the combined proximal articulating section 418/proximal shaft section 420 are then slid together until the inner polymer tube of the transition section 416 abuts the inner polymer tubes of the distal articulating section 414 and the proximal articulating section 418, and the polyimide tubing on the four wire process mandrels abuts the pullwire lumens 410 of the distal articulating section 414 and the pullwire lumens 410 of the proximal articulating section 418. Three of the wire process mandrels are then spiraled around and bonded to the inner polymer tube, and a second layer of braiding is laid down over the four wire process mandrels the length of the inner polymer tube.

Next, outer polymer tubes having different durometers and lengths corresponding to the lengths of the different portions of the transition section 416 (e.g., a Nylon-12 extrusion for the anchoring portion 430, a Pebax® 40D extrusion for the flexible portion 432, and a Pebax® 55D extrusion for the rigid portion 434) are slid over the fully braided inner polymer tube, and then heat shrink tubing is slid over the outer polymer tubes. The assembly is then heated to a temperature above the melting temperature of the outer polymer tubes, but below the melting temperature of the heat shrink tubing. As a result, the outer polymer tubes melt and flows, while the heat shrink tubing shrinks and compresses the melted outer polymer tubes into the braid and around the four stainless steel process mandrels. The assembly then cools and solidifies to integrate the inner polymer tube, braid, and outer polymer tubes together. Then, the center copper wire can be pulled from the assembly to create the working lumen 404 within the transition section 416, and the four stainless steel wires can be pulled from the assembly, thereby leaving the polyimide tubing within the assembly to respectively create the four pullwire lumens 410 within the transition section 416.

The control ring 406, pullwires 408, and distal tip 412 may be installed on the assembly in the same manner as the control ring 106, pullwires 108, and distal tip 112 described above. Alternatively, in a similar manner discussed above, instead of utilizing a control ring 106, the distal ends of the pullwires 108 may be attached directly to a section or portion of the catheter body 102 where it may be steered, articulated, or bent, and in this case, to the distal end of the distal articulating section 414.

Significantly, the catheter 400 may be operated in a manner that independently controls the articulation of the distal articulating section 414 and proximal articulating section 418. The theory behind the design of the catheter 400 is that if only one pullwire 408 is tensioned, only the distal articulating section 414 will bend. If all four pullwires 408 are uniformly tensioned (common mode), then only the proximal articulating section 418 will bend. Any variation in wire tension from these two scenarios will result in the bending of both the distal articulating section 414 and proximal articulating section 418 assuming at least two of the pullwires 408 are tensioned. Effectively, the distal articulating section 414 provides the catheter 400 with two degrees of freedom (bend and roll), and the proximal articulating section 418 provides the catheter 400 with one degree of freedom (bend).

In particular, when two or less of the pullwires 408 are tensioned at relatively small amount, the distal articulating section 414 articulates in the direction of the tensioned pullwire(s) 310. Because the proximal articulating section 418 is designed to be more laterally rigid than the distal articulating section 414, the net moment created at the distal tip 412 nominally articulates only the distal articulating section 414, but is not sufficient to overcome the lateral stiffness of the proximal articulating section 418 in a manner that would cause a significant bend in the proximal articulating section 418. This feature therefore facilitates independent articulation of the distal articulating section 414 relative to the proximal articulating section 418 even through the pullwires used to articulate the distal articulating section 414 extend through the proximal articulating section 418.

When all four of the pullwires 408 are uniformly tensioned, there will be no net moment created at the distal tip 412 due to the equal arcuate distribution of the pullwires 408 at the distal tip 412. As such, the distal articulating section 414 will not articulate. However, because all four of the pullwires 408 are grouped together on one side of the proximal articulating section 418, a net moment is created at the distal end of the proximal articulating section 418. As such, the proximal articulating section 418 will articulate in the direction of the grouped pullwires 408. This feature therefore facilitates independent articulation of the proximal articulating section 418 relative to the distal articulating section 414 even through the pullwires used to articulate the proximal articulating section 418 extend through the distal articulating section 414.

When two or less than the pullwires 408 are tensioned a relatively large amount, and the remaining pullwires 408 are also tensioned but not as much as the initially tensioned pullwires 408 are tensioned, then the net moment is created at the distal tip 412 greatly articulates the distal articulating section 414 in the direction of the initially tensioned pullwire(s) 410, while the combined moment created at the distal end of the proximal articulating section 418 moderately articulates the proximal articulating section 418 in the direction of the grouped pullwires 408, thereby causing a large bend in the distal articulating section 414 while causing a small bend in the proximal articulating section 418.

When two or less of the pullwires 408 are tensioned a relatively small amount, then all of the pullwires 408 are uniformly tensioned an additional amount, a net moment is created at the distal tip 412 to moderately articulate the distal articulating section 414 in the direction of the tensioned pullwire(s) 410, while the additional tensioning of all of the pullwires 408 greatly articulates the proximal articulating section 418, thereby causing a small bend in the distal articulating section 414 while causing a large bend in the proximal articulating section 418.

The computer 28 within the control station 16 may be programmed with algorithms that take into account the elastic behavior of the distal articulating section 414 and proximal articulating section 418 and catheter stiffness when computing the displacements of the pullwires 408 required to enable complete and independent control of both the distal articulating section 414 and proximal articulating section 418.

By achieving independent articulation control over the distal articulating section 414 and the proximal articulating section 418, anatomical sites of interest can be more easily accessed. The catheter 400 can be used to access either the left coronary artery or the right coronary artery from the aorta of the patient.

Figure 20:
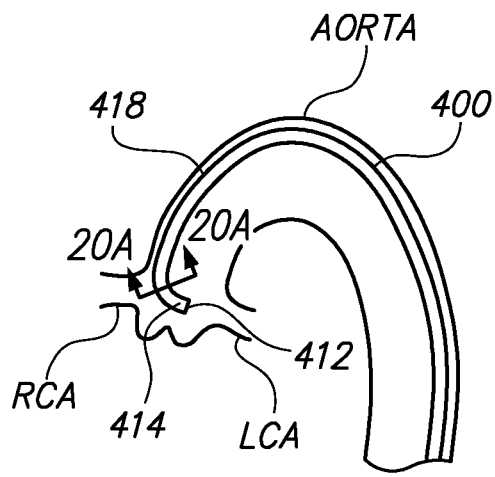
FIGS. 20 and 21 are plan views showing one method of accessing the left coronary artery of an anatomy using the catheter of FIG. 19.
Figure 20A:
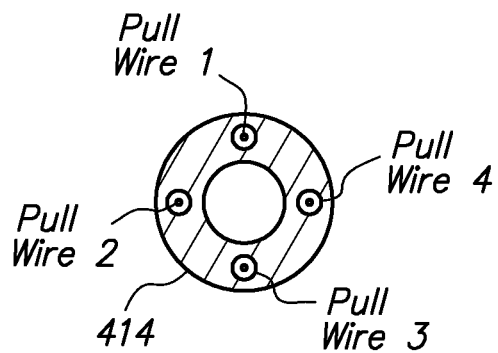
FIG. 20A is a cross-sectional view of the distal articulating region of the catheter shown in FIG. 20, respectively taken along the line 20A-20A.
Figure 21:
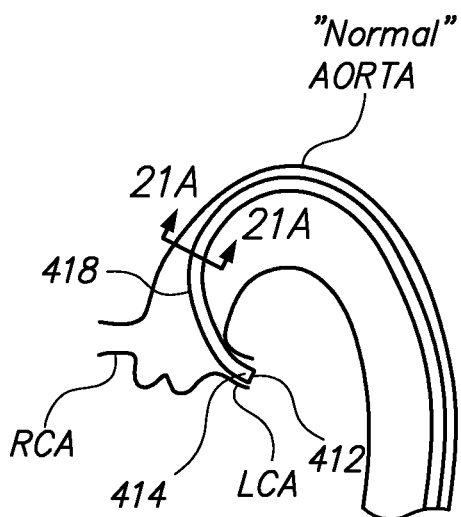
Figure 21A:
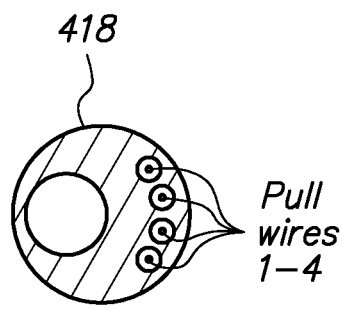
FIG. 21A is a cross-sectional view of the proximal articulating region of the catheter shown in FIG. 21, respectively taken along the line 21A-21A.

To access the left coronary artery, the pullwire or pullwires 408 in the direction of the left coronary artery (in this case, pullwire 1) can be tensioned to bend the distal articulating section 414 ninety degrees towards the left coronary artery, as illustrated in FIG. 20. Then, all four of the pullwires 408 can be tensioned an additional amount to bend the proximal articulating section 418 to seat the distal tip 412 of the catheter 400 within the ostium of the left coronary artery, as shown in FIG. 21. For example, if the pullwire 1 is initially tensioned at a force of 7 units to bend the distal articulating section 414, an additional force of 3 units can be used to tension all four pullwires 1-4 (resulting in a 10 unit tension in pullwire 1, and a 3 unit tension in pullwires 2-4). There is now 19 units of force on the proximal articulating section 418, which is adequate to bend the proximal articulating section 418. But there remains a delta of 7 units of tension more on pullwire 1 than on all other wires, and therefore there is no further bending of the distal articulating section 414.

Figure 22:
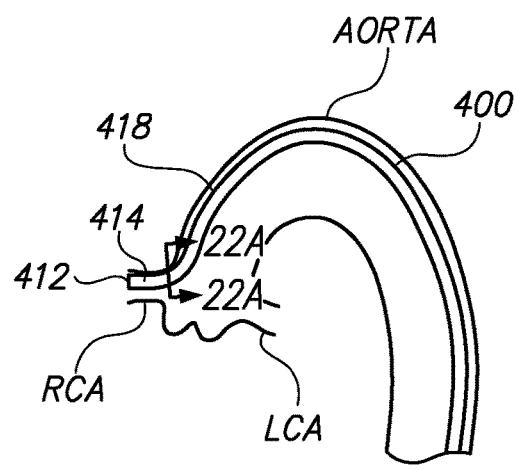
FIGS. 22 and 23 are plan views showing one method of accessing the right coronary artery of an anatomy using the catheter of FIG. 19.
Figure 22A:
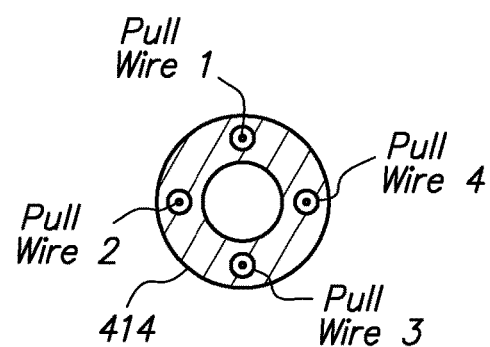
FIG. 22A is a cross-sectional view of the distal articulating region of the catheter shown in FIG. 20, respectively taken along the line 22A-22A.
Figure 23:
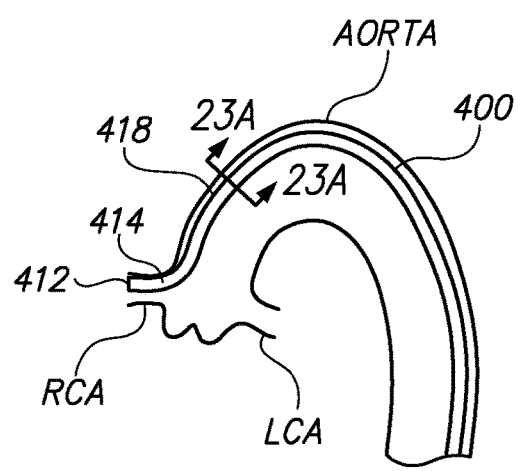
Figure 23A:
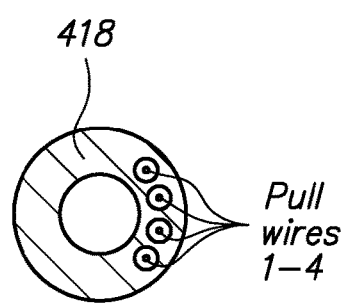
FIG. 23A is a cross-sectional view of the proximal articulating region of the catheter shown in FIG. 23, respectively taken along the line 23A-23A.

To access the right coronary artery, the pullwire or pullwires 408 in the direction of the right coronary artery (in this case, pullwire 4) can be tensioned to bend the distal articulating section 414 ninety degrees to seat the distal tip 412 within the ostium of the right coronary artery, as illustrated in FIG. 22. If the distal tip 412 is seated too deeply within the ostium of the right coronary artery, then all four of the pullwires 408 can be tensioned an additional amount to bend the proximal articulating section 418 to properly seat the distal tip 412 within the ostium of the right coronary artery, as shown in FIG. 23. For example, if the pullwire 4 is initially tensioned at a force of 7 units to bend the distal articulating section 414, an additional force of 1 unit can be used to tension all four pullwires 1-4 (resulting in an 8 unit tension in pullwire 1, and a 1 unit tension in pullwires 2-4) to slightly bend the proximal articulating section 418.

Figure 24A:
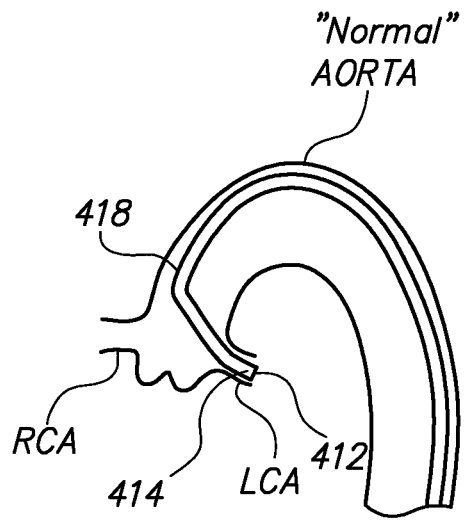
FIGS. 24A-24C are plan views showing methods of accessing the left coronary arteries of different anatomies using the catheter of FIG. 19.
Figure 24B:
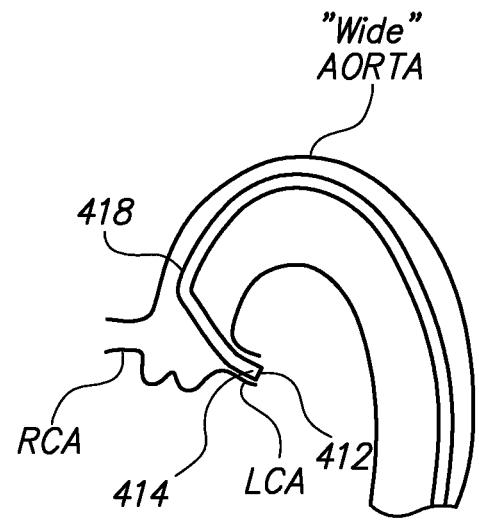
Figure 24C:
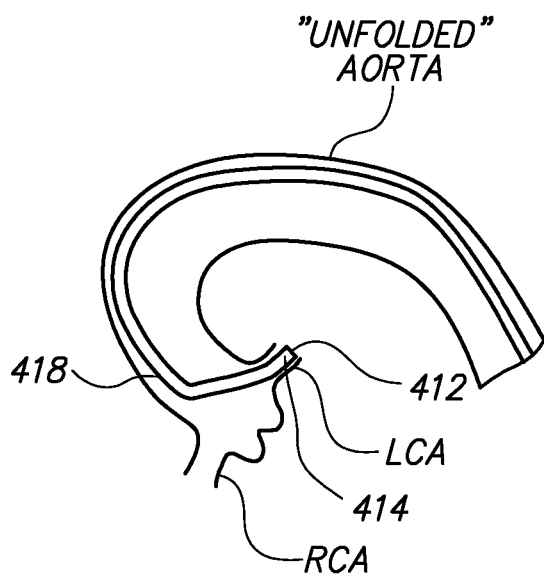

As another example, by independently articulating the catheter 400, the left coronary artery of a patient can be accessed regardless of the type of anatomy. In particular, FIG. 24A illustrates independent articulation of the proximal articulating section 418 and distal articulating section 414 of the catheter 400 to access the left coronary artery in a "normal" anatomy; FIG. 24B illustrates independent articulation of the proximal articulating section 314 and distal articulating section 418 of the catheter 400 to access the left coronary artery in a "wide" anatomy; and FIG. 24C illustrates independent articulation of the proximal articulating section 418 and distal articulating section 414 of the catheter 400 to access the left coronary artery in an "unfolded" anatomy.

Significantly, by taking advantage of the geometric construction and variation in catheter flexibility to achieve independent control over multiple articulation segments, several advantages are achieved using the catheter 400. First, repeatable and consistent articulation performance at two unique locations in the catheter 400 can be achieved. Second, while other dual articulating catheters achieve independent control over multiple articulation segments by employing multiple control rings and having dedicated pullwire or articulation mechanisms, the catheter 400 does not require a second control ring or dedicated control mechanism to effect a second articulation within the catheter, but rather only utilizes the distal-most control ring and the pullwires that are already installed for the distal articulation of the catheter. Thus, by eliminating the need for a second control ring and a separate set of pullwires, few components are needed. Third, the need for a procedure to fasten a second set of wires to a second control ring is eliminated, thereby decreasing the cost of manufacturing the catheter. Fourth, an existing driver instrument initially designed for a catheter having a single region of articulation (e.g., the catheter 100 or catheter 400) can be utilized for a catheter having dual regions of articulation (e.g., the catheter 400), since no additional pullwires are needed, and thus the proximal adapter of the catheter remains the same. It should also be noted that robotic control of the catheter 400 efficiently and quickly manages the tensioning of the pullwires to effect the articulation of the catheter 400, and therefore, there is no need for the physician to think about which of the pullwires to tension and the magnitude of the tension to be placed on the pullwires.

With reference now to FIG. 25, an embodiment of yet another flexible and steerable elongate catheter 500 will be described. The catheter 500 is similar to the previously described catheter 400, with the exception that the catheter 400 has a proximal region of articulation that bi-directionally bends in a plane. The catheter 500 may be used in the robotic catheter assembly 18 illustrated in FIGS. 5 and 6.

The catheter 500 generally includes an elongate catheter body 502 (which may have any suitable cross-section, such as circular or rectangular), which like the catheter body 502, may be comprised of multiple layers of materials and/or multiple tube structures that exhibit a low bending stiffness, while providing a high axial stiffness along the neutral axis. Also, like the catheter 400, the catheter 500 further includes a working lumen 504 disposed through the entire length of the catheter body 502 for delivering one or more instruments or tools from the proximal end of the catheter body 502 to the distal end of the catheter body 502, a control ring 506 secured the distal end of the catheter body 502, a plurality of pullwires 508 housed within one or more lumens 410 extending through the catheter body 502, and a proximal adapter 501 (with associated spools or drums 503 to which the proximal ends of the pullwires 508 are coupled). The working lumen 504, control ring 506, pullwires 508, pullwire lumens 510, and proximal adapter 501 may be constructed and function in a similar manner as the working lumen 404, control ring 406, pullwires 408, pullwire lumens 410, and proximal adapter 401.

The working lumen 504, control ring 506, pullwires 508, and pullwire lumens 510 may be constructed and function in a similar manner as the working lumen 404, control ring 406, pullwires 408, and pullwire lumens 410 described above, except that one of the pullwires 508 is used to provide proximal bi-directional articulation.

In particular, as previously stated, tensioning one or more of the pullwires 408 in the catheter 400 may cause the proximal articulating section 418 to bend somewhat. Such proximal bend can be increased by uniformly increasing the tension in the pullwires 408, but cannot be decreased. Thus, the proximal articulating section 418 can only bend in a single direction (i.e., in the direction of the grouped pullwires 408).

In contrast, the catheter 500 utilizes a counteracting pullwire 508' that circumferentially opposes the group of pullwires 508 in the proximal articulating section, such that tensioning the counteracting pullwire 508 bends the proximal articulating section in one direction, while uniformly tensioning the three remaining pullwires 508 bends the proximal articulating section in an opposite direction. Notably, an existing driver instrument initially designed for a catheter having four pullwires for a single region of articulation (e.g., the catheters 100, 200, and 300) or a distal region of articulation and a proximal region of uni-directional articulation (e.g., the catheter 400) can be utilized for a catheter having a distal region of articulation (using 3 of the pullwires) and a proximal region of bi-directional articulation with the remaining wire (e.g., the catheter 500), since no additional pullwires are needed, and thus the proximal adapter of the catheter remains the same.

The catheter 500 is functionally divided into five sections: a distal tip 512, a distal articulating section 514, a transition section 516, a proximal articulating section 518, and a proximal shaft section 520.

The distal tip 512 is identical to the distal tip 412, and the distal articulating section 514 is identical to the distal articulating section 414 of the catheter 400, with the exception that three pullwire lumens 510 (rather than four), and thus, three pullwires 508, are equally spaced in an arcuate manner (i.e., one hundred twenty degrees apart) within the distal articulating section 514 to allow it to be articulated in an infinite number of directions within the same plane (effectively, providing two degrees of freedom: bend and roll).

The transition section 516 is identical to the transition section 416 of the catheter 400, with the exception that the distal end of the counteracting pullwire 508' is anchored within the proximal end of the transition section 516, and the three remaining pullwire lumens 510 and associated pullwires 508 are equally spaced in an arcuate manner (i.e., one hundred twenty degrees apart).

The proximal articulating section 518 is identical to the proximal articulating section 418 of the catheter 500, with the exception that the counteracting pullwire 508' is oriented one hundred eighty degrees from the group of the remaining three pullwires 508, and the counteracting pullwire lumen 510' in which the counteracting pullwire 508' is disposed takes the form of an unsupported cavity. The proximal shaft section 520 is identical to the proximal shaft section 420 of the catheter 400, which has the feature of shifting the neutral axis closer to the axis of the grouping of pullwire lumens 510, thereby providing the aforementioned advantages discussed above with respect to the catheter 100.

The method of manufacturing the catheter 500 is the same as the method of manufacturing the catheter 500 described above, with the exception that the distal end of the counteracting pullwire 508' is anchored within the pullwire lumen 510' in the proximal end of the transition section 516, and the pullwire lumen 510' is unsupported through the transition section 516 and the proximal articulating section 518 until it reaches the distal end of the proximal shaft section 520, at which point it is composed of a polyimide tube that is grouped with the remaining three polyimide lumens 510. The counteracting pullwire 508' may be anchored in the proximal end of the transition section 516 by using another control ring or anchoring it directly to braid.

Like with the catheter 500, the computer 28 within the control station 16 (shown in FIG. 4) may be programmed with algorithms that take into account the elastic behavior of the distal articulating section 514 and proximal articulating section 518 and catheter stiffness when computing the displacements of the pullwires 508 required to enable complete and independent control of both the distal articulating section 514 and proximal articulating section 518. To fully utilize the multi-bend architecture of the catheter 500, it is important for the physician to independently control the distal articulating section 514 and proximal articulating section 518. However, because the any distal moment created at the distal tip 512 of the catheter 500 will cause bending of the proximal articulating section 518 as small as it may be, the computer 28 employs a multi-bend control algorithm that takes into account the inadvertent bending of the proximal articulating section 518 in order to ensure full independent articulation of the distal articulating section 514 and the proximal articulating section 518. Ideally, when only bending of the distal articulating section 514 is desired, the proximal articulating section 518 should not bend, and when only bending of the proximal articulating section 518 is desired, the distal articulating section 514 should not bend.

Figure 26:
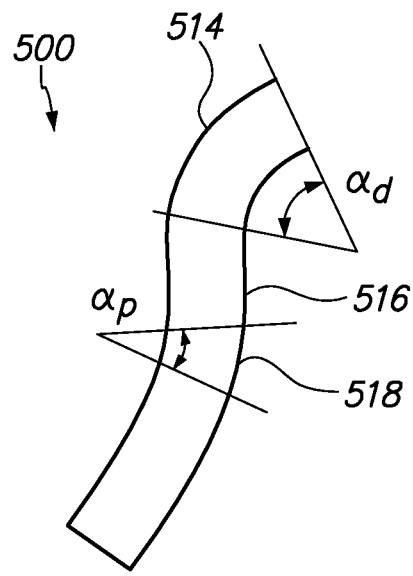
FIG. 26 is a plan view of a multi-bend segment of the catheter of FIG. 25, particularly showing a distal articulation angle and a proximal articulation angle.

With reference to FIG. 26, a multi-bend segment of the catheter 500 is shown having a distal articulation angle $\alpha_d$ and a proximal articulation angle $\alpha_p$. The multi-bend segment of the catheter also has a distal articulation roll $\theta$. Thus, the catheter 500 has two articulation Degrees of Freedom (DOFs) in the distal bend and a single articulation DOF in the proximal bend. From a controls perspective, the transition section 516 of the catheter 500 couples the distal articulating section 514 and the proximal articulating section 518 in such a way that the coupling can be counteracted by the counteracting pullwire 508'. The multi-bend control algorithm employed by the computer 28 utilizes this configuration to independently control the bends in the distal articulating section 514 and the proximal articulating section 518.

The following relation can be used to calculate the number of independently controllable DOFs (m) in a catheter based on the number of pullwires (n):

$$m \leq n-1 \quad [1]$$

Figure 27:
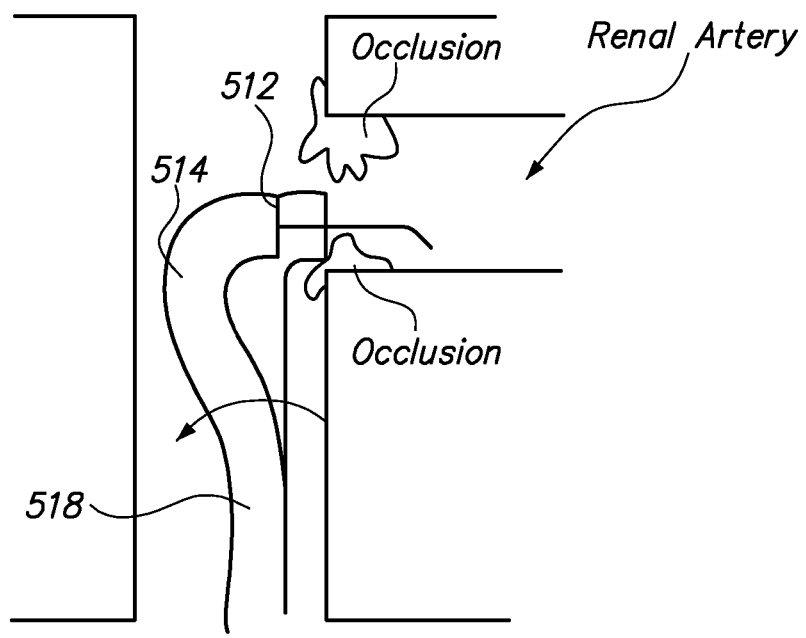
FIG. 27 is a plan view showing a method of accessing a renal artery using the catheter of FIG. 25.

Thus, the four pullwires 508 of the catheter 500 can be used to independently control three DOFs, in particular, the distal articulation angle $\alpha_d$, proximal articulation angle $\alpha_p$, and distal articulation roll $\theta$. These DOFs allow the orientation and position of the distal tip 512 of the catheter 500 to be controlled by the distal articulating section 514, then fine-tuned via the proximal articulating section 518. One example of the catheter's utility is the procedure for cannulating the renal artery when an occlusion is located at the ostium, as shown in FIG. 27. In this case, the physician would bend the distal articulating section 514 to orient the distal tip 512 towards the ostium, while bending the proximal articulating section 518 to ensure that the distal tip 512 does not contact the occlusion.

The multi-bend algorithm leverages the counteracting pullwire 508' and the common mode (uniformly tensioning the remaining three pullwires 508) to independently control the distal articulating section 514 and proximal articulating section 518. In particular, with reference to FIG. 28, the multi-bend algorithm that maps articulation commands ($\alpha_d$, $\theta$, and $\alpha_p$) to pullwire distances $\vec{w}$ will be described.

The commanded distal articulations $\alpha_d$ and $\theta$ are mapped to distal pullwire distances $\vec{w}_d$ through a distal articulating section solid mechanics model. The three pullwires 508 fastened to the control ring 506 are used to produce the desired bend at the distal articulating section 514. Based on the commanded distal articulations $\alpha_d$ and $\theta$, a bending force is computed using a constant moment assumption, as disclosed in D. B. Camarillo, C. F. Milne, C. R. Carlson, M. R. Zinn, and J. K. Salisbury; Mechanics Modeling of Tendon-Driven Continuum Manipulators; IEEE Transaction on Robotics, 24(6): 1262-1273 (2008). A series spring model of the catheter is then used to compute the distal pullwire distances $\vec{w}_d$ that will produce the desired moment. However, the computed distal pullwire distances $\vec{w}_d$ may be negative, which is not physically feasible, since this indicates that the pullwires 508 must be pushed. Thus, a null space of control is added to the distal pullwire distances $\vec{w}_d$ until all distal pullwire distances $\vec{w}_d$ are positive. For the distal articulating section 514, the null space involves adding the same pullwire distance to all three pullwires 508, which does not modify the distal articulations $\alpha_d$ and $\theta$.

These pullwire distances $\vec{w}_d$ are input to a proximal motion predictor that produces an expected proximal articulation angle $\tilde{\alpha}_p$. There are two effects: a distal moment effect and a common mode effect, that contribute to the expected proximal articulation angle $\tilde{\alpha}_p$ based on the pullwire distances $\vec{w}_d$. With respect to the distal moment effect, when a distal pullwire is tensioned, a moment is applied at the control ring 506. Based on the constant moment assumption disclosed in D. B. Camarillo, this moment is transferred to the proximal articulating section 518. With respect to the common mode effect, when one of the non-straight pullwires 508 (i.e., spiraled around the transition section 516) is tensioned, the path of the pullwire 508 through the transition section 516 causes a moment M to be applied to the transition section 516 in the direction of the side of the catheter on which the pullwires 508 are grouped, as best illustrated in FIG. 29. This moment M causes the proximal articulating section 518 to bend in the direction of the grouped pullwires 508. To decouple the proximal and distal bend motions from each other, both of these effects must be taken into account.

The expected proximal articulation angle $\tilde{\alpha}_p$ due to the distal moment effect can be computed by applying the material properties of the proximal articulating section 518 to the basic moment-bending relation:

$$\tilde{\alpha}_p = \frac{M_d \cdot L_p}{K_p}, \quad [2]$$

where $M_d$ is the moment applied to the control ring 506, $L_p$ is the length of the proximal articulating section 518, and $K_p$ is the bending stiffness of the proximal articulating section 518.

The magnitude of the common mode effect depends upon the path of the non-straight pullwires 508 through the transition section 516. To understand this effect, it should be noted that the lowest energy configuration for a pullwire of a given unloaded length under tension between two points is a straight path. However, the non-straight pullwires have non-zero curvature, and will exert forces on the catheter 500 based on the magnitude of the curvature. These forces can be integrated to calculate an equivalent force and moment that a non-straight pullwire applied to the transition section 516 based on wire tension. Integrating the forces along the wire paths in the transition section 516 shows that the wire curvatures exert no net force and a moment proportional to the wire tension. As a result, a pure moment is transferred from the stiff transition section 516 to the flexible proximal articulating section 518, causing a constant-curvature proximal bend.

The magnitude of this moment $M_t$ can be modeled by a gain $K_t$ on the wire tension $F_w$ in a non-straight pullwire, as follows:

$$M_t = K_t F_w \quad [3]$$

The gain $K_t$ can either be derived from a path integral over the geometry of a given pullwire, or tuned empirically to experimentally dial in a stiffness or gain. Since the transition section 516 is relatively rigid, the pullwire geometry in this section does not change and the gain $K_t$ remains constant.

The estimated proximal articulation angle $\tilde{\alpha}_p$ due to the common mode effect can be computed by applying the material properties of the proximal articulating section 518 to the basic moment-bending relation:

$$\tilde{\alpha}_p = \frac{M_t \cdot L_p}{K_P} \quad [4]$$

The total proximal articulation angle due to the pullwire distances $\vec{w}_d$ can be obtained by combining equations [2]-[4], as follows:

$$\tilde{\alpha}_p = \frac{[Md + \Sigma_i K t^{(i)} F w^{(i)}] L p}{K_p} \quad [5]$$

The summation in the numerator of equation [5] operates over all transition section gains $Kt^{(i)}$ and $Fw^{(i)}$ corresponding to the bent pullwires/=1, 2, .... The estimated proximal articulation angle $\tilde{\alpha}_p$ is then subtracted from the commanded proximal articulation $\alpha_p$ to produce the amount of additional proximal articulation angle $\alpha_p^+$ required to achieve the command using the relation:

$$\alpha_p^+ = \alpha_p - \tilde{\alpha}_p \quad [6]$$

The pullwire distance $\vec{w}_p$ required to achieve the additional proximal articulation angle $\alpha_p^+$ is computed by using a proximal articulating section solid mechanics model. The pullwire distance $\vec{w}_p$ is different based on the direction of the articulation.

That is, if the additional proximal articulation angle $\alpha_p^+$ is positive (toward the pullwire grouping), then an additional common mode is commanded by tensioning each of the distal pullwires 508 by the same distance:

$$w_p = K_{cm} \alpha_p^+ \quad [7],$$

where $K_{on}$ is a gain that can be set empirically, or can be derived from the transition section gain $K_t$ and proximal articulating section material properties.

If the additional proximal articulation angle $\alpha_p^+$ is negative (away from the pullwire grouping), then the counteracting pullwire 108' is tensioned to achieve the articulation.

The distal pullwire distances $\vec{w}_d$ and proximal pullwire distances $\vec{w}_d$ are summed to produce the final set of pullwire distances $\vec{w}$.

By achieving independent articulation control over the distal articulating section 514 and the proximal articulating section 518 using the proximal pullwire 108', greater control when accessing anatomical sites of interest. For example, the distal pullwire or pullwires 508 in the direction of the right coronary artery (in this case, pullwire 3) can be tensioned to bend the distal articulating section 514 ninety degrees to attempt to seat the distal tip 512 within the ostium of the right coronary artery, as illustrated in FIG. 30A. However, the tension on the distal pullwire(s) 408 will create a moment at the proximal articulating section 518, and without proper compensation, may cause the proximal articulating section 518 to inadvertently bend in a manner that pulls the distal tip 512 away from the right coronary artery ostium. By tensioning the proximal pullwire 508', the proximal articulating section 518 may be bent back towards the right coronary artery ostium to properly seat the distal tip 512 within the ostium, as illustrated in FIG. 30B. For example, if pullwire 3 is initially tensioned at a force of 7 units to bend the distal articulating section 514 to create the 90 degree bend in the distal articulating section 514, pullwire 4 may be tensioned at a force of 9 units to seat the distal tip 512 into the right coronary artery ostium.

Although the catheter 500 has been described as having only one counteracting pullwire 508' oriented 180 degrees from the common mode pullwires 508 to effect bending of the proximal articulating section 518 in only one plane, it should be appreciated that the catheter 500 may optionally have two counteracting pullwires 508'. For example, two counteracting pullwires can be respectively oriented 120 degrees and 240 degrees from the common mode pullwires, thereby allowing bending of the proximal articulating section 518 in all planes.

Furthermore, although the catheter 500 has been described as having only proximal articulating section 518, the catheter 500 may have multiple proximal articulating sections that have increasing lateral flexibility from the most distal articulating section to the most proximal articulating section. For example, in the case where a catheter has two proximal articulating sections, a second transition section similar to the transition section 516 of the catheter 500 can be incorporated between the two proximal articulating sections. This second transition section would transition the counteracting pullwire 508' to an orientation that is adjacent the common mode pullwires 508, so that counteracting pullwire 508' and remaining three pullwires 508 would be in a common mode within the added proximal articulating section. The distal articulating section 514 and first proximal articulating section 518 can be independently bent relative to each other in the same manner as described above. However, in this case, applying the same tension on the counteracting pullwire 508' as the combined tension on the three remaining pullwires 508 will bend the additional proximal articulating section without bending the first articulating section 518, thereby decoupling the two articulating sections 518 from each other. Another counteracting pullwire can be circumferentially disposed 180 degrees from the three pullwires 508 and counteracting pullwire 508' (which are adjacent to each other in the additional proximal articulating section) to bi-directionally bend the additional proximal articulating section in one plane.

As previously discussed above, distal and proximal regions of the catheters 100, 200, 400, and 500 may be fabricated separately, and then mounted to each other when the transition section is fabricated. The reason for fabricating the distal and proximal regions separately is due, in large part, because the circumferential orientations of the pullwire lumens differ between these proximal and distal regions (i.e., equally circumferentially spaced from each other in the distal region, and adjacent to each other in the proximal region). To accommodate the different circumferential orientations of the pullwire lumens, the braid may be incorporated into the catheters using specially designed braiding machines.

Referring to FIG. 32, one embodiment of a braiding machine 600 capable of braiding three wires 602 (only two shown) having one of two selectable circumferential orientations to a tube 604 will be described. The braiding machine 600 generally comprises two interchangeable nose cones 606a, 606b, a feeder assembly 608, and a braiding assembly 610.

As further shown in FIGS. 33A and 33B, each of the nose cones 606a, 606b includes a distal tip 614, an external conical surface 616, and a circular tube aperture 618. The nose cone 606a includes an oblong wire orifice 620 radially outward from coincident with the top of the circular tube aperture 618 (or alternatively, three circular wire orifices (not shown) separate from the circular tube aperture 618 and spaced closely to each other), and the nose cone 606 includes three circular wire orifices 622 radially outward and separate from the circular tube aperture 618 that are equally spaced in an arcuate manner (i.e., one hundred twenty degrees apart) about the circular tube aperture 618. As will be described in further detail below, the nose cone 606a can be used to apply braid over a tube 604 with the three wires 602 positioned adjacent to each other, and the nose cone 606b can be used to apply braid over a tube 604 with the three wires 602 positioned circumferentially equidistant from each other (i.e. 120 degrees from each other). The size of the tube aperture 618 is preferably large enough to just accommodate the tube 604 and any layers that it may carry, the size of the oblong wire orifice 620 is preferably large enough to just accommodate the wires 604 and any layers that they may carry in a side-by-side relationship, and the sizes of the circular wire orifices 622 are preferably large enough to just accommodate the respective wires 604 and any layers that they may carry.

The feeder assembly 608 is configured for advancing the tube 604 through the circular tube aperture 618 and the three wires 602 through the oblong wire orifice 620 or the circular wire orifices 622 at the top of the circular tube aperture 618. The feeder assembly 608 may be conventional and include a set of drive rollers 624 distal to the nose cone 606 that pull the tube 604 and wires 602, and a set of tensioning rollers (not shown) proximal to the nose cone 606 that maintain tension on the tube 604 and wires 602 as they are fed through the nose cone 606. The feeder assembly 608 can be programmed to change the speed at which the tube 604 and wires 602 are advanced through the nose cone 606, such that the pic count of the braid may be varied.

The braiding assembly 610 is configured for braiding a plurality of filaments 628 around the tube 604 and wires 602 as they are advanced through nose cone 606. To this end, the braiding assembly 610 includes a plurality of spindles 630, each of which wraps a respective filament 628 around the tube 604 and wires 602. The spindles 630 rotate around each other and move in and out in a coordinated manner, such that the filaments 628 form a braid on the tube 604 and wires 602. The braiding assembly 610 and either of the nose cones 606a, 606b are arranged relative to each other, such that the external surface 616 of the respective nose cone 606a, 606b serves as a bearing surface for the filaments 628 as they are braided around the tube 604 and the wires 602 at the distal tip 614 of the nose cone 606a, 606b. In the illustrated embodiment, sixteen spindles 630 and corresponding filaments 628 (only two shown) are provided to create the braid, although any number of spindles 630 and filaments 628 can be used.

As briefly discussed above, the nose cones 606a, 606b can be interchanged with one another to apply braid over tubes 604 and three wires 602 of two different orientations. In particular, the first nose cone 606a will be installed on the braiding machine 600 when fabricating a braided assembly having wires 602 that are adjacent to each other. That is, the oblong wire orifice 620 of the first nose cone 606a will maintain a set of three wires 602 in a closely grouped fashion, such that they remain circumferentially adjacent to each other as the filaments 628 are braided over a tube 604 and the wires 602. In contrast, the second nose cone 606a will be installed on the braiding machine 600 when fabricating a braided assembly having wires 602 that circumferentially equidistant from each other. That is, the three separate wire orifices 622 of the second nose cone 606b will maintain another set of three wires 602 circumferentially equidistant from each other (in this case, 120 degrees from each other), such that they remain equidistant from each other as the filaments 628 are braided over another tube 604 and the wires 602. It should be appreciated that additional or alternative nose cones with different numbers of wire orifices or wire orifices of different orientations can be used to fabricate different braided assemblies.

Having described the structure and function of the braiding machine 600, one method of using the braiding machine 600 to fabricate a catheter will now be described. In this embodiment, the fabricated catheter can be similar to the catheter 400 described above, with the exception that this catheter has three, instead of four, pullwires.

A distal articulating section can be fabricated by first inserting a copper wire process mandrel through a lumen of an inner polymer tube (e.g., a PTFE extrusion) 604 having the intended length of the distal articulating section. Then, using the braiding machine 600 with the second nose cone 606b, a first layer of braiding is laid down over the length of the inner polymer tube 604. Notably, this step only requires the inner polymer tube to be advanced through the tube aperture 618 without advancing any of the three wires 602 through the wire orifices 622 of the second nose cone 606b. Next, the three wires 602 (which take the form of PTFE-coated stainless steel wire process mandrels) are respectively disposed over the length of the braided inner polymer tube 604 in three equally spaced circumferential positions (i.e., clocked 120 degrees from each other), and a second layer of braiding is laid down over the three wires 602. This step requires both the braided inner polymer tube 604 to be advanced through the tube aperture 618 and the wires 602 to be advanced through the wire orifices 622 of the second nose cone 606b during the braiding process. Next, one or more outer tubular polymer tubes are laminated over the fully braided inner polymer tube. Then, the center copper wire can be pulled from the assembly to create a working lumen, and the three stainless steel wires 602 can be pulled from the assembly to respectively create three pullwire lumens.

In a similar manner, a proximal shaft section can be fabricated by first inserting a copper wire process mandrel the lumen of an inner polymer tube (e.g., a PTFE extrusion)

604 having the intended length of the proximal shaft section. Then, using the braiding machine 600 with the first nose cone 606a, a first layer of braiding is laid down over the length of the inner polymer tube 604. Notably, this step only requires the inner polymer tube 604 to be advanced through the tube aperture 618 without advancing any of the three wires 602 through the oblong aperture 12 of the first nose cone 606a. Next, the three wires 602 (which take the form of PTFE-coated stainless steel wire process mandrels with polyimide tubing) are respectively disposed over the length of the braided inner polymer tube 604 in adjacent positions, and a second layer of braiding is laid down over the three wires 602. This step requires both the braided inner polymer tube 604 to be advanced through the tube aperture 618 and the wires 602 to be advanced through the oblong aperture of the first nose cone 606a during the braiding process. Next, one or more outer tubular polymer tubes are laminated over the fully braided inner polymer tube. Then, the center copper wire can be pulled from the assembly to create a working lumen, and the three stainless steel wires 602 can be pulled from the assembly to respectively create three pullwire lumens.

Next, the distal articulating section and the proximal shaft section are coupled to each other by fabricating a transition section between the distal articulating section and proximal shaft section and pullwires with the control ring are installed in the same manner described above with respect to fabricating the transition section 416 to couple the distal articulating section 414 and the combined proximal articulating section 418/proximal shaft section 420 together, with the exception that three pullwire lumens and corresponding pullwires, instead of four pullwire lumens and corresponding pullwires, are incorporated into the catheter.

Referring to FIGS. 34 and 35, another embodiment of a braiding machine 700 capable of braiding three wires 602 having two different circumferential orientations to a single tube 604 will be described. The braiding machine 700 is similar to the previously described braiding machine 600, with the exception that it is capable of applying the braid to a single tube with different circumferential orientations of the wires 602. In this manner, the wires 602, and thus the pullwire lumens, need not be bonded to any portion of the inner polymer tube. That is, one continuous braid and three continuous wires 602 with varying circumferential orientations can be applied over a single tube 604. In this manner, not only does this eliminate the processing time required to independently fabricate and subsequently join the separate sections of the catheter together, it eliminates the inherent variation that may result in manually positioning the lumens of the separate catheter sections together. Furthermore, the step of bonding wires to the transition section that would otherwise be needed to join the distal articulating section and proximal shaft section together is eliminated. Since the wires must be otherwise weakly bonded to the inner polymer tube as a stronger bond would negatively affect the performance of the completed catheter, this may be significant, since the braiding process is not gentle and could break or shift the bonds between the wires and the inner polymer tube.

The braiding machine 700 generally comprises the feeder assembly 608 and a braiding assembly 610, the details of which have been described above. The braiding machine 700 differs from the braiding machine 600 in that it comprises a single nose cone 706 and an iris assembly 712 (shown in phantom), which in the illustrated embodiment, is installed within the nose cone 706.

Like the previously described nose cones 606a, 606b, the nose cone 706 includes a distal tip 714, an external conical surface 716, and a circular tube aperture 718. In the illustrated embodiment, the nose cone 706 does not include a wire aperture per se. Rather, the size of the tube aperture 718 is preferably large enough to accommodate both the tube 604 and any layers that it may carry, as well as the wires 602 and any layers that they may carry (i.e., the diameter of the tube aperture 718 is equal to or slightly greater than the combined diameters of the tube 604 and one of the wires 602). The iris assembly 712 is operable to adjust the relative circumferential positions of the wires 704 as the exit from the tube aperture 718 around the tube 702, and in the illustrated embodiment, between a relative circumferential position where the wires 704 are adjacent to each other in a side-by-side relationship and a relative circumferential position where the wires 704 are positioned circumferentially equidistant from each other (i.e. 120 degrees from each other).

To this end, and with reference to FIGS. 36-41, the iris assembly 712 comprises three stacked iris plates 720 a, 720 b, and 720 c, each of which includes a center aperture 722, a wire orifice 724 disposed radially outward from the center aperture 722, and at least one arcuate channel 726 in circumferential alignment with the respective wire orifice 724. The feeder assembly 608 is configured for advancing the tube 604 through the center apertures 722 of the iris assembly 712, as well as through the tube aperture 718 of the nose cone 706, and the for advancing the wires 602 through the respective wire orifices 724 of the iris assembly 712, as well as through the periphery of the tube aperture 718 of the nose cone 706.

The iris plates 720 are rotatable relative to each other to adjust the circumferential orientation of the wire orifices 724 relative to each other, while the arcuate channel(s) 726 of each respective iris plate 720 is coincident with the wire orifices 724 of the remaining two iris plates 720. In this manner, any wire orifice 724 may be adjusted via rotation of the respective iris plate 720 without blocking the path of the wire orifices 724 of the other iris plates 720. The braiding assembly 610 is configured for braiding the filaments 628 around the tube 604 and the wires 602 as they are fed through the iris assembly 712 and as the respective iris plates 720 are rotated relative to each other to create the braided tube assembly. Thus, the iris assembly 712 may be operated to circumferentially orient the wires 602 relative to each other differently along the braided tube assembly.

In the illustrated embodiment, the iris plate 720a is rotationally fixed relative to the nose cone 706, while the remaining two iris plates 720 b, 720 c are capable of being rotated relative to the nose cone 706. To facilitate their rotation, each of the two iris plates 720 b, 720 c includes a lever 728 that can be manipulated to rotate the respective iris plate 720 b, 720 c. The levers 728 may be manipulated, such that rotation of the respective iris plates 720 b, 720 c can be synchronously automated with the feeder assembly 608. To accommodate the levers 728, the nose cone 706 may include a slot 730 through which the levers 728 for connection to the motor and linkage assembly. To facilitate rotation of the iris plates 720 relative to each other, the iris assembly 712 further comprises thrust bearings 730 (shown in phantom in FIG. 36) mounted between the iris plates 720, and in particular, a first thrust bearing 730a mounted between the respective iris plates 720 a, 720 b, a second thrust bearing 730 b mounted between the respective iris plates 720 b, 720 c, and a third thrust bearing 730 c mounted between the iris plate 720 c and the distal tip 714 of the nose cone 706. Each of the bearings 730 includes a center aperture 732 that accommodates the tube 604 and wires 602 as they pass through the iris assembly 712.

Referring back to FIG. 34, the braiding machine 700 further comprises a mechanical driver 734 (which may include a motor and appropriate linkage) connected to the levers 728 for rotating the iris plates 720 relative to each other, and a controller 736 configured, while the braiding assembly 610 is braiding the filaments 628 around the tube 604 and the wires 602 over a period of time, instructing the mechanical driver 734 to maintain an initial relative rotational orientation of the iris plates 720, such that spacings between the respective wire orifices 724 are equal over a first portion of the time period, instructing the mechanical driver 734 to gradually change the rotational orientation of the iris plates 720, such that spacings between the respective wire orifices 724 decrease over a second portion of the time period until the respective wire orifices 724 are adjacent to each other, and instructing the mechanical driver 734 to maintain the changed relative rotational orientation of the iris plates 720, such that the respective wire orifices 724 are adjacent to each other over a third portion of the time period.

As briefly discussed above, the wire orifices 724 and arcuate channel(s) 726 of the respective iris plates 720 are arranged in a manner that allows the three wire orifices 724 to be placed between an adjacent circumferential orientation and an equally spaced circumferential orientation without blocking the paths of the wire orifices 724.

Figure 38:
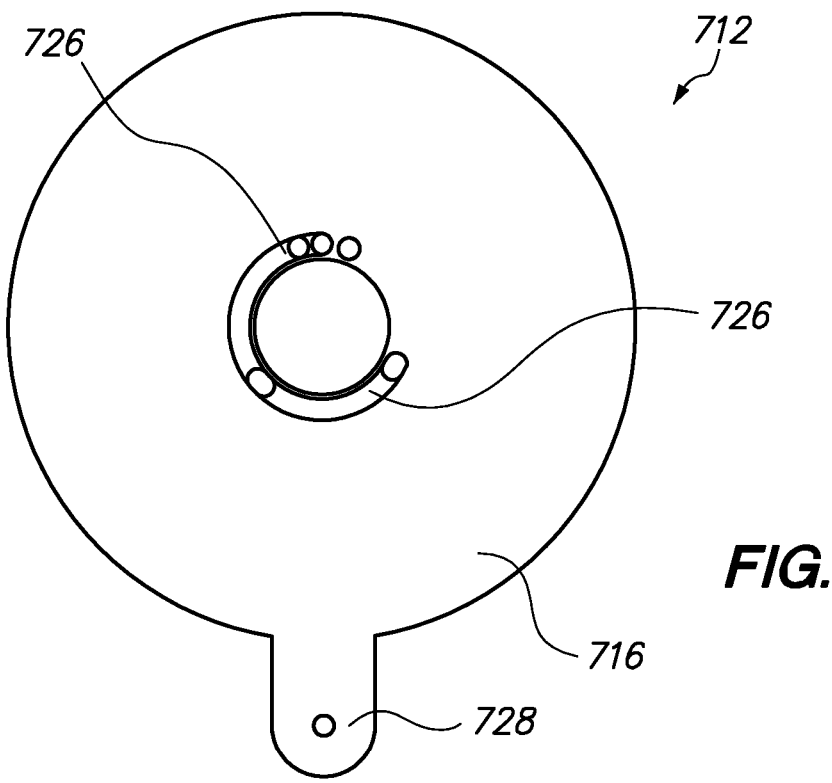
FIG. 38 is an axial view of the iris assembly of FIG. 36, particularly showing the iris assembly in a first position that groups three wire mandrels circumferentially adjacent each other.
Figure 39:
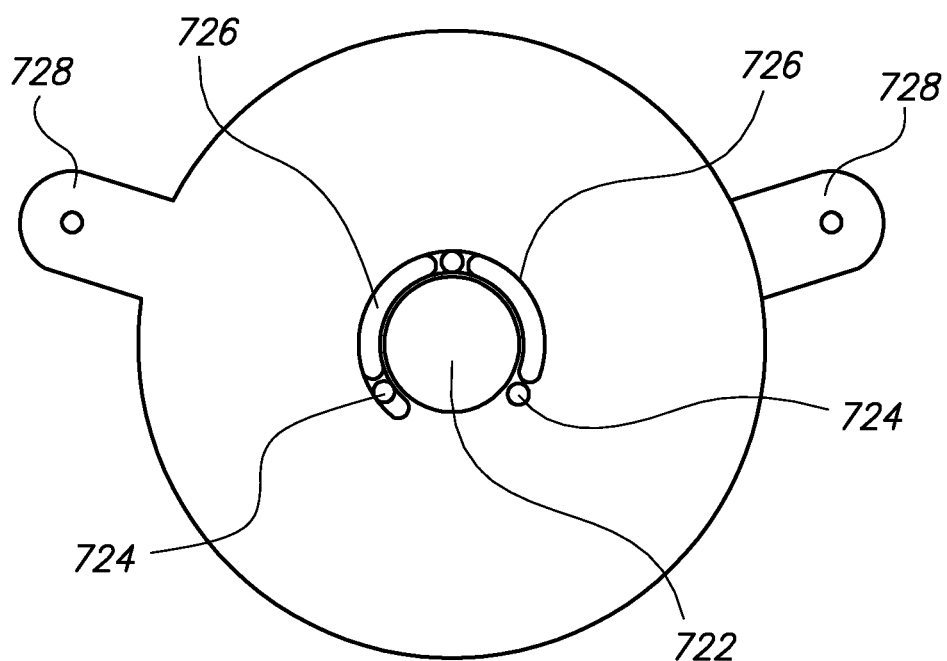
FIG. 39 is an axial view of the iris assembly of FIG. 36, particularly showing the iris assembly in a second position that spaces three wire mandrels equidistant from each other.
Figure 40:
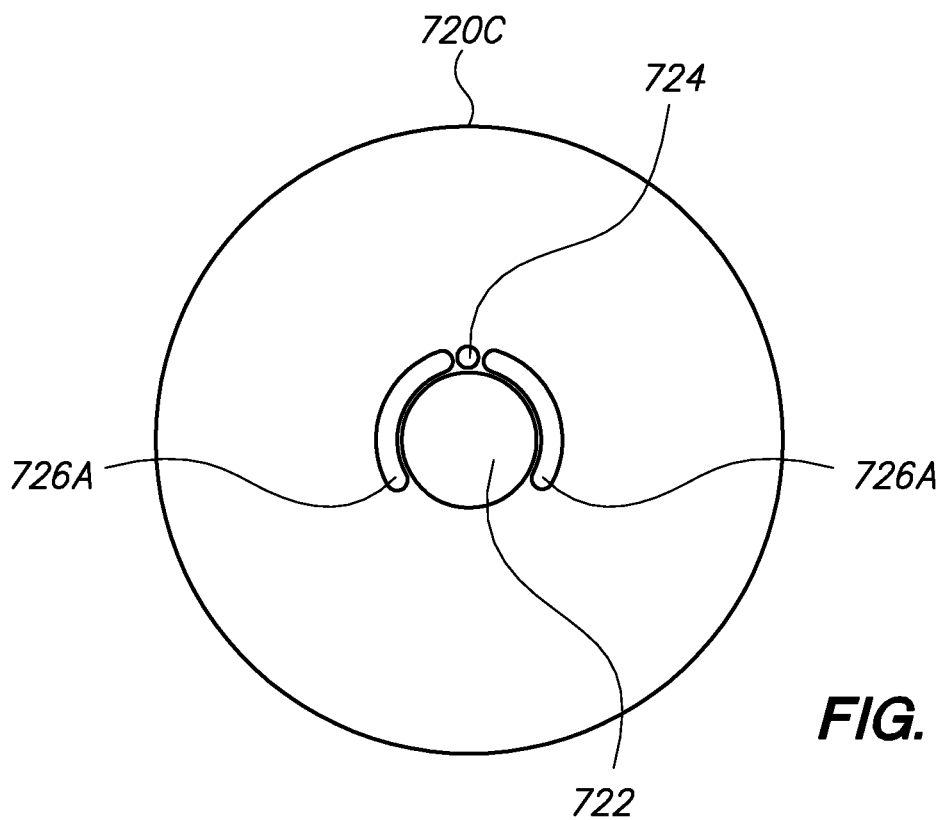
FIG. 40 is an axial view of a first iris plate for use in the iris assembly of FIG. 36.
Figure 41:
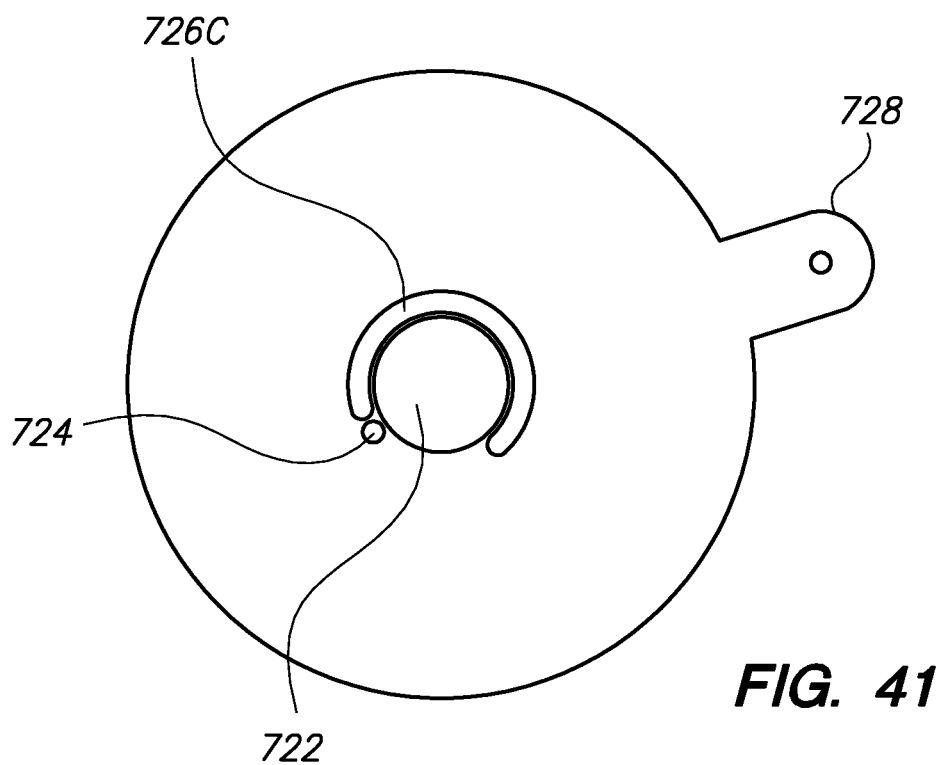
FIG. 41 is an axial view of a second iris plate for use in the iris assembly of FIG. 36.
Figure 42:
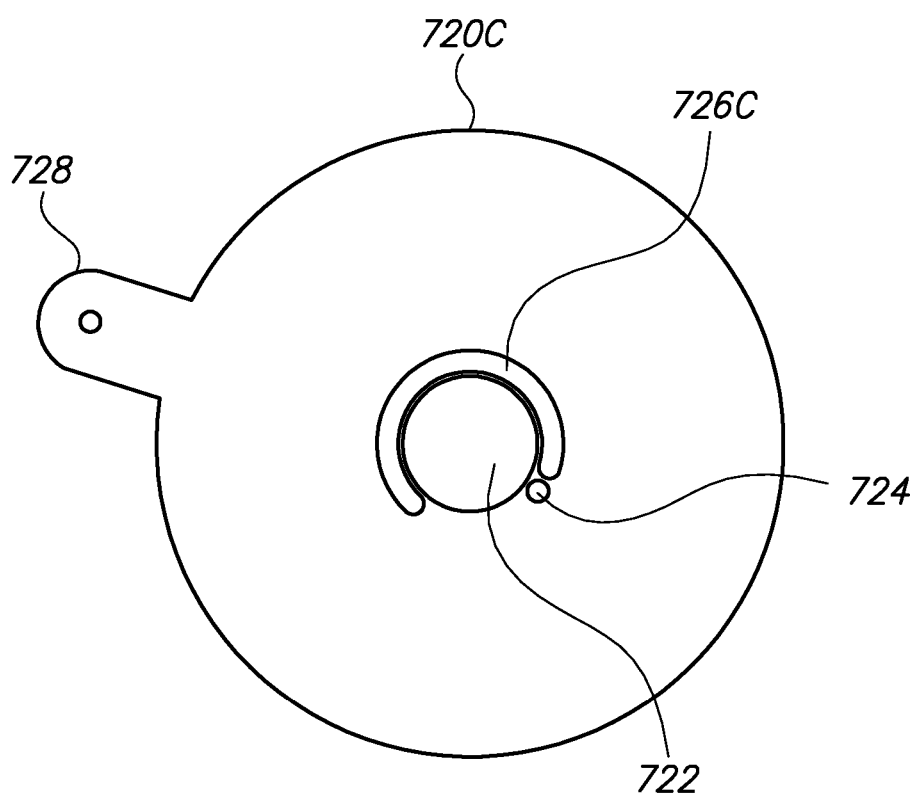
FIG. 42 is an axial view of a third iris plate for use in the iris assembly of FIG. 36.

To this end, the first iris plate 720 *a* has two arcuate channels 726 *a* that straddle the respective wire orifice 724 *a* (FIG. 40) The furthest extent of each of these arcuate channels 726*a* is at least 120 degrees from the wire orifice 724 *a*. The second iris plate 720 *b* has a single arcuate channel 720 *b* with a furthest extent of at least 240 degrees counterclockwise from the wire orifice 724 *b* of the second iris plate 720 *b* (FIG. 41). The third iris plate 720 *c* has a single arcuate channel 720 *c* with a furthest extent of at least 120 degrees clockwise from the wire orifice 724 *c* of the third iris plate 720 *c* (FIG. 42). It can be appreciated that, when the levers 728 of the respective iris plates 720 *b*, 720 *c* are moved to their downward position, the wire orifices 724 *a*-724 *c* are located circumferentially adjacent to each other, as shown in FIG. 38. In contrast, when the levers 728 of the respective iris plates 720*b*, 720*c* are moved to their upward position, the wire orifices 724 *a*-724 *c* are circumferentially spaced equidistant from each other, as shown in FIG. 39.

The right arcuate channel 726 *a* of the first iris plate 720 *a* remains coincident with the wire orifice 724 *b* of the second iris plate 720 *b* as the lever 728 of the second iris plate 720 *b* is moved between the upward and downward positions. Thus, the right arcuate channel 726 *a* prevents the first iris plate 720 *a* from blocking the path of the wire orifice 724 *b* of the second iris plate 720 *b*. Similarly, the left arcuate channel 726 *a* of the first iris plate 720 *a* remains coincident with the wire orifice 724 *c* of the third iris plate 720 *c* as the lever 728 of the third iris plate 720 *c* is moved between the upward and downward positions. Thus, the left arcuate channel 726 *a* prevents the first iris plate 720 *a* from blocking the path of the wire orifice 724 *c* of the third iris plate 720 *c*.

The arcuate channel 726 *b* of the second iris plate 720 *b* remains coincident with the wire orifice 724 *a* of the first iris plate 720 *a* and the wire orifice 724 *c* of the third iris plate 720 *c* as the lever 728 of the second iris plate 720 *b* is moved between the upward and downward positions. Thus, the arcuate channel 726 *b* prevents the second iris plate 720 *b* from blocking the paths of the wire orifice 724 *a* of the first iris plate 720 *a* and the wire orifice 724 *c* of the third iris plate 720*c*. The arcuate channel 726 *c* of the third iris plate 720*c* remains coincident with the wire orifice 724 *a* of the first iris plate 720 *a* and the wire orifice 724 *b* of the second iris plate 720 *b* as the lever 728 of the third iris plate 720 *c* is moved between the upward and downward positions. Thus, the arcuate channel 726 *c* prevents the third iris plate 720*c* from blocking the paths of the wire orifice 724 *a* of the first iris plate 720 *a* and the wire orifice 724 *b* of the second iris plate 720 *b*.

Having described the structure and function of the braiding machine 700, one method of using the braiding machine 700 to fabricate a catheter will now be described. The catheter can be fabricated by first inserting a copper wire process mandrel through a lumen of an inner polymer tube (e.g., a PTFE extrusion) having the intended length of the catheter. Then, a first layer of braiding is laid down over the length of the inner polymer tube. Notably, this step only requires the inner polymer tube to be advanced through the center aperture 722 of the iris assembly 712 and the tube aperture 718 of the nose cone 706 without advancing any of the three wires 602 through the wire orifices 724 of the iris assembly 712 or the tube aperture 718 of the nose cone 706. Next, the three wires 602 (which take the form of PTFE-coated stainless steel wire process mandrels) are respectively disposed over the length of the braided inner polymer tube in varying circumferential positions, and a second layer of braiding is laid down over the three wires 602.

This step requires both the braided inner polymer tube to be advanced through the center aperture 722 of the iris assembly 712 and the tube aperture 618 of the nose cone 706, and the wires 602 to be advanced through the wire orifices 724 of the iris assembly 712 and the tube aperture 718 of the nose cone 706 during the braiding process. Furthermore, during this step, the levers 728 of the iris plates 720 *b*, 720 *c* are manipulated to change the relative circumferential positions of the wire orifices 724 of the iris assembly 712, and thus, the wires 602 on which the braid is laid. In particular, during the length of the distal articulating section of the catheter, the levers 728 of the respective iris plates 720 *b*, 720 *c* are moved to their downward position, such that the wire orifices 724 *a*-724 *c*, and thus, the wires 602, are located circumferentially adjacent to each other. During the length of the transition section of the catheter, the levers 728 of the respective iris plates 720 *b*, 720 *c* are gradually moved to their upward position, such that the wire orifices 724 *a*-724 *c*, and thus, the wires 602, are gradually moved from a position where they are circumferentially adjacent to each other at the distal-most extent of the transition section to a position where they are circumferentially spaced equidistant from each other at the proximal-most extent of the transition section. During the length of the proximal shaft section of the catheter, the levers 728 of the respective iris plates 720 *b*, 720 *c* are maintained in their upward position, such that the spacings of the wire orifices 724 *a*-724 *c*, and thus, the wires 602, is maintained circumferentially equidistant from each other. Next, one or more outer tubular polymer tubes are laminated over the fully braided inner polymer tube. Then, the center copper wire can be pulled from the assembly to create a working lumen, and the three stainless steel wires 602 can be pulled from the assembly to respectively create three pullwire lumens.

Although the iris assembly has been described as comprising three iris plates for respectively accommodating three wires 602, it should be appreciated that the number of iris plates can be less or more than three, depending on the number of wires 602 that are to be incorporated into the catheter.

For example, in the case where two wires 602 are to be accommodated, the iris assembly may comprise only two iris plates. In this case, one of the iris plates will have a single arcuate channel with a furthest extent at least 180 degrees clockwise from the wire orifice, and the other iris plate will have a single arcuate channel with a furthest extent at least 180 degrees counterclockwise from the wire orifice. Thus, the wire orifices in this iris assembly may be selectively located circumferentially adjacent to each other or circumferentially spaced equidistant from each other by 180 degrees.

In the case where four wires 602 are to be accommodated, the iris assembly may comprise four iris plates. In this case, the first iris plate has a single arcuate channel that extends virtually all the way around the respective iris plate from one side of the wire orifice to the other side of the wire orifice. The second iris plate has a single arcuate channel with a furthest extent of at least 270 degrees counterclockwise from the wire orifice of the second iris plate. The third iris plate has a single arcuate channel with a furthest extent of at least 270 degrees clockwise from the wire orifice of the third iris plate. The fourth iris plate has a single arcuate channel that extends virtually all the way around the respective iris plate from one side of the wire orifice to the other side of the wire orifice. Thus, the wire orifices in this iris assembly may be selectively located circumferentially adjacent to each other or circumferentially spaced equidistant from each other by 90 degrees.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A robotically controlled steerable catheter system, comprising:
    a catheter comprising a shaft portion, a proximal articulating section positioned distal to the shaft portion, and a distal articulating section positioned distal to the proximal articulating section, wherein the distal articulating section has a flexural stiffness that is less than the proximal articulating section, and wherein articulation of the proximal articulating section and the distal articulating section are independently controlled;
    four pullwires extending through at least a proximal portion of the catheter, within the proximal portion the four pullwires extending along a first side of the catheter, wherein at least three of the four pullwires are coupled to the distal articulating section and a fourth pullwire is coupled to the proximal articulating section at a location within the proximal articulating section, the three pullwires extending along the first side of the proximal articulating section that circumferentially opposes the location within the proximal articulation section where the fourth pullwire is attached;
    a robotic instrument driver;
    a mechanical interface coupling the four pullwires and the proximal end of the catheter to the robotic instrument driver; and
    a control station communicatively coupled to the instrument driver, wherein the control station comprises a master input device for interfacing with a user and a computing device programmed to provide control of a distal articulation angle and a distal roll of the catheter, and wherein the computing device provides control of the catheter by computing a displacement of each of the pullwires independently.

2. The robotically controlled steerable catheter system of claim 1, wherein each of the three of the four pullwires is equally spaced circumferentially around the distal articulating section.

3. The robotically controlled steerable catheter system of claim 2, wherein each of the three of the four pullwires is configured to be selectively tensioned to bend the distal articulating section in any direction.

4. The robotically controlled steerable catheter system of claim 3, wherein the catheter is configured such that simultaneously tensioning the fourth pullwire with the selective tensioning of the three of the four pullwires prevents unwanted deflection of the proximal articulating section.

5. The robotically controlled steerable catheter system of claim 4, wherein the catheter is configured such that further tensioning of the fourth pullwire causes the proximal articulating section to bend in one direction.

6. The robotically controlled steerable catheter system of claim 5, wherein the catheter is configured such that subsequent equal tensioning of the three of the four pullwires bends the proximal articulating section in one direction without causing further bending of the distal articulating section.

7. The robotically controlled steerable catheter system of claim 1, wherein each of the three of the four pullwires is configured to be selectively tensioned and released in a sequential fashion to rotate the distal articulating section.

8. The robotically controlled steerable catheter system of claim 7, wherein the distal articulating section is rotatable in 360 degrees.

9. The robotically controlled steerable catheter system of claim 1, wherein a working lumen and four pullwire lumens extend through the catheter, the four pullwire lumens positioned between an outer diameter of the catheter and the working lumen.

10. The robotically controlled steerable catheter system of claim 1, further comprising a transition section disposed between the distal and proximal articulating sections.

11. The robotically controlled steerable catheter system of claim 10, wherein the three of the four pullwires are positioned in a spiral configuration around the transition section such that the three of the four pullwires are equally spaced at a distal end of the transition section and converge at a proximal end of the transition section.

12. The robotically controlled steerable catheter system of claim 11, wherein the converged portion of the three of the four pullwires is positioned opposite the fourth pullwire.

13. The robotically controlled steerable catheter system of claim 1, wherein the computing device is configured to compute a required displacement for each of the pullwires based on elastic behavior of the distal and proximal articulating sections and catheter stiffness.

14. The robotically controlled steerable catheter system of claim 1, wherein the flexible shaft portion comprises a length greater than each of the proximal articulating section and the distal articulating section.

15. The robotically controlled steerable catheter system of claim 14, wherein the flexible shaft portion comprises a length greater than the proximal articulating section and the distal articulating section combined.

16. The robotically controlled steerable catheter system of claim 1, wherein the proximal articulating section is manufactured separately from the distal articulating section, and wherein the proximal articulating section is mounted to the distal articulating section.

* * * * *